(12) United States Patent
Caffaro et al.

(10) Patent No.: US 12,377,131 B2
(45) Date of Patent: Aug. 5, 2025

(54) CYTOKINE CONJUGATES FOR THE TREATMENT OF AUTOIMMUNE DISEASES

(71) Applicant: Synthorx, Inc., La Jolla, CA (US)

(72) Inventors: Carolina E. Caffaro, San Diego, CA (US); Marcos Milla, Carlsbad, CA (US); Jerod Ptacin, San Diego, CA (US)

(73) Assignee: SYNTHORX, INC., Bridgewater, NJ (US)

( * ) Notice: Subject to any disclaimer, the term of this patent is extended or adjusted under 35 U.S.C. 154(b) by 185 days.

(21) Appl. No.: 18/179,198

(22) Filed: Mar. 6, 2023

(65) Prior Publication Data

US 2023/0302089 A1    Sep. 28, 2023

Related U.S. Application Data

(62) Division of application No. 16/634,487, filed as application No. PCT/US2018/045265 on Aug. 3, 2018, now Pat. No. 11,622,993.

(60) Provisional application No. 62/540,781, filed on Aug. 3, 2017.

(51) Int. Cl.
| | |
|---|---|
| *A61K 38/20* | (2006.01) |
| *A61K 47/54* | (2017.01) |
| *A61K 47/60* | (2017.01) |
| *A61K 47/61* | (2017.01) |
| *A61K 47/64* | (2017.01) |
| *A61K 47/65* | (2017.01) |
| *A61K 47/68* | (2017.01) |
| *C07K 14/55* | (2006.01) |
| *C07K 14/715* | (2006.01) |
| *A61K 38/00* | (2006.01) |

(52) U.S. Cl.
CPC ........ *A61K 38/2013* (2013.01); *A61K 47/542* (2017.08); *A61K 47/60* (2017.08); *A61K 47/61* (2017.08); *A61K 47/643* (2017.08); *A61K 47/644* (2017.08); *A61K 47/65* (2017.08); *A61K 47/68* (2017.08); *C07K 14/55* (2013.01); *C07K 14/7155* (2013.01); *A61K 38/00* (2013.01)

(58) Field of Classification Search
CPC .................................................. A61K 38/2013
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,667,025 A | 5/1987 | Miyoshi et al. |
| 4,683,195 A | 7/1987 | Mullis et al. |
| 4,683,202 A | 7/1987 | Mullis |
| 4,762,779 A | 8/1988 | Snitman |
| 4,766,106 A | 8/1988 | Katre et al. |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,849,513 A | 7/1989 | Smith et al. |
| 4,851,512 A | 7/1989 | Miyaji et al. |
| 4,876,335 A | 10/1989 | Yamane et al. |
| 4,902,502 A | 2/1990 | Nitecki et al. |
| 4,904,582 A | 2/1990 | Tullis |
| 4,910,300 A | 3/1990 | Urdea et al. |
| 4,931,544 A | 6/1990 | Katre et al. |
| 4,948,882 A | 8/1990 | Ruth |
| 4,958,013 A | 9/1990 | Letsinger |
| 4,965,188 A | 10/1990 | Mullis et al. |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,089,261 A | 2/1992 | Nitecki et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |

(Continued)

FOREIGN PATENT DOCUMENTS

| | | |
|---|---|---|
| CN | 102665754 A | 9/2012 |
| CN | 104231068 A | 12/2014 |

(Continued)

OTHER PUBLICATIONS

Needleman et al. A general method applicable to the search for similarities in the amino acid sequence of two proteins. J. Mol. Biol. 48:443-453 (1970).

(Continued)

*Primary Examiner* — Prema M Mertz

(74) *Attorney, Agent, or Firm* — McNeill PLLC

(57) ABSTRACT

Disclosed herein are interleukin (IL) conjugates (e.g., IL-2 conjugates) and use in the treatment of one or more indications. Also described herein are pharmaceutical compositions and kits comprising one or more of the interleukin conjugates (e.g., IL-2 conjugates).

23 Claims, 12 Drawing Sheets

Specification includes a Sequence Listing.

(56) References Cited

U.S. PATENT DOCUMENTS

| | | |
|---|---|---|
| 5,188,897 A | 2/1993 | Suhadolnik et al. |
| 5,206,344 A | 4/1993 | Katre et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,229,109 A | 7/1993 | Grimm et al. |
| 5,232,841 A | 8/1993 | Hashimoto et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,268,273 A | 12/1993 | Buckholz |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,370,995 A | 12/1994 | Hennecke et al. |
| 5,371,241 A | 12/1994 | Brush |
| 5,389,529 A | 2/1995 | Panayotatos et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,719 A | 11/1995 | Meng et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,899 A | 1/1997 | Sato et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,612,199 A | 3/1997 | Western et al. |
| 5,614,185 A | 3/1997 | Koths et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,643,564 A | 7/1997 | Hamaguchi et al. |
| 5,645,985 A | 7/1997 | Froehler et al. |
| 5,646,265 A | 7/1997 | McGee |
| 5,648,247 A | 7/1997 | Picataggio et al. |
| 5,656,493 A | 8/1997 | Mullis et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,712,114 A | 1/1998 | Mankovich et al. |
| 5,714,331 A | 2/1998 | Buchardt et al. |
| 5,719,262 A | 2/1998 | Buchardt et al. |
| 5,747,646 A | 5/1998 | Hakimi et al. |
| 5,750,692 A | 5/1998 | Cook et al. |
| 5,763,588 A | 6/1998 | Matteucci et al. |
| 5,830,653 A | 11/1998 | Froehler et al. |
| 5,834,594 A | 11/1998 | Hakimi et al. |
| 5,846,818 A | 12/1998 | Robinson et al. |
| 5,888,732 A | 3/1999 | Hartley et al. |
| 5,932,474 A | 8/1999 | Tsien et al. |
| 6,005,096 A | 12/1999 | Matteucci et al. |
| 6,008,378 A | 12/1999 | Tsien et al. |
| 6,010,871 A | 1/2000 | Takahara et al. |
| 6,013,526 A | 1/2000 | Takahara et al. |
| 6,054,271 A | 4/2000 | Tsien et al. |
| 6,124,090 A | 9/2000 | Rose et al. |
| 6,143,557 A | 11/2000 | Hartley et al. |
| 6,171,861 B1 | 1/2001 | Hartley et al. |
| 6,261,797 B1 | 7/2001 | Sorge et al. |
| 6,268,490 B1 | 7/2001 | Imanishi et al. |
| 6,270,969 B1 | 8/2001 | Hartley et al. |
| 6,277,608 B1 | 8/2001 | Hartley et al. |
| 6,288,302 B1 | 9/2001 | Yu et al. |
| 6,294,323 B1 | 9/2001 | Ullman et al. |
| 6,365,375 B1 | 4/2002 | Dietmaier et al. |
| 6,391,544 B1 | 5/2002 | Salituro et al. |
| 6,451,569 B1 | 9/2002 | Tsien et al. |
| 6,525,191 B1 | 2/2003 | Ramasamy |
| 6,670,461 B1 | 12/2003 | Wengel et al. |
| 6,720,140 B1 | 4/2004 | Hartley et al. |

(56) References Cited

U.S. PATENT DOCUMENTS

| | | |
|---|---|---|
| 6,770,748 B2 | 8/2004 | Manishi et al. |
| 6,794,499 B2 | 9/2004 | Wengel et al. |
| 6,906,170 B1 | 6/2005 | Lider et al. |
| 6,955,807 B1 | 10/2005 | Shanafelt et al. |
| 7,034,133 B2 | 4/2006 | Wengel et al. |
| 7,045,337 B2 | 5/2006 | Schultz et al. |
| 7,053,207 B2 | 5/2006 | Wengel |
| 7,105,653 B2 | 9/2006 | Shanafelt et al. |
| 7,393,632 B2 | 7/2008 | Cheo et al. |
| 7,399,845 B2 | 7/2008 | Seth et al. |
| 7,427,672 B2 | 9/2008 | Imanishi et al. |
| 7,625,717 B2 | 12/2009 | Chin et al. |
| 7,670,823 B1 | 3/2010 | Hartley et al. |
| 7,741,457 B2 | 6/2010 | Seth et al. |
| 7,744,861 B2 | 6/2010 | Zhao et al. |
| 7,803,777 B2 | 9/2010 | DeFrees |
| 8,012,465 B2 | 9/2011 | Elias et al. |
| 8,252,743 B2 | 8/2012 | Guyon et al. |
| 8,273,833 B2 | 9/2012 | Bentley et al. |
| 8,420,792 B2 | 4/2013 | Tian et al. |
| 8,501,805 B2 | 8/2013 | Seth et al. |
| 8,546,556 B2 | 10/2013 | Seth et al. |
| 8,557,776 B2 | 10/2013 | Lehmann et al. |
| 8,609,383 B2 | 12/2013 | Young et al. |
| 9,089,614 B2 | 7/2015 | Lin et al. |
| 9,682,934 B2 | 6/2017 | Stafford et al. |
| 9,732,134 B2 | 8/2017 | Gavin et al. |
| 9,840,493 B2 | 12/2017 | Yang et al. |
| 9,861,705 B2 | 1/2018 | Bossard et al. |
| 9,938,516 B2 | 4/2018 | Zimmerman et al. |
| 9,988,619 B2 | 6/2018 | Zimmerman et al. |
| 10,610,571 B2 | 4/2020 | Ptacin et al. |
| 10,851,144 B2 | 12/2020 | Butz et al. |
| 10,960,079 B2 | 3/2021 | Bossard et al. |
| 11,077,195 B2 | 8/2021 | Ptacin et al. |
| 11,622,993 B2 | 4/2023 | Ptacin et al. |
| 11,701,407 B2 | 7/2023 | Ptacin et al. |
| 2002/0001804 A1 | 1/2002 | Mitchell et al. |
| 2002/0007051 A1 | 1/2002 | Cheo et al. |
| 2003/0083373 A1 | 5/2003 | Tsien et al. |
| 2004/0171570 A1 | 9/2004 | Allerson et al. |
| 2005/0112590 A1 | 5/2005 | Boom et al. |
| 2005/0118623 A1 | 6/2005 | Belousov et al. |
| 2005/0130923 A1 | 6/2005 | Bhat et al. |
| 2006/0035254 A1 | 2/2006 | Manoharan et al. |
| 2006/0074035 A1 | 4/2006 | Hong et al. |
| 2006/0084136 A1 | 4/2006 | Kudlicki et al. |
| 2006/0160187 A1 | 7/2006 | Denis-Mize et al. |
| 2006/0234205 A1 | 10/2006 | Cao et al. |
| 2006/0263771 A1 | 11/2006 | Hirao et al. |
| 2007/0287831 A1 | 12/2007 | Seth et al. |
| 2008/0025947 A1 | 1/2008 | Gillies et al. |
| 2008/0039618 A1 | 2/2008 | Allerson et al. |
| 2008/0300163 A1 | 12/2008 | Cho et al. |
| 2009/0155844 A1 | 6/2009 | Yokoyama et al. |
| 2010/0316595 A1 | 12/2010 | Elias et al. |
| 2010/0323364 A1 | 12/2010 | Sekine et al. |
| 2012/0022013 A1 | 1/2012 | Sinclair et al. |
| 2012/0077252 A1 | 3/2012 | Picataggio et al. |
| 2012/0244112 A1 | 9/2012 | Ast et al. |
| 2012/0315245 A1 | 12/2012 | Leon et al. |
| 2013/0333068 A1 | 12/2013 | Coffin |
| 2014/0046026 A1 | 2/2014 | Garcia et al. |
| 2014/0255345 A1 | 9/2014 | Grabstein et al. |
| 2014/0314864 A1 | 10/2014 | Cheng et al. |
| 2014/0315245 A1 | 10/2014 | Yam et al. |
| 2014/0328791 A1 | 11/2014 | Bossard et al. |
| 2016/0168187 A1 | 6/2016 | Romesberg et al. |
| 2017/0029829 A1 | 2/2017 | Romesberg et al. |
| 2017/0044229 A1 | 2/2017 | Garcia et al. |
| 2017/0260137 A1 | 9/2017 | Stafford et al. |
| 2017/0283469 A1 | 10/2017 | Thanos et al. |
| 2017/0313753 A1 | 11/2017 | Gavin et al. |
| 2017/0369871 A1 | 12/2017 | Ptacin et al. |
| 2018/0051065 A1 | 2/2018 | Yin |
| 2018/0086734 A1 | 3/2018 | Yang et al. |
| 2020/0181220 A1 | 6/2020 | Ptacin et al. |
| 2020/0188484 A1 | 6/2020 | Ptacin et al. |
| 2020/0231644 A1 | 7/2020 | Ptacin et al. |
| 2020/0299349 A1 | 9/2020 | Garcia et al. |
| 2020/0368293 A1 | 11/2020 | Olle |
| 2020/0399338 A1 | 12/2020 | Caffaro et al. |
| 2021/0023230 A1 | 1/2021 | Bossard et al. |
| 2021/0024602 A1 | 1/2021 | Sprogøe et al. |
| 2021/0046160 A1 | 2/2021 | Ptacin et al. |
| 2021/0054040 A1 | 2/2021 | Caffaro et al. |
| 2021/0060169 A1 | 3/2021 | Ikeda et al. |
| 2021/0070827 A1 | 3/2021 | Ptacin et al. |
| 2021/0139554 A1 | 5/2021 | Butz et al. |
| 2021/0196796 A1 | 7/2021 | Penaflor-Aspuria et al. |
| 2021/0221863 A1 | 7/2021 | Kang et al. |
| 2021/0299222 A1 | 9/2021 | Rodriguez et al. |
| 2021/0338829 A1 | 11/2021 | Caffaro et al. |
| 2022/0016249 A1 | 1/2022 | Ptacin et al. |
| 2022/0016252 A1 | 1/2022 | Abbadessa et al. |
| 2022/0273767 A1 | 9/2022 | Caffaro et al. |
| 2022/0324792 A1 | 10/2022 | Aerni et al. |
| 2023/0265148 A1 | 8/2023 | Hu et al. |
| 2023/0277627 A1 | 9/2023 | Caffaro et al. |
| 2023/0416327 A1 | 12/2023 | Caffaro et al. |
| 2024/0082359 A1 | 3/2024 | Ptacin et al. |
| 2024/0226309 A1 | 7/2024 | Abbadessa et al. |
| 2024/0287151 A1 | 8/2024 | Caffaro et al. |

FOREIGN PATENT DOCUMENTS

| | | |
|---|---|---|
| EA | 025851 B1 | 2/2017 |
| EP | 0154316 A2 | 9/1985 |
| EP | 0614907 A1 | 9/1994 |
| EP | 0629633 A2 | 12/1994 |
| EP | 0811385 A2 | 12/1997 |
| EP | 2130835 A4 | 6/2010 |
| EP | 2581450 B1 | 8/2018 |
| EP | 2382228 B1 | 8/2020 |
| EP | 3280725 B1 | 8/2020 |
| EP | 4011388 B1 | 6/2022 |
| EP | 4209503 A1 | 7/2023 |
| JP | S61225199 A | 10/1986 |
| JP | 2007510401 A | 4/2007 |
| WO | 9213869 A1 | 8/1992 |
| WO | 9414226 A1 | 6/1994 |
| WO | 9422890 A1 | 10/1994 |
| WO | 9735869 A1 | 10/1997 |
| WO | 9914226 A2 | 3/1999 |
| WO | 9921013 A1 | 4/1999 |
| WO | 9962923 A2 | 12/1999 |
| WO | 0023456 A1 | 4/2000 |
| WO | 0074724 A2 | 12/2000 |
| WO | 0105801 A1 | 1/2001 |
| WO | 0132887 A1 | 5/2001 |
| WO | 0236626 A1 | 5/2002 |
| WO | 02062816 A1 | 8/2002 |
| WO | 02068216 A1 | 9/2002 |
| WO | 02070533 A2 | 9/2002 |
| WO | 03031464 A2 | 4/2003 |
| WO | 03055898 A1 | 7/2003 |
| WO | 03070918 A2 | 8/2003 |
| WO | 2004007713 A1 | 1/2004 |
| WO | 2004060300 A2 | 7/2004 |
| WO | 2004106356 A1 | 12/2004 |
| WO | 2005007121 A2 | 1/2005 |
| WO | 2005021570 A1 | 3/2005 |
| WO | 2005026187 A1 | 3/2005 |
| WO | 2005092928 A1 | 10/2005 |
| WO | 2005045015 A3 | 12/2005 |
| WO | 2004099231 A3 | 3/2006 |
| WO | 2006049297 A1 | 5/2006 |
| WO | 2006081510 A2 | 8/2006 |
| WO | 2006082184 A2 | 8/2006 |
| WO | 2007015557 A1 | 2/2007 |
| WO | 2007066737 A1 | 6/2007 |
| WO | 2007090071 A2 | 8/2007 |
| WO | 2007093599 A1 | 8/2007 |
| WO | 2007085485 A3 | 9/2007 |

(56) References Cited

FOREIGN PATENT DOCUMENTS

| | | | |
|---|---|---|---|
| WO | 2007134181 A3 | 1/2008 |
| WO | 2008067825 A1 | 6/2008 |
| WO | 2008101157 A1 | 8/2008 |
| WO | 2008106186 A3 | 10/2008 |
| WO | 2008150729 A3 | 12/2008 |
| WO | 2008154401 A3 | 12/2008 |
| WO | 2009006478 A2 | 1/2009 |
| WO | 2009123216 A1 | 10/2009 |
| WO | 2009155102 A2 | 12/2009 |
| WO | 2010023670 A2 | 3/2010 |
| WO | 2010085495 A1 | 7/2010 |
| WO | 2011043385 A1 | 4/2011 |
| WO | 2011053065 A2 | 5/2011 |
| WO | 2011139699 A3 | 11/2011 |
| WO | 2012065086 A1 | 5/2012 |
| WO | 2012146628 A1 | 11/2012 |
| WO | 2015021432 A1 | 2/2015 |
| WO | 2015038426 A1 | 3/2015 |
| WO | 2015157555 | 10/2015 |
| WO | 2016025385 A1 | 2/2016 |
| WO | 2016115168 A1 | 7/2016 |
| WO | 2016164937 A3 | 1/2017 |
| WO | 2017106767 A1 | 6/2017 |
| WO | 2017112825 A2 | 6/2017 |
| WO | 2017223528 A1 | 12/2017 |
| WO | 2019014267 A1 | 1/2019 |
| WO | 2019028419 A1 | 2/2019 |
| WO | 2019028425 A1 | 2/2019 |
| WO | 2019165453 A1 | 8/2019 |
| WO | 2019173832 A2 | 9/2019 |
| WO | 2020020783 A1 | 1/2020 |
| WO | 2020056066 A1 | 3/2020 |
| WO | 2020097325 A1 | 5/2020 |
| WO | 2020146221 A1 | 7/2020 |
| WO | 2020163532 A1 | 8/2020 |
| WO | 2020201095 A1 | 10/2020 |
| WO | 2020219943 A1 | 10/2020 |
| WO | 2020252418 A2 | 12/2020 |
| WO | 2021030374 A1 | 2/2021 |
| WO | 2021030483 A1 | 2/2021 |
| WO | 2021030602 A1 | 2/2021 |
| WO | 2021030706 A1 | 2/2021 |
| WO | 2021041206 A1 | 3/2021 |
| WO | 2021050554 A1 | 3/2021 |
| WO | 2021091986 A1 | 5/2021 |
| WO | 2021093633 A1 | 5/2021 |
| WO | 2021133839 A1 | 7/2021 |
| WO | 2021140416 A2 | 7/2021 |
| WO | 2021263026 A1 | 12/2021 |
| WO | 2022076853 A1 | 4/2022 |
| WO | 2022076859 A1 | 4/2022 |
| WO | 2022174101 A1 | 8/2022 |
| WO | 2022256538 A1 | 12/2022 |
| WO | 2023122750 A1 | 6/2023 |
| WO | 2023137401 A1 | 7/2023 |

OTHER PUBLICATIONS

Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nelson et al., N3'—>PS' Oligodeoxyribonucleotide Phosphoramidates: A New Method of Synthesis Based on a Phosphoramidite Amine-Exchange Reaction, J Org Chem, vol. 62, pp. 7278-7287, 1997.
Neumann et al., Encoding multiple unnatural amino acids via evolution of a quadruplet-decoding ribosome, Nature, vol. 464(7287), pp. 441-444, 2010.
Nguyen et al. Genetic Encoding and Labeling of Aliphatic Azides and Alkynes in Recombinant Proteins via a Pyrrolysyl-tRNA Synthetase/tRNACUA Pair and Click Chemistry. JAGS 131:8720-8721 (2009).
Nicolini et al. The FAP-IL2v Immunocytokine is a Versatile Combination Partner for Cancer Immunotherapy. Poster (SITC 2018).
Nielsen et al., Sequence-selective recognition of DNA by strand displacement with a thymine-substituted polyamidem, Science, vol. 254, pp. 1497-1500, 1991.
Nordstrom et al. Characterization of bacteriophage T7 DNA polymerase purified to homogeneity by antithioredoxin immunoadsorbent chromatography. J Biol Chem 256:3112-3117(1981).
Oberhauser et al., Effective incorporation of 2'-O-methyl-oligoribonucleotides into liposomes and enhanced cell association through modification with thiocholesterol, Nucl. Acids Res., vol. 20, pp. 533-538, 1992.
Office Action issued in JP Application No. 2020-503039, May 17, 2022, 4 pages.
Office Action, Taiwan Application No. 107127148, Apr. 13, 2021.
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Ohtsuki et al. Unnatural base pairs for specific transcription. PNAS USA 98(9):4922-4925 (2001).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al., Locked nucleic acids: a promising molecular family for gene-function analysis and antisense drug development, Curr Opinion Mol Ther, vol. 3, pp. 239-243, 2001.
Osika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ostrov et al., Design, synthesis, and testing toward a 57-codon genome, Science, vol. 353(6301), pp. 819-822, 2016.
Owczarzy et al. Stability and mismatch discrimination of locked nucleic acid-DNA duplexes. Biochem. 50(43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N (7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
Parrish et al. Functional anatomy of a dsRNA trigger: differential requirement for the two trigger strands in RNA Interference. Mol Cell 6(5):1077-1087 (2000).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2014050423 International Search Report and Written Opinion dated Nov. 24, 2014.
PCT/US2015/025175 International Search Report and Written Opinion dated Oct. 13, 2015.
PCT/US2016/013095 International Search Report and Written Opinion dated Apr. 27, 2016.
PCT/US2018/041503 International Search Report and Written Opinion dated Nov. 7, 2018.
PCT/US2018/041509 International Search Report and Written Opinion dated Sep. 27, 2018.
PCT/US2018/045257 International Search Report and Written Opinion dated Nov. 21, 2018.
PCT/US2018/45257 Invitation to Pay Additional Fees dated Sep. 25, 2018.
PCT/US2018/45265 International Search Report and Written Opinion dated Nov. 30, 2018.

(56) References Cited

OTHER PUBLICATIONS

PCT/US2018/45265 Invitation to Pay Additional Fees dated Sep. 25, 2018.
Peyrottes et al., Oligodeoxynucleoside phosphoramidates (P-NH2): synthesis and thermal stability of duplexes with DNA and RNA targets, Nucleic Acids Res, vol. 24, pp. 1841-1848, 1996.
Pfannenstiel et al. A Novel, Individualized Xenograft Model of Cancer Immunotherapy and Tumor Growth Inhibition by ALKS 4230. Poster #P351 (SITC 2017).
Piccirilli et al. AC-nucleotide base pair: methylpseudouridine-directed incorporation of formycin triphosphate into RNA catalyzed by T7 RNA polymerase. Biochemistry 30(42):10350-10356 (1991).
Piccirilli et al. Enzymatic incorporation of a new base pair into DNA and RNA extends the genetic alphabet. Nature 343:33-37 (1990).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Ptacin et al., "Cytokine Conjugates for the Treatment of Autoimmune Diseases", U.S. Appl. No. 16/634,487, filed Jan. 27, 2020.
Quan et al. Circular polymerase extension cloning for high-throughput cloning of complex and combinatorial DNA libraries. Nat Protoc 6(2):242-251 (2011).
Rao et al., "High-affinity CD25-binding IL-2 mutants potently stimulate persistent T cell growth", Biochemistry, vol. 44, No. 31, Aug. 1, 2005, pp. 10696-10701.
Roessler et al. Cooperative interactions between the interleukin 2 receptor a and 13 chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1 :Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Saha et al., 5'-Methyl-DNA-A New Oligonucleotide Analog: Synthesis and Biochemical Properties, J Org Chem, vol. 60, pp. 788-789, 1995.
Saison-Behmoaras et al., Short modified antisense oligonucleotides directed against Ha-ras point mutation induce selective cleavage of the mRNA and inhibit T24 cells proliferation, EMBO J, vol. 10, pp. 1111-1118, 1991.
Sakaguchi et al. Immunologic self-tolerance maintained by activated T cells expressing IL-2 receptor alpha-chains (CD25). Breakdown of a single mechanism of self-tolerance causes various autoimmune diseases. J Immunol 155(3):1151-64 1995).
Acimovic et al. Molecular Evolution of the Equilibrative Nucleoside Transporter Family: Identification of Novel Family Members in Prokaryotes and Eukaryotes. Mol Biol Evol 12:2199-2210 (2002).
Acsadi et al. Human Dystrophin Expression in mdx Mice After Intramuscular Injection of DNA Constructs. Nature 352:815-818 (1991).
Adhikary et al. Adaptive Mutations Alter Antibody Structure and Dynamics During Affinity Maturation. Biochemistry 54(11):2085-93 (2015).
Agris. Decoding the genome: a modified view. Nucleic Acids Res 32:223-238 (2004).
Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).
Allen et al. Roles of DNA polymerase I in leading and lagging-strand replication defined by a high-resolution mutation footprint of ColE1 plasmid replication. Nucleic Acids Res. 39:7020-7033 (2011).

Alpert et al. ABRF 2003: Precipitation of Large, High-Abundance Proteins from Serum With Organic Solvents. Poster No. P111-W (10 pgs) (2003).
Ambrogell Yet al. Pyrrolysine is not hardwired fro cotranslational insertion at UAG condons. PNAS 104(9):3141-3146 (2007).
Amiri et al. Deep origin of plastid/parasite ATP/ADP translocases. J. Mol. Evol. 56:137-150 (2003).
Arenas-Ramirez et al. Improved cancer immunotherapy by a CD25-mimobody conferring selectivity to human interleukin-2. Sci Transl Med 8:367ra166 (2016).
Arie et al. Phylogenetic identification of n-alkane assimilating Candida yeasts based on nucleotide divergence in the 59 end of LSU rDNA gene. J Gen Appl Microbial. 46(5):257-262 (2000).
Ast et al. Diatom plastids depend on nucleotide import from the cytosol. PNAS USA 106:3621-3626 (2009).
Audia et al. Study of the five Rickettsia prowazekii proteins annotated as ATP/ADP translocases (Tic): Only Tlc1 transports ATP/ADP, while Tlc4 and T1c5 transport other ribonucleotides. J. Bacterial. 188:6261-6268 (2006).
Baba et al. Construction of *Escherichia coli* K-12 in-frame, single-gene knockout mutants: the Keio collection. Mol Syst Biol 2006. 0008 (2006).
Beigelman et al. Synthesis of 5'-C-Methyl-D-allo- & L-Talo-ribonucleoside 3'-0-Phosphoramidites & Their Incorporation into Hammerhead Ribozymes. Nucleosides and Nucleotides 14(3-5):901-905 (1995).
Bell et al., "Sustained in vivo signaling by long-lived IL-2 induces prolonged increases of regulatory T cells," Journal of Autoimmunity, vol. 56, pp. 66-80, 2014.
Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Berger et al. Stability and selectivity of unnatural DNA with five-membered-ring nucleobase analogues. J Am Chem Soc 124(7):1222-6 (2002).
Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28(15):2911-2914 (2000).
Betz et al. KlenTaq polymerase replicates unnatural base pairs by inducing a Watson-Crick geometry. Nat Chem Biol 8:612-614 (2012).
Betz et al., Structural insights into DNA replication without hydrogen bonds, J Am Chem Soc, vol. 135, pp. 18637-18643, 2013.
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Bohringer et al., Synthesis of 5'-deoxy-5'-methylphosphonate linked thymidine oligonucleotides, Tet Lett, vol. 34, pp. 2723-2726, 1993.
Bordo et al. Suggestions for "safe" residue substitutions in site-directed mutagenesis. J Mol Biol 217:721-729 (1991).
Boyman et al. Selective Stimulation of T Cell subsets with Antibody-Cytokine Immune Complexes. Science 311 :1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Braasch et al., Locked nucleic acid (LNA): fine-tuning the recognition of DNA and RNA, Chem Bio, vol. 8:1-7, 2001.
Branca. Rekindling cancer vaccines. Nat Biotechnol 34(10):1019-1025 (2016).
Brauns et al. Studies on Lignin and Related Compounds: XII. Methanol Lignin. Canadian Journal of Research 13b(1):28-34 (1935).
Cann et al. A heterodimeric DNA polymerase: Evidence that members of Euryarchaeota possess a distinct DNA polymerase. PNAS USA 95:14250 (1998).
Capone et al. Amber, ochre and opal suppressor tRNA genes derived from a human serine tRNA gene. EMBO J 4(1): 213-221 (1985).

(56) References Cited

OTHER PUBLICATIONS

Cariello et al. Fidelity of Thermococcus litoralis DNA polymerase (VentTM) in PCR determined by denaturing gradient gel electrophoresis Nucl Acid Res 19:4193-4198 (1991).
Carmenate et al. Human IL-2 Mutein with Higher Antitumor Efficacy Than Wild Type IL-2. Journal of Immunology 190(12):6230-6238 (Jun. 15, 2013). Epub May 15, 2013.
Cassell et al., "Therapeutic Enhancement of IL-2 Through Molecular Design," Current Pharmaceutical Design, vol. 8, No. 24, pp. 2171-2183, 2002.
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Charych et al. Modeling the receptor pharmacology, pharmacokinetis, and pharmacodynamics of NKTR-214, a kinetically-controlled interleukin-2 (IL2) receptor agonist for cancer immunotherapy. PLoS One 12(7):e0179431 (2017).
Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).
Chastgner et al. Lack of intermediate-affinity interleukin-2 receptor in mice leads to dependence on interkeukin-2 receptor a,13 and y chain expression for T cell growth. Eur J Immunol 26:201-206 (1996).
Chatterjee et al. A Versatile Platform for Single- and Multiple-Unnatural Amino Acid Mutagenesis in *Escherichia coli*. Biochemistry 52(10):1828-1837 (2013).
Chaturvedi et al., Stabilization of triple-stranded oligonucleotide complexes: use of probes containing alternating phosphodiester and stereo-uniform cationic phosphoramidate linkages, Nucleic Acids Res., vol. 24, pp. 2318-2323, 1996.
Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. The expanding world of DNA and RNA. Curr Opin Chem Biol 34:80-87 (2016).
Chen et al., Phosphonate Analogues of Cytosine Arabinoside Monophosphate, Phosphorus, Sulfur and Silicon, vol. 177, pp. 1783-1786, 2002.
Chen et al., Selective chemical labeling of proteins, Org. Biomol. Chem., vol. 14, p. 5417, 2016.
Chien et al. Deoxyribonucleic acid polymerase from the extreme thermophile Thermus aquaticus. J Bacteriol 127:1550-1557 (1976).
Emerson et al., "NMR Characterization of Interleukin-2 in Complexes with the IL-2R Receptor Component, and with Low Molecular Weight Compounds that Inhibit the IL-2/IL-R interaction", Protein Science, vol. 12 (Dec. 31, 2003).
Ghelani et al., "Defining the Threshold IL-2 Signal Required for Induction of Selective Treg Cell Responses Using Engineered IL-2 Muteins", Frontiers in Immunology, vol. 11, Article 1106, figure 2, (Jun. 30, 2020).
Lawrence et al. "How PEGylation influences protein conformational stability", Current Opinion in Chemical Biology, Current Biology Ltd, London, GB, vol. 34, pp. 88-94 (Aug. 28, 2016).
Levin et al., "Exploiting a Natural Conformational Switch to Engineer an Interleukin-2 Superkine", Nature, vol. 484, No. 7359, (Apr. 26, 2012).
Mei et al., "Site-Mutation of Hydrophobic Core Residues Synchronically Poise Super Interleukin 2 for Signaling: Identifying Distant Structural Effects through Affordable Computations", International Journal of Molecular Science, vol. 19, No. 3, Article 916 (Mar. 20, 2018).
Prometheus Laboratories Inc., FDA Label for Proleukin (Aldesleukin), 19 pages (2011).
Ptacin et al., "A CD25-biased interleukin-2 for autoimmune therapy engineered via a semi-synthetic organism", Communications Medicine, 4:58, pp. 1-16, (2024).
Rao et al., "Interleukin-2 Mutants with Enhanced A-Receptor Subunit Binding Affinity", Protein Engineering, vol. 16, No. 12, (Dec. 31, 2003).
Aerni et al., Co-pending U.S. Appl. No. 17/845,495, filed Jun. 21, 2022; also cited herein as US Publication No. US 20220324792.
Caffaro et al., Co-pending U.S. Appl. No. 17/735,564, filed May 3, 2022; also cited herein as US Publication No. US 20220273767.
Ptacin et al., Co-pending U.S. Appl. No. 18/327,535, filed Jun. 1, 2023.
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. Sci BX 3(27):2 pgs (2010).
Ludwig et al. Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Lyon et al. Self-hydrolyzing maleimides improve the stability and pharmacological properties of antibody-drug conjugates. Nat. Biotechnol. 32(10):1059-1062 (2014).
Malyshev et al. PCR with an Expanded Genetic Alphabet. JACS 131 (41):14620-14621 (2009).
Malyshev et al. Solution structure, mechanism of replication, and optimization of an unnatural base pair. Chem Eur J16:12650-12659 (2010).
Malyshev et al. The expanded genetic alphabet. Angew Chem Int Ed Engl 54:11930-11944 (2015).
Malyshev et al., A semi-synthetic organism with an expanded genetic alphabet, Nature, vol. 509(7500), pp. 385-388, 2014.
Malyshev et al., Efficient and sequence-independent replication of DNA containing a third base pair establishes a functional six-letter genetic alphabet, PNAS USA, vol. 109, pp. 12005-12010, 2012.
Manoharan et al., Chemical Modifications to Improve Uptake and Bioavailability of Antisense Oligonucleotides, Ann N.Y. Acad. Scie, vol. 660, pp. 306-309, 1992.
Manoharan et al., Cholic Acid-Oligonucleotide Conjugates for Antisense Applications, Bioorg. Med. Chem. Let., vol. 4, pp. 1053-1060, 1994.
Manoharan et al., Introduction of a Lipophilic Thioether in the Minor Groove of Nucleic Acids for Antisense Applications, Bioorg. Med. Chem. Let., vol. 3, pp. 2765-2770, 1993.
Manoharan et al., Lipidic Nucleic Acids, Tetrahedron Lett, vol. 36, pp. 3651-3654, 1995.

(56) References Cited

OTHER PUBLICATIONS

Manoharan et al., Oligonucleotide Conjugates: Alteration of the Pharmacokinetic Properties of Antisense Agents, Nucleosides & Nucleotides, vol. 14, pp. 969-973, 1995.
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci, Oligonucleotide Analogs: an Overview, Oligonucleotides as therapeutic agents, Chadwick and Cardew ed., Ciba Foundation Symposium 209, pp. 5-18, 1997.
McMinn et al. Efforts toward Expansion of the Genetic Alphabet: DNA Polymerase Recognition of a Highly Stable, Self-Pairing Hydrophobic Base. J. Am. Chem. Soc. 121 :11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15RI3/yc Receptor. J Immunol 198(12):4563-4568 (2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Meyers et al. Optimal alignments in linear space. CABIOS 4:11-17 (1989).
Micklefield, Backbone Modification of Nucleic Acids: Synthesis, Structure and Therapeutic Applications, Current Medicinal Chemistry, vol. 8, pp. 1157-1179, 2001.
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al., Substrate Properties of C'-Methylnucleoside and C'-Methyl-2'-deoxynucleoside 5'-Triphosphates in RNA and DNA Synthesis Reactions Catalysed by RNA and DNA Polymerases, Nucleosides & Nucleotides, vol. 10(1-3), pp. 339-343, 1991.
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al., Conformation and interaction of dinucleoside mono- and diphosphates. V. Syntheses and properties of adenine and thymine nucleoside alkyl phosphotriesters, the neutral analogs of dinucleoside monophosphates, JAGS, vol. 93, pp. 6657-6665, 1971.
Miroux et al. Over-production of proteins in *Escherichia coli*: mutant hosts that allow synthesis of some membrane proteins and globular proteins at high levels. J Mol Biol 260:289-298 (1996).
Mishra et al., Improved leishmanicidal effect of phosphorotioate antisense oligonucleotides by LDL-mediated delivery, Biochem Biophys Acta, vol. 1264, pp. 229-237, 1995.
Montero et al. Nucleosides de synthese XVI: Sur une synthese selective de divers ribofuranosyl-1-purines. Journal of Heterocyclic Chemistry 15(6):929-935 (1978) (English Abstract).

Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mullis et al. Specific enzymatic amplification of DNA in vitro the polymerase chain reaction. Cold Spring Harbor Symp. Quant. Biol. 51 :263 (1986).
Myers et al. Reverse transcription and DNA amplification by a Thermus thermophilus DNA polymerase. Biochemistry 30:7661-7666 (1991).
Nakazawa et al. UV and skin cancer: specific p53 gene mutation in normal skin as a biologically relevant exposure measurement. PNAS USA 91 (1):360-364 (1994).
Napolitano et al., Emergent rules for codon choice elucidated by editing rare argine codons in *Escherichia coli*, PNAS, vol. 113(38), pp. 5588-5597, 2016.
National Institute of Cancer-understanding and related topics. Accessed Aug. 18, 2019 at URL: https://www.cancer.gov/about-cancer/ understanding/what-is-cancer (9 pgs).
Nawrot et al., A novel class of DNA analogs bearing 5'-C-phosphonothymidine units: synthesis and physicochemical and biochemical properties, Oligonucleotides, vol. 16(1), pp. 68-82, 2006.
Fersht. Enzyme Structure and Mechanism, 2nd ed., W. H. Freeman & Co., New York (pp. 350-351) (1985).
Fidanza et al. Site-specific labeling of DNA sequences containing phosphorothioate diesters. JAGS 114(14):5509-5517 (2002).
Fisher et al. Chlamydia trachomatis Transports NAD via the Npt1 ATP/ADP Translocase. Journal of Bacteriology 195(15):3381-3386 (2013).
Fi Danza et al. Functionalization of oligonucleotides by the incorporation of thio-specific reporter groups. In Protocols for Oligonucleotide Conjugates. Protocols for Oligonucleotide Conjugates: Synthesis and Analytical Techniques 26:121-143 (1994).
Floros et al. Anticancer Cytokines: Biology and Clinical Effects of Interferon-a2, Interleukin (IL)-2, IL-15, IL-21, and L-12. Semin Oncol 42(4):539-548 (2015).
Fourrey et al. Photo Rearrangement of Phenyl Selenide Derivatives Access to Selenium Substituted C Nucleosides. Tetrahedron Letters 21 :455-458 (1980).
Friedhoff et al. Quantitative polymerase chain reaction with oligodeoxynucleotide ligation assay/enzyme-linked mmunosorbent assay detection. Anal Biochem 215(1):9-16 (1993).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of 13-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Gong et al., Recent advances in bioorthogonal reactions for site-specific protein labeling and engineering, Tetrahedron Letters, vol. 56, pp. 2123-2131, 2015.
Goodman. Error-prone repair DNA polymerases in prokaryotes and eukaryotes. Annu. Rev. Biochem. 71:17-50 (2002).
Guatelli et al. Isothermal, in vitro amplification of nucleic acids by a multienzyme reaction modeled after retroviral replication. PNAS USA 87(5):1874-1878 (1990).

(56) References Cited

OTHER PUBLICATIONS

Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbial. 60:1534-1545 (2006).
Hampton et al., Design of substrate-site-directed inhibitors of adenylate kinase and hexokinase. Effect of substrate substituents on affinity on affinity for the adenine nucleotide sites, J Med Chem, vol. 19, pp. 1371-1377, 1976.
Hampton et al., Design of substrate-site-directed irreversible inhibitors of adenosine 5'-phosphate aminohydrolase. Effect of substrate substituents on affinity for the substrate site, J Med Chem, vol. 19(8), pp. 1029-1033, 1976.
Hampton et al., Synthesis of 6'-cyano-6'-deoxyhomoadenosine-6'-phosphonic acid and its phosphoryl and byrophosphoryl an hydrides and studies of their interactions with adenine nucleotide utilizing enzymes, J Am Chem Soc, vol. 95(13), pp. 4404-4414, 1973.
Hancock et al. Expanding the Genetic Code of Yeast for Incorporation of Diverse Unnatural Amino Acids via a Pyrrolysyl-tRNA Synthetase/tRNA Pair. JAGS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer Immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Hinnisdaels et al. Direct cloning of PCR products amplified with Pwo DNA polymerase. Biotechniques 20:186-188 (1996).
Hirao et al. An unnatural base pair between imidazolin-2-one and 2-amino-6-(2-thienyl)purine in replication and transcription. Nucleic Acids Res Suppl. 2(1):37-38 (2002).
Hirao et al., Unnatural base pair systems toward the expansion of the genetic alphabet in the central dogma. Proceedings of the Japan Academy, Series B, Phys Biol Sci. 88:345-367 (2012).
Horn et al. Bacterial endosymbionts of free-living amoebae. J. Eukaryot. Microbial. 5:509-514 (2004).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al., From Phosphate to Bis(methylene) Sulfone: Non-Ionic Backbone Linkers in DNA, Helvetica Chimica Acta, vol. 85, pp. 2777-2806, 2002.
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and salvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Imran et al. Influence of architecture of high molecular weight linear and branched poly glycerolspolyglycerols on their biocompatibility and biodistribution. Biomaterials 33:9135-914 7 (2012).
INSIGHT-ESPRIT Study Group et al. Interleukin-2 Therapy in Patients with HIV Infection. N Engl J Med. 361(16):1548-59 (2009).
Ishizuka et al. Site-specific functionalization of RNA molecules by an unnatural base pair transcription system via click chemistry. Chem. Comm. 48:10835-10837 (2012).
Jager et al., Oligonucleotide N-alkylphosphoramidates: synthesis and binding to polyn ucleotides, Biochemistry, vol. 27, pp. 7247-7246, 1988.
Jiang et al. Role of IL-2 in cancer immunotherapy. Oncoimmunology 5(6):e1163462 (2016).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Abbadessa et al., Co-pending U.S. Appl. No. 18/524,157, filed Jul. 11, 2024; also cited herein as US 2024/0226309.
Alvarez et al., "The IL-2 Synthorin molecule promotes functionally adapted Tregs in a preclinical model of type 1 diabetes", JCI Insight, 9(24) (2024).
Caffaro et al., Co-pending U.S. Appl. No. 18/296,710, filed Apr. 6, 2023; also cited herein as US 2023/0277627.
Caffaro et al., Co-pending U.S. Appl. No. 18/296,711, filed Apr. 6, 2023; also cited herein as US 2023/0416327.
Caffaro et al., Co-pending U.S. Appl. No. 18/415,445, filed Jan. 17, 2024; also cited herein as US 2024/0287151.
Caffaro et al., Co-pending U.S. Appl. No. 18/424,573, filed Jan. 26, 2024.
Ptacin et al., Co-pending U.S. Appl. No. 18/886,814, filed Sep. 16, 2024.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,219 Office Action dated Aug. 22, 2019.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Vazquez-Lomardi et al., "Potent antitumour activity of interleukin-2-Fc fusion proteins requires Fc-mediated depletion of regulatory T-cells", Nature Communications, vol. 8, May 12, 2017.

(56) References Cited

OTHER PUBLICATIONS

Verma. Retroviral vectors for gene transfer. In: Microbiology (Leive Let al., eds., Ann. Soc. Microbial) American Society of Microbiology, Washington, DC, p. 229-232 (1985).
Verma. The reverse transcriptase. Biochim Biophys Acta. 473:1-38 (1977).
Vrudhula et al., Isozyme-specific enzyme inhibitors. 13. S-[5'(R)-[(N-triphosphoamino)methyl]adenosyl]-L-homocysteine, a potent inhibitor of rat methionine adenosyltransferases, J Med Chem, vol. 30, pp. 888-894, 1987.
Wahlestedt et al., Potent and nontoxic antisense oligonucleotides containing locked nucleic acids, PNAS USA, vol. 97, pp. 5633-5638, 2000.
Waldmann et al. The Shared and Contrasting Roles of IL2 and IL 15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wan et al. Pyrrolysyl- tRNAPyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its a, ls, and ye Receptors. Science 310:1159-63 (2005).
Wang et al., Biophysical and biochemical properties of oligodeoxy-nucleotides containing 4'-C-and 5'-C-substituted thymidines, Bioorg Med Chem Lett, vol. 9, pp. 885-890, 1999.
Wang et al., Synthesis of Azole Nucleoside 5'-Monophosphate Mimics (P1 Ms) and Their Inhibitory Properties of IMP Dehydrogenases, Nucleosides Nucleotides & Nucleic Acids, vol. 23(1 & 2), pp. 317-337, 2004.
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Reverse transcriptase. CRC Grit Rev Biochem 3:289-347 (1975).
Wu et al. Synthesis of Site-Specific Radiolabeled Antibodies for Radioimmunotherapy via Genetic Code Expansion. Bioconjugate Chem. 27:2460-2468 (2016).
Wu et al., Functionalization of the sugar moiety of oligoribonucleotides on solid support, Bioconjugate Chem, vol. 10, pp. 921-924, 1999.
Wu et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, vol. 83, pp. 1127-1143, 2000.
Wurm et al. Squaric acid mediated synthesis and biological activity of a library of linear and hyperbranched poly (glycerol)-protein conjugates. Biomacromolecules 13: 1161-1171 (2012).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J mmunol 145:873-877 (1990).
Yamashige et al. Highly specific unnatural base pair systems as a third base pair for PCR amplification. Nucleic Acids Res. 40:2793-2806 (2012).
Yan et al. Nucleoside monophosphate kinases: structure, mechanism, and substrate specificity. Adv. Enzymol. Relat. Areas Mol. Biol. 73:103-134 (1999).
Young et al., Beyond the canonical 20 amino acids: expanding the genetic lexicon, J Biol Chem, vol. 285, pp. 11039-11044, 2010.
Yu et al. Polymerase recognition of unnatural base pairs. Angew Chem Int Ed Engl 41 (20):3841-4 (2002).
Zalevsky. Jefferies 2016 Global Healthcare Conference. PowerPoint presentation (Nov. 16, 2016).
Zhang et al. Semisynthetic Organisms with Expanded Genetic Codes. Biochemistry 57:2177-2178 (20180.
Zhang et al. Studies of nucleoside transporters using novel autofluorescent nucleoside probes. Biochemistry 45(4):1087-1098 (2006).
Zhang et al., "Site-specific PEGylation of interleukin-2 enhances immunosuppression via the sustained activation of regulatory T cells," Nature Biomed. Engin., 5: 1288-1305 (2021).
Zhang et al., A semisynthetic organism engineered for the stable expansion of the genetic alphabet, PNAS USA, vol. 114(6), pp. 1317-1322, 2017.
Zhang et al., A Semi-Synthetic Organism that Stores and Retrieves Increased Genetic Information, Nature, vol. 551 (7682), pp. 644-647, 2017.
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon, Chapter 8: Oligonucleotide Phosphorothioates in Protocols for Oligonucleotides and Analogs, Synthesis and Properties. Humana Press, pp. 165-190, 1993.
Cleary et al. Production of complex nucleic acid libraries using highly parallel in situ oligonucleotide synthesis. Nat Methods 1 (3):241-248 (2004).
Collingwood et al., The Synthesis and Incorporation in Oligonucleotides of a Thymidine Dimer Containing an Internucleoside Phosphinate Linkage, Synlett vol. 7, pp. 703-705, 1995.
Co-pending U.S. Appl. No. 16/634,487, filed Jan. 27, 2020 also cited herein as US Publication No. 20200231644.
Co-pending U.S. Appl. No. 16/803,816, filed Feb. 27, 2020 also cited herein as US Publication No. 20200188484.
Co-pending U.S. Appl. No. 16/993,967, filed Aug. 14, 2020 also cited herein as US Publication No. 20210046160.
Co-pending U.S. Appl. No. 16/999,638, filed Aug. 21, 2020 also cited herein as US Publication No. 20210054040.
Co-pending U.S. Appl. No. 17/001,965, filed Aug. 25, 2020 also cited herein as US Publication No. 20200399338.
Co-pending U.S. Appl. No. 17/016,003, filed Sep. 9, 2020 also cited herein as US Publication No. 20210070827.
Co-pending U.S. Appl. No. 17/313,579, filed May 6, 2021.
Co-pending U.S. Appl. No. 17/350,672, filed Jun. 17, 2021.
Co-pending U.S. Appl. No. 17/357,615, filed Jun. 24, 2021.
Co-pending U.S. Appl. No. 16/413,209, filed May 15, 2019.
Co-pending U.S. Appl. No. 16/413,219, filed May 15, 2019.
Co-pending U.S. Appl. No. 16/518,715, filed Jul. 22, 2019.
Co-pending U.S. Appl. No. 16/530,742, filed Aug. 2, 2019.
Co-pending U.S. Appl. No. 16/535,992, filed Aug. 8, 2019.
Crooke et al., Pharmacokinetic properties of several novel oligonucleotide analogs in mice, J Pharmacol Exp Ther, vol. 277, pp. 923-937, 1996.
Dahl et al. Discovery and validation of a series of aryl sulfonamides as selective inhibitors of tissue-nonspecific alkaline phosphatase (TNAP). J Med Chem 52(21):6919-6925 (2009).
De Mesmaeker et al., Amide-Modified Oligonucleotides with Preorganized Backbone and Furanose Rings: Highly Increased Thermodynamic Stability of the Duplexes Formed with their RNA and DNA Complements, Synlett, vol. 11, pp. 1287-1290, 1997.

(56) References Cited

OTHER PUBLICATIONS

Deiters et al. Site-specific PEGylation of proteins containing unnatural amino acids. Bioog Med Chem Lett 14:57 43-57 45.
Dhami et al., Systematic exploration of a class of hydrophobic unnatural base pairs yields multiple new candidates for the expansion of the genetic alphabet, Nucleic Acids Res, vol. 42, pp. 10235-10244, 2014.
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al., Progress Toward a Semi-Synthetic Organism with an Unrestricted Expanded Genetic Alphabet, J Am Chem Soc., vol. 140, pp. 16115-16123, 2018.
Dozier et al. Site-Specific PEGylation of Therapeutic Proteins, Int. J Mol Sci. Oct. 2015; 16(10): 25831-25864.
Dranoff. Cytokines in cancer pathogenesis and cancer therapy. Nature Reviews Cancer 4:11-22 (2004).
Dufour. THOR-707, an engineered not-alpha IL-2, for the treatment of solid tumors induces strong immunological responses in vivo. CSCO Immunotherapy Seminar Mar. 22-23, 2019 Shanghi, China (12 pgs).
Dumas et al., Designing logical codon reassignment-Expanding the chemistry in biology, Chem Sci, vol. 6, pp. 50-69, 2015.
Dupradeau et al. Differential salvation and tautomer stability of a model base pair within the minor and major grooves of DNA. J Am Chem Soc 127(44):15612-7 (2005).
Eggertsson et al. Transfer ribonucleic acid-mediated suppression of termination codons in *Escherichia coli*. Microbial Rev 52(3):354-374 (1988).
Egholm et al. PNA hybridizes to complementary oligonucleotides obeying the Watson-Crick hydrogen-bonding rules. Nature 365(6446):566-568 (1993).
El Yacoubi et al. Biosynthesis and function of posttranscriptional modifications of transfer RNAs. Annu Rev Genet 46:69-95 (2012).
Elayadi et al., Application of PNA and LNA oligomers to chemotherapy, Curr Opinion Invens Drugs, vol. 2, pp. 558-561, 2001.
Ellington et al. In vitro selection of RNA molecules that bind specific ligands. Nature 346:818-822 (1990).
Enablement Decision Tree, Example F, situation 1. http://www.uspto.gov/web/offices/pac/dapp/1 pecba.htnn#7>. accessed Aug. 18, 19 (72 pgs).
Engleerg-Kukla et al. Chapter 60: Suppression of Termination Codons. *Escherichia coli* and *Salmonella* Cellular and Molecular Biology (pp. 909-921) (1996).
Englisch et al., Chemically Modified Oligonucleotides as Probes and Inhibitors, Angew. Chem. Int. Ed. Eng., vol. 30, pp. 613-629, 1991.
Eppacher et al., Synthesis and Incorporation of C(5 ')-Ethynylated Uracil-Derived Phosphoramidites into RNA, Helvetica Chimica Acta, vol. 87, pp. 3004-3020, 2004.
Extended European Search Report, European Patent Application No. 18840563.3, 9 pages, Apr. 28, 2021.
Fa et al. Expanding the substrate repertoire of a DNA polymerase by directed evolution. J Am Chem Soc 126(6):1748-54 (2004).

Fairhurst et al., Synthesis and Hybridisation Properties of Phosphonamidate Ester Modified Nucleic Acid, Synlett, vol. 4, pp. 467-472, 2001.
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. Optimization of Replication, Transcription, and Translation in a Semi-Synthetic Organism. J Am Chem Soc 141:10644-10653 (2019).
Feldman et al., In Vivo Structure-Activity Relationships and Optimization of an Unnatural Base Pair for Replication in a Semi-Synthetic Organism, J Am Chem Soc, vol. 139, pp. 11427-11433, 2017.
Feldman. Expansion of the Genetic Alphabet: A Chemist's Approach to Synthetic Biology. Ace Chem Res 51(2):394-403 (2018).
Juncosa-Ginesta et al. Improved efficiency in site-directed mutagenesis by PCR using a *Pyrococcus* sp. GB-D polymerase. Biotechniques 16:820-823 (1994).
Jung et al., Synthesis of phosphonate derivatives of uridine, cytidine, and cytosine arabinoside, Bioorg Med Chem, vol. 8, pp. 2501-2509, 2000.
Kabanov et al., A new class of antivirals: antisense oligonucleotides combined with a hydrophobic substituent effectively inhibit influenza virus reproduction and synthesis of virus-specific proteins in MOCK cells, FEBS Lett vol. 259, pp. 327-330, 1990.
Kandimalla et al., Effect of chemical modifications of cytosine and guanine in a CpG-motif of oligonucleotides: structure-immunostimulatory activity relationships, Bioorg. Med. Chem., vol. 9, pp. 807-813, 2001.
Kappler et al., Isozyme-specific enzyme inhibitors. 11. L-homocysteine-ATP S-C5' covalent adducts as inhibitors of rat methionine adenosyltransferases, J Med Chem, vol. 29, pp. 1030-1038, 1986.
Kappler et al., Species- or isozyme-specific enzyme inhibitors. 8. Synthesis of disubstituted two-substrate condensation products as inhibitors of rat adenylate kinases, J Med Chem, vol. 25, pp. 1179-1184, 1982.
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Kim et al. Stability and polymerase recognition of pyridine nucleobase analogues: role of minor-groove H-bond acceptors. Angew Chem Int Ed Engl 45(46):7809-12 (2006).
Kimoto et al. Generation of high-affinity DNA aptamers using an expanded genetic alphabet. Nat. Biotech. 31(5):453-458 (2013).
Kivimae et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimae et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based Immunocytokines. Oncoimmunology 6(3):e1277306 (2017).
Knab et al. Nucleotide parasitism by Simkania negevensis (Chlamydiae). J. Bacterial. 193:225-235 (2011).
Koshkin et al., LNA (locked nucleic acids): synthesis of the adenine, cytosine, guanine 5-methylcytosine, thymine and uracil bicyclonucleoside monomers, oligomerisation, and unprecedented nucleic acid recognition, Tetrahedron, vol. 54(14), pp. 3607-3630, 1998.

(56) References Cited

OTHER PUBLICATIONS

Kranaster et al. Increased single-nucleotide discrimination in allele-specific polymerase chain reactions through primer probes bearing nucleobase and 2'-deoxyribose modifications. Chem EurJ 13(21):6115-6122 (2007).
Krieg et al. Improved IL-2 immunotherapy by selective stimulation of IL-2 receptors on lymphocytes and endothelial cells. PNAS USA 107:11906-11911 (2010).
Kroschwitz, The Concise Encyclopedia of Polymer Science and Engineering, Ed., John Wiley & Sons, pp. 858-859, 1990.
Kroschwitz. The Concise Encyclopedia of Polymer Science and Engineering. (pp. 858-859) (1990).
Kubelka et al. Synthesis of 2,6-disubstituted pyridin-3-yl C-2'-deoxyribonucleosides through chemoselective transformations of bromo-chloropyridine C-nucleosides. Org. Biomol. Chem. 11:4702-4718 (2013).
Kumar et al., The First Analogues of LNA (Locked Nucleic Acids): Phosphorothioate LNA and 2'-Thio-LNA, Bioorg Med Chem Lett, vol. 8, pp. 2219-2222, 1998.
Kutyavin. Use of base-modified duplex-stabilizing deoxynucleoside 5'-triphosphates to enhance the hybridization properties of primers and probes in detection polymerase chain reaction. Biochemistry 4 (51):13666-13673 (2008).
Kwoh et al. Transcription-based amplification system and detection of amplified human immunodeficiency virus type 1 with a bead-based sandwich hybridization format. Pnas USA 86:1173-1177 (1989).
Landy. Mechanistic and structural complexity in the site-specific recombination pathways of Int and FLP. Curr Opin Genet Dev. 3(5):699-707 (1993).
Langowski et al. The CD122-biased immunostimulatory cytokine NKTR-214 combined with checkpoint blockade eads to mobilization of anti-tumor immunity and synergistic activity. Poster Abstract 311. 2016 CR-CIMT-EATIR-AACR Cancer Immunotherapy Conference (2016).
Lavergne et al. FRET Characterization of Complex Conformational Changes in a Large 16S Ribosomal RNA Fragment Site-Specifically Labeled Using Unnatural Base Pairs. ACS Chem Biol 11 (5): 1347-53 (2016).
Lavergne et al. Major groove substituents and polymerase recognition of a class of predominantly hydrophobic unnatural base pairs. Chem. Eur. J. 18:1231-1239 (2012).
Lavergne et al., Expanding the scope of replicable unnatural DNA: Stepwise optimization of a predominantly hydrophobic base pair, JAGS, vol. 135, pp. 5408-5419, 2013.
Lazear et al. Targeting of IL-2 to cytotoxic lymphocytes as an improved method of cytokine-driven immunotherapy. Oncoimmunology 6(2):e1265721 (2017).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127 (36): 12470-1 (2005).
Leconte et al. Selective Inactivation of the 3' to 5' exonuclease activity of *Escherichia coli* DNA polymerase I by heat. Nucl Acids Res 11 :7505-7515 (1983).
Ledbetter et al. Editorial overview: Expanding the genetic alphabet and code. Curr Opin Chem Biol 46:A1-A2 (2018).
Ledbetter et al. Site-Specific Labeling of DNA via PCR with an Expanded Genetic Alphabet. Methods Mol Biol 1973:193-212 (2019).
Ledbetter et al., Reprograming the Replisome of a Semisynthetic Organism for the Expansion of the Genetic Alphabet, J Am Chem Soc, vol. 140, pp. 758-765, 2018.
Letourneau et al. IL-2/anti-IL-2 antibody complexes show strong biological activity by avoiding interaction with IL-2 receptor alpha subunit CD25. PNAS USA 107:2171-2176 (2010).
Letsinger et al., Cholesteryl-conjugated oligonucleotides: Synthesis, properties, and activity as inhibitors of replication of human immunodeficiency virus in cell culture, PNAS, vol. 86, pp. 6553-6556, 1989.
Levin et al. Exploiting a natural conformational switch to engineer an Interleukin-2 superkine. Nature 484 (7395):529-533 (Mar. 25, 2012). doi:10.1038/nature10975.
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Li et al. Synthesis of linear polyether polyol derivatives as new materials for bioconjugation. Bioconjugate ChemChem 20:780-789 (2009).
Liu et al. Adding new chemistries to the genetic code. Annu Rev Biochem 79:413-444 (2010).
Lizardi et al. Exponential amplification of recombinant-RNA hybridization probes. Nature Biotechnology 6:1197-1202 (1988).
Sanghvi. Chapter 15: Heterocyclic Base Modifications in Nucleic Acids and Their Applications in Antisense Oligonucleotides. Antisense Research and Applications, Crooke and Lebleu Eds., CRC Press (pp. 273-288) (1993).
Sauer. Site-specific recombination: developments and applications. Curr Opin Biotechnol 5(5):521-527 (1994).
Schmied et al. Efficient Multisite Unnatural Amino Acid Incorporation in Mammalian Cells via Optimized Pyrrolysyl RNA Synthetase/tRNA Expression and Engineered eRF1. JAGS 136:15577-15583 (2014).
Schultz et al., Oligo-2'-fluoro-2'-deoxynucleotide N3'— > PS' phosphoramidates: synthesis and properties, Nucleic Acids Res, vol. 24, pp. 2966-2973, 1996.
Search Report, Taiwan Application No. 107127148, Apr. 12, 2021.
Seo et al. Improved High-Efficiency Organic Solar Cells via Incorporation of a Conjugated Polyelectrolyte Interlayer. JAGS 133:8416-8419 (2011).
Seo et al. Major groove derivatization of an unnatural base pair. Chembiochem 10(14):2394-2400 (2009).
Seo et al. Optimization of an unnatural base pair toward natural-like replication. J Am Chem Soc 131 :3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JAGS 131 (14):5046-5047 (2009).
Shaloiko et al. Effective non-viral leader for cap-independent translation in a eukaryotic cell-free system. Biotechnology and Bioengineering 88(6):730-739 (2004).
Shanafelt et al., "A T-cell-selective interleukin 2 mutein exhibits potent antitumor activity and is well tolerated in vivo," Nature Biotechnology, vol. 18, No. 11, pp. 1197-1202, 2000.
Sharma et al. NKTR-214 enhances anti-tumor T cell immune responses induced by checkpoint blockade or vaccination. Poster (SITC 2017).
Shea et al. Synthesis, hybridization properties and antiviral activity of lipid-oligodeoxynucleotide conjugates. Nucl. Acids Res 18:3777-3783 (1990).
Shimizu et al. Cell-free translation systems for protein engineering. FEBS J 273:4133-4140 (2006).

(56) References Cited

OTHER PUBLICATIONS

Sierzputowska-Gracz et al. Chemistry and structure of modified uridines in the anticodon, wobble position of transfer RNA are determined by thiolation. J Am Chem Soc 109:7171-7177 (1987).
Sim et al. IL2 Variant Circumvents ICOS+ Regulatory T-cell Expansion and Promotes NK Cell Activation. Cancer Immunol Res. 4(11):983-995 (2016).
Singh et al., LNA (locked nucleic acids): synthesis and high-affinity nucleic acid recognition, Chem Commun, vol. 4, pp. 455-456, 1998.
Singh et al., Synthesis of 2'-amino-LNA: A novel conformationally restricted high-affinity oligonucleotide analogues with a handle, J Bio Chem, vol. 63, pp. 10035-10039, 1998.
Sivakumar et al. Comparison of Vascular Leak Syndrome in Mice treated with IL21 or IL2. Comparative Medicine 63(1 ):13-21 (2013).
Slagle et al. Click Conjugation of Cloaked Peptide Ligands to Microbubbles. Bioconjug Chem 29(5):1534-1543 (2018).
Sockolosky et al. Selective targeting of engineered T cells using orthogonal IL-2 cytokine-receptor complexes. Science 359(6379):1037-1042 (Mar. 2, 2018).
Southern et al. Transformation of mammalian cells to antibiotic resistance with a bacterial gene under control of the SV40 early region promoter. J Mol Appl Genet 1 :327-341 (1982).
Spangler et al. Antibodies to Interleukin-2 Elicit Selective T Cell Subset Potentiation through Distinct Conformational Mechanism. Immunity 42:815-825 (2015).
Srivastava et al., Five- and six-membered conformationally locked 2',4'-carbocyclic ribo-thymidines: synthesis, structure, and biochemical studies, J Am Chem Soc, vol. 129(26), pp. 8362-8379, 2007.
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sun et al. First-In-Human dose Selection of ALKS 4230, an Investigational Immunotherapeutic Agent. Poster 4088 AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Svinarchuk et al., Inhibition of HIV proliferation in MT-4 cells by antisense oligonucleotide conjugated to lipophilic groups, Biochimie, vol. 75, pp. 49-54, 1993.
Switzer et al. Enzymatic recognition of the base pair between isocytidine and isoguanosine. Biochemistry 32(39):10489-10496 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under The Securities Act of 1933 filed Nov. 27, 2018 (355 pgs.).
T Jalsma et al. Signal peptide-dependent protein transport in Bacillus subtilis: a genome-based survey of the secretome. Microbial Mol Biol Rev 64(3):515-547 (2000).
Tae et al. Efforts toward expansion of the genetic alphabet: replication of DNA with three base pairs. J. Am. Chem. Soc. 123:7439-7440 (2001).
Takagi et al. Characterization of DNA polymerase from *Pyrococcus* sp. strain KOD1 and its application to PCR. Appl Environ Microbiol 63(11):4504-4510 (1997).
Takai et al. A single uridine modification at the wobble position of an artificial RNA enhances wobbling in an *Escherichia coli* cell-free translation system. FEBS Lett 447(1):1-4 (1999).
Tapp et al. Homogeneous scoring of single-nucleotide polymorphisms: comparison of the 5'-nuclease TaqMan assay and Molecular Beacon probes. Biotechniques 28(4):732-738 (Apr. 2000).
Tomizawa et al. Initiation of DNA synthesis in *Escherichia coli*. Annu. Rev. Biochem. 48:999-1034 (1979).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 14/910,203 Office Action dated Feb. 5, 2019.
U.S. Appl. No. 14/910,203 Office Action dated Sep. 13, 2018.
U.S. Appl. No. 15/302,874 Office Action dated Jan. 28, 2019.
U.S. Appl. No. 15/302,874 Office Action dated Jul. 27, 2018.
U.S. Appl. No. 15/302,874 Office Action dated Jun. 19, 2019.
U.S. Appl. No. 15/302,874 Office Action dated Mar. 13, 2018.

SEQUENCE LISTING

```
Sequence total quantity: 5
SEQ ID NO: 1            moltype = AA  length = 133
FEATURE                 Location/Qualifiers
source                  1..133
                        mol_type = protein
                        organism = Homo sapiens
SEQUENCE: 1
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 2            moltype = AA  length = 153
FEATURE                 Location/Qualifiers
source                  1..153
                        mol_type = protein
                        organism = Homo sapiens
SEQUENCE: 2
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 3            moltype = AA  length = 5
```

```
                        -continued
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 3
GGGGS                                                                          5

SEQ ID NO: 4            moltype = AA  length = 5
FEATURE                 Location/Qualifiers
REGION                  1..5
                        note = Description of Artificial Sequence: Synthetic peptide
VARIANT                 4
                        note = X is any amino acid except proline
source                  1..5
                        mol_type = protein
                        organism = synthetic construct
SEQUENCE: 4
VPGXG                                                                          5

SEQ ID NO: 5            moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 5
FQSSSSKAPP PSLPSPSRLP GPSDTPILPQ                                               30
```

CYTOKINE CONJUGATES FOR THE TREATMENT OF AUTOIMMUNE DISEASES

CROSS-REFERENCE

This application is a divisional of U.S. application Ser. No. 16/634,487, filed on Jan. 27, 2020, which is a national stage entry under 35 U.S.C. § 371 of PCT International Application No. PCT/US2018/045265, filed on Aug. 3, 2018, which claims the benefit of U.S. Provisional Application No. 62/540,781, filed on Aug. 3, 2017, which is incorporated herein by reference in its entirety.

SEQUENCE LISTING

The instant application contains a Sequence Listing which has been submitted electronically in XML format and is hereby incorporated by reference in its entirety. Said XML copy, created on Mar. 10, 2023, is named "2023-03-10 01183-0067-11US-SYN ST26.xml" and is 7,317 bytes in size.

BACKGROUND OF THE DISCLOSURE

Distinct populations of T cells modulate the immune system to maintain immune homeostasis and tolerance. For example, regulatory T (Treg) cells prevent inappropriate responses by the immune system by preventing pathological self-reactivity while cytotoxic T cells target and destroy infected cells and/or cancerous cells. In some instances, modulation of the different populations of T cells provides an option for treatment of a disease or indication.

SUMMARY OF THE DISCLOSURE

Disclosed herein, in certain embodiments, are cytokine conjugates and use in the treatment of one or more indication. In some embodiments, also described herein include interleukin 2 (IL-2) conjugates and use in the treatment of one or more indications. In some instances, the one or more indications comprise an autoimmune disease. In some cases, described herein are IL-2 conjugates for modulating the interaction between IL-2 and IL-2 receptor to stimulate or expand specifically regulatory T cell (Treg cell) populations. In some cases, described herein are IL-2 conjugates with extended in vivo half-life, reduced toxicity, and/or expanded therapeutic windows. In additional cases, described herein are pharmaceutical compositions and kits which comprise one or more interleukin conjugates (e.g., IL-2 conjugates) described herein.

Disclosed herein, in certain embodiments, is an isolated and modified interleukin 2 (IL-2) polypeptide comprising at least one unnatural amino acid at a position that reduces receptor signaling potency to interleukin 2 receptor βγ (IL-2Rβγ) or reduces a recruitment of an IL-2Rγ subunit to the IL-2/IL-2Rβ complex, but retains significant activation of interleukin 2 αβγ receptor (IL-2Rαβγ), wherein the reduced receptor signaling potency is compared to the receptor signaling potency between a wild-type IL-2 polypeptide and IL-2Rβγ, and wherein the recruitment is compared to a recruitment of an IL-2Rγ subunit by a wild-type IL-2 polypeptide. In some embodiments, the position of the at least one unnatural amino acid is selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, S87, N88, V91, I92, L94, E95, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the position of the at least one unnatural amino acid is selected from K8, K9, and H16, wherein the numbering of the amino acid residues corresponds to SEQ ID NO: 1. In some embodiments, the position of the at least one unnatural amino acid is selected from Q22, N26, N88, and Q126, wherein the numbering of the amino acid residues corresponds to SEQ ID NO: 1. In some embodiments, the position of the at least one unnatural amino acid is selected from E15, D20, D84, and E95, wherein the numbering of the amino acid residues corresponds to SEQ ID NO: 1. In some embodiments, the position of the at least one unnatural amino acid is selected from L12, L19, and M23, wherein the numbering of the amino acid residues corresponds to SEQ ID NO: 1. In some embodiments, the position of the at least one unnatural amino acid is selected from Q22 and N26, wherein the numbering of the amino acid residues corresponds to SEQ ID NO: 1. In some embodiments, the at least one unnatural amino acid: is a lysine analogue; is a cysteine analogue or a histidine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, 0-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the isolated and modified IL-2 polypeptide has a decrease in receptor signaling potency to IL-2Rβγ, and the decrease in receptor signaling potency is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more to IL-2Rβγ relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in receptor signaling potency to IL-2Rβγ is capable of expanding CD4+T regulatory (Treg) cells. In some embodiments, the conjugating moiety impairs or blocks the receptor signaling potency of IL-2 with IL-2Rβγ, or reduces recruitment of the IL-2Rγ subunit to the IL-2/IL-2Rβ complex. In some embodiments, CD4+ Treg cell proliferation by the modified IL-2/IL-2Rαβγ complex is equivalent or greater to that of a wild-type IL-2 polypeptide. In some embodiments, the modified IL-2/IL-2Rαβγ complex induces proliferation of the CD4+ Treg cells to a population that is sufficient to modulate a disease course in an animal model. In some embodiments, the modified IL-2 polypeptide exhibits a first receptor signaling potency to IL-21βγ and a second receptor signaling potency to IL-2Rαβγ, wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some embodiments, the first receptor signaling potency of the modified IL-2 polypeptide is lower than a receptor signaling potency of the wild-type IL-2 polypeptide to IL-2Rβγ. In some embodiments, the second receptor signaling potency of the modified IL-2 polypeptide is lower than a receptor signaling potency of the wild-type IL-2 polypeptide to IL-2Rαβγ. In some embodiments, the modified IL-2 polypeptide further provides an increase in a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the modified IL-2 polypeptide further provides a decrease in a recruitment of an IL-2Rγ subunit to the IL-2/IL-2Rβ complex, wherein the reduced recruitment is compared to a recruitment of an IL-2Rβ subunit and/or IL-2Rγ subunit by a wild-type IL-2 polypeptide.

Disclosed herein, in certain embodiments, is an isolated and modified interleukin 2 (IL-2) polypeptide comprising at least one unnatural amino acid at a position that increases a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the position of the at least one unnatural amino acid is selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, S87, N88, V91, I92, L94, E95, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the position of the at least one unnatural amino acid is selected from K8, K9, and H16, wherein the numbering of the amino acid residues corresponds to SEQ ID NO: 1. In some embodiments, the position of the at least one unnatural amino acid is selected from Q22, N26, N88, and Q126, wherein the numbering of the amino acid residues corresponds to SEQ ID NO: 1. In some embodiments, the position of the at least one unnatural amino acid is selected from E15, D20, D84, and E95, wherein the numbering of the amino acid residues corresponds to SEQ ID NO: 1. In some embodiments, the position of the at least one unnatural amino acid is selected from L12, L19, and M23, wherein the numbering of the amino acid residues corresponds to SEQ ID NO: 1. In some embodiments, the position of the at least one unnatural amino acid is selected from Q22 and N26, wherein the numbering of the amino acid residues corresponds to SEQ ID NO: 1. In some embodiments, the at least one unnatural amino acid: is a lysine analogue; is a cysteine analogue or a histidine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, 0-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the isolated and modified IL-2 polypeptide has a decrease in receptor signaling potency to IL-2Rβγ, and the decrease in receptor signaling potency is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more to IL-2Rβγ relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in receptor signaling potency to IL-2Rβγ is capable of expanding CD4+T regulatory (Treg) cells. In some embodiments, the conjugating moiety impairs or blocks the receptor signaling potency of IL-2 with IL-2Rβγ, or reduces recruitment of the IL-2Rγ subunit to the IL-2/IL-2Rβ complex. In some embodiments, CD4+ Treg cell proliferation by the modified IL-2/IL-2Rαβγ complex is equivalent or greater to that of a wild-type IL-2 polypeptide. In some embodiments, the modified IL-2/IL-2Rαβγ complex induces proliferation of the CD4+ Treg cells to a population that is sufficient to modulate a disease course in an animal model. In some embodiments, the modified IL-2 polypeptide exhibits a first receptor signaling potency to IL-2Rβγ and a second receptor signaling potency to IL-2Rαβγ, wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some embodiments, the first receptor signaling potency of the modified IL-2 polypeptide is lower than a receptor signaling potency of the wild-type IL-2 polypeptide to IL-2Rβγ. In some embodiments, the second receptor signaling potency of the modified IL-2 polypeptide is lower than a receptor signaling potency of the wild-type IL-2 polypeptide to IL-2Rαβγ. In some embodiments, the modified IL-2 polypeptide further provides an increase in a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the modified IL-2 polypeptide further provides a decrease in a recruitment of an IL-2Rγ subunit to the IL-2/IL-2Rβ complex, wherein the reduced recruitment is compared to a recruitment of an IL-2Rβ subunit and/or IL-2Rγ subunit by a wild-type IL-2 polypeptide.

Disclosed herein, in certain embodiments, is an isolated and modified interleukin 2 (IL-2) polypeptide comprising at least one unnatural amino acid at a position that reduces binding between the modified IL-2 polypeptide and interleukin 2 receptor βγ (IL-2Rβγ) or reduces a recruitment of an IL-2Rγ subunit to the IL-2/IL-2Rβ complex, but does not impair activation of interleukin 2 αβγ receptor (IL-2Rαβγ), wherein the reduced binding is compared to the binding between a wild-type IL-2 polypeptide and IL-2Rβγ, and wherein the reduced recruitment is compared to a recruitment of an IL-2Rγ subunit by a wild-type IL-2 polypeptide. In some embodiments, the position of the at least one unnatural amino acid is selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, S87, N88, V91, I92, L94, E95, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the position of the at least one unnatural amino acid is selected from K8, K9, and H16, wherein the numbering of the amino acid residues corresponds to SEQ ID NO: 1. In some embodiments, the position of the at least one unnatural amino acid is selected from Q22, N26, N88, and Q126, wherein the numbering of the amino acid residues corresponds to SEQ ID NO: 1. In some embodiments, the position of the at least one unnatural amino acid is selected from E15, D20, D84, and E95, wherein the numbering of the amino acid residues corresponds to SEQ ID NO: 1. In some embodiments, the position of the at least one unnatural amino acid is selected from L12, L19, and M23, wherein the numbering of the amino acid residues corresponds to SEQ ID NO: 1. In some embodiments, the position of the at least one unnatural amino acid is selected from Q22 and N26, wherein the numbering of the amino acid residues corresponds to SEQ ID NO: 1. In some embodiments, the position of the at least one unnatural amino acid is at Q22, wherein the numbering of the amino acid residues corresponds to SEQ ID NO: 1. In some embodiments, the position of the at least one unnatural amino acid is at N26, wherein the numbering of the amino acid residues corresponds to SEQ ID NO: 1. In some embodiments, the at least one unnatural amino acid: is a lysine analogue; is a cysteine analogue or a histidine analogue; comprises an aromatic side chain; comprises an azido group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl) selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly (oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding is about 10%, 20%, 30%, 40%, 50%, 60%, 70%, 80%, 90%, 95%, 99%, or more decrease in binding to IL-21βγ relative to a wild-type IL-2 polypeptide. In some embodiments, the decrease in binding is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more to IL-21βγ relative to a wild-type IL-2 polypeptide. In some embodiments, the decrease in IL-2Rγ subunit recruitment is about 10%, 20%, 30%, 40%, 50%, 60%, 70%, 80%, 90%, 95%, 99%, or more decrease relative to a wild-type IL-2 polypeptide. In some embodiments, the decrease in IL-2Rγ subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in binding affinity to IL-21βγ is capable of expanding CD4+T regulatory (Treg) cells. In some embodiments, the conjugating moiety impairs or blocks the binding of IL-2 with IL-2Rβγ, or reduces recruitment of the IL-2Rγ subunit to the IL-2/IL-2Rβ complex. In some embodiments, CD4+ Treg cell proliferation by the modified IL-2/IL-2Rαβγ complex is equivalent or greater to that of a wild-type IL-2 polypeptide.

Disclosed herein, in certain embodiments, is an interleukin 2 (IL-2) conjugate comprising: an isolated and purified IL-2 polypeptide; and a conjugating moiety that binds to the isolated and purified IL-2 polypeptide at an amino acid residue selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, 5127, 5130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, S87, N88, V91, I92, L94, E95, E116, N119, R120, T123, A125, Q126, 5127, 5130, T131, L132, and T133, wherein the numbering of the amino acid residues corresponds to SEQ ID NO: 1. In some embodiments, the position of the at least one unnatural amino acid is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the amino acid position is selected from K8, K9, and H16. In some embodiments, the amino acid position is selected from Q22, N26, N88, and Q126. In some embodiments, the amino acid position is selected from E15, D20, D84, and E95. In some embodiments, the amino acid position is selected from L12, L19, M23, and F78. In some embodiments, the amino acid position is selected from Q22 and N26. In some embodiments, the amino acid position is at Q22. In some embodiments, the amino acid position is at N26. In some embodiments, the amino acid residue selected from K8, K9, L12, E15, H16, L19, D20, Q22, M23, N26, F78, D84, N88, E95, and Q126 is further mutated to lysine, cysteine, or histidine. In some embodiments, the amino acid residue is mutated to cysteine. In some embodiments, the amino acid residue is mutated to lysine. In some embodiments, the amino acid residue selected from K8, K9, L12, E15, H16, L19, D20, Q22, M23, N26, F78, D84, N88, E95, and Q126 is further mutated to an unnatural amino acid. In some embodiments, the unnatural amino acid comprises p-acetyl-L-phenylalanine, p-azidomethyl-L-phenylalanine (pAMF), p-iodo-L-phenylalmne, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine. In some embodiments, the additional mutated amino acid residue binds to an additional conjugating moiety. In some embodiments, the IL-2 conjugate has a decreased affinity to IL-2 receptor β (IL-2Rβ) subunit, IL-2 receptor γ (IL-2Rγ) subunit, or a combination thereof, relative to a wild-type IL-2 polypeptide. In some embodiments, the decreased affinity is about 10%, 20%, 30%, 40%, 50%, or 60% decrease in binding affinity to IL-2Rβ, IL-2Rγ, or a combination thereof, relative to a wild-type IL-2 polypeptide. In some embodiments, the decreased affinity is about 1-fold, 2-fold, 3-fold, 4-fold, 5-fold, 6-fold, 7-fold, 8-fold, 9-fold, 10-fold, or more relative to a wild-type IL-2 polypeptide. In some embodiments, the conjugating moiety impairs or blocks the binding of IL-2 with IL-2Rβ, IL-2Rγ, or a combination thereof. In some embodiments, the conjugating moiety down-modulates recruitment of the IL-Ry chain to the formed IL-2/IL-2Rβ chain complex. In some embodiments, the conjugating moiety extends the systemic half-life of the polypeptide without affecting its affinity for the α, β and γ chains of the IL-2 receptor. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2- pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-φ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), 1-(ρ-Azidosalicylamido)-4-(iodoacetamido)butane (AsIB), N-[4-(ρ-azidosalicylamido) butyl]-31-(2'-pyridyldithio)propionamide (APDP), benzophenone-4-iodoacetamide, ρ-azidobenzoyl hydrazide (ABH), 4-(ρ-azidosalicylamido)butylamine (AsBA), or ρ-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl) cyclohexane-1-carboxylate (sulfo-sMCC). In some embodiments, the linker further comprises a spacer. In some embodiments, the spacer comprises p-aminobenzyl alcohol (PAB), p-aminobenzyoxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate.

Disclosed herein, in certain embodiments, is an interleukin 2 (IL-2) conjugate comprising: an isolated and purified IL-2 polypeptide; and a conjugating moiety; wherein the IL-2 conjugate has a decreased affinity to IL-2 receptor β (IL-2Rβ) subunit, IL-2 receptor γ (IL-2Rγ) subunit, or a combination thereof, relative to a wild-type IL-2 polypeptide. In some embodiments, the conjugating moiety is bound to an amino acid residue that interacts with IL-2R(3 or IL-2Rγ. In some embodiments, the conjugating moiety is bound to an amino acid residue selected from K8, K9, Q11, L12, E15, H16, L18, L19, D20, Q22, M23, N26, R81, D84, S87, N88, V91, I92, L94, E95, E116, N119, R120, T123, A125, Q126, 5127, 5130, T131, L132, and T133, wherein the numbering of the amino acid residues corresponds to SEQ ID NO: 1. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly (hydroxyalkylmethacrylamide), poly(hydroxyalkylmethacrylate), poly(saccharides), poly(α-hydroxy acid), poly(vinyl alcohol), polyphosphazene, polyoxazolines (POZ), poly (N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(21-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), 1-(p-Azidosalicylamido)-4-(iodoacetamido)butane (AsIB), N-[4-(ρ-azidosalicylamido) butyl]-3'-(2'-pyridyldithio)propionamide (APDP), benzophenone-4-iodoacetamide, ρ-azidobenzoyl hydrazide (ABH), 4-(ρ-azidosalicylamido)butylamine (AsBA), or ρ-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl) cyclohexane-1-carboxylate (sulfo-sMCC). In some embodiments, the linker further comprises a spacer. In some embodiments, the spacer comprises p-aminobenzyl alcohol (PAB), p-aminobenzoyxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate.

Disclosed herein, in certain embodiments, is a pharmaceutical composition comprising: an IL-2 conjugate described above; and a pharmaceutically acceptable excipient. In some embodiments, the pharmaceutical composition is formulated for parenteral administration.

Disclosed herein, in certain embodiments, is a method of treating an autoimmune disease or disorder in a subject in need thereof, comprising administering to the subject a therapeutically effective amount of an IL-2 conjugate described above. In some embodiments, the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis. In some embodiments, the method further comprises administering an additional therapeutic agent. In some embodiments, the IL-2 conjugate and the additional therapeutic agent are administered simultaneously. In some embodiments, the IL-2 conjugate and the additional therapeutic agent are administered sequentially. In some embodiments, the IL-2 conjugate is administered prior to the additional therapeutic agent. In some embodiments, the IL-2 conjugate is administered after the administration of the additional therapeutic agent. In some embodiments, the subject is a human.

Disclosed herein, in certain embodiments, is a method of expanding regulatory T (Treg) cell population, comprising: (a) contacting a cell with an IL-2 conjugate described above; and (b) interacting the IL-2 conjugate with IL-2Rα, IL-2Rβ, and IL-2Rγ subunits to form an IL-2/IL-2Rαβγ complex; wherein the IL-2 conjugate has a decreased affinity to IL-2Rβ and/or IL-2Rγ subunits, or down-modulates the recruitment of the IL-2Rγ subunit to the IL-2/IL-2Rβ complex, or retains similar potency as IL-2 at it's α, β and γ receptor subunits, but extends its half-life, and wherein the IL-2/IL-2Rαβγ complex stimulates the expansion of Treg cells similarly or more potently than native IL-2.

Disclosed herein, in certain embodiments, is a kit comprising an IL-2 conjugate described above; or a pharmaceutical composition comprising an IL-2 conjugate described above. In some embodiments, also described herein is a kit comprising a polynucleic acid molecule encoding an IL-2 polypeptide described above.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-FIG. 2B illustrate exemplary unnatural amino acids. FIG. 2A illustrates exemplary lysine derivatives. FIG. 2B illustrates exemplary phenylalanine derivatives.

FIG. 3B—UAA #43-89; FIG. 3C—UAA #90-128; FIG.

3D—UAA #129-167). FIGS. 3A-3D are adopted from Table 1 of Dumas et al., *Chemical Science* 2015, 6, 50-69.

DETAILED DESCRIPTION OF THE DISCLOSURE

Figure 1:
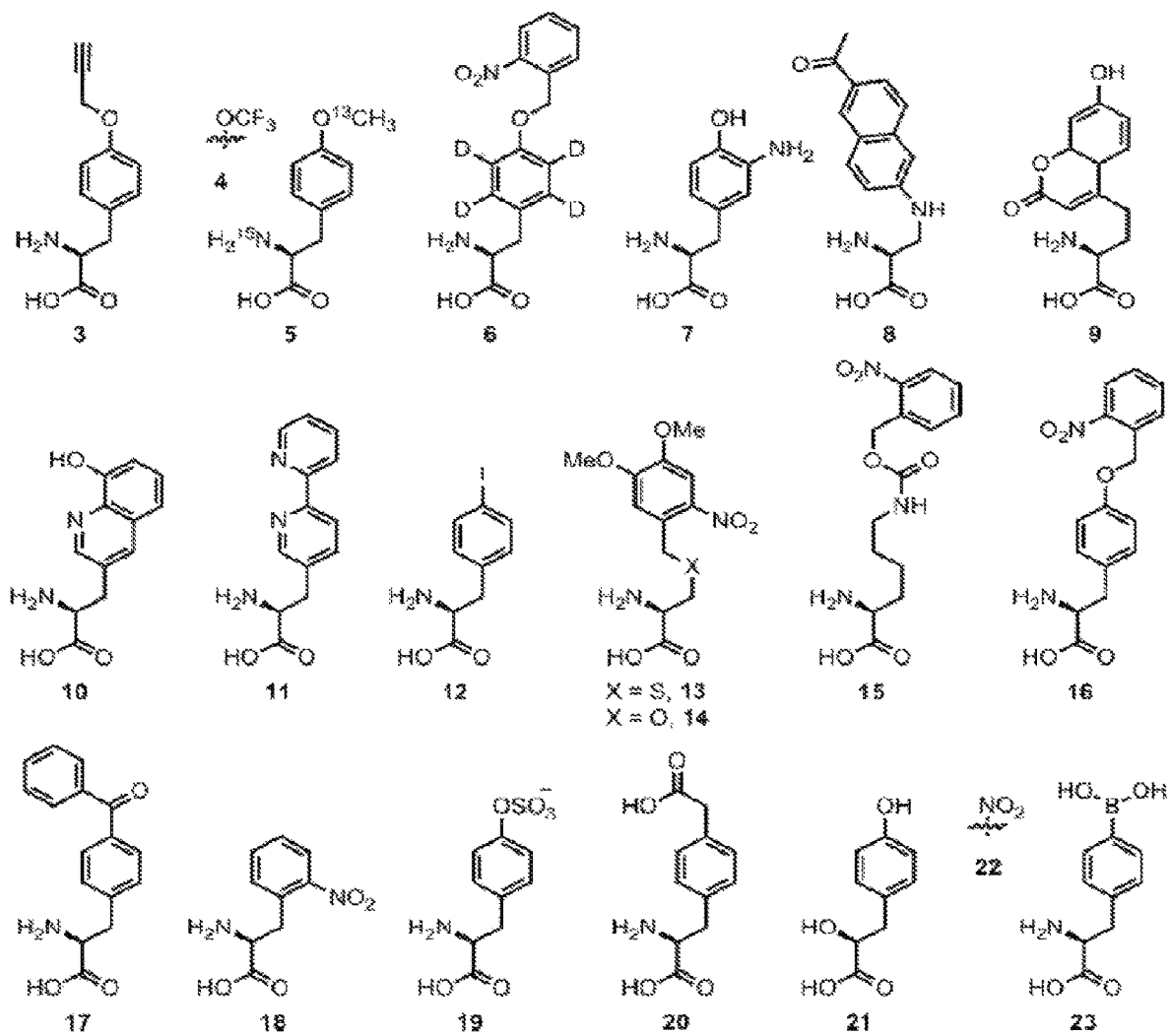
FIG. 1 shows exemplary unnatural amino acids. This figure is adapted from FIG. 2 of Young et al., "Beyond the canonical 20 amino acids: expanding the genetic lexicon," *J. of Biological Chemistry* 285(15): 11039-11044 (2010).

Cytokines comprise a family of cell signaling proteins such as chemokines, interferons, interleukins, lymphokines, tumor necrosis factors, and other growth factors playing roles in innate and adaptive immune cell homeostasis. Cytokines are produced by immune cells such as macrophages, B lymphocytes, T lymphocytes and mast cells, endothelial cells, fibroblasts, and different stromal cells. In some instances, cytokines modulate the balance between humoral and cell-based immune responses.

Interleukins are signaling proteins which modulate the development and differentiation of T and B lymphocytes, cell of the monocytic lineage, neutrophils, basophils, eosinophils, megakaryocytes, and hematopoietic cells. Interleukins are produced by helper CD4 T and B lymphocytes, monocytes, macrophages, endothelial cells, and other tissue residents. In some cases, there are about 15 interleukins, interleukins 1-13, interleukin 15, and interleukin 17.

Interleukin 2 (IL-2) is a pleiotropic type-1 cytokine whose structure comprises a 15.5 kDa four α-helix bundle. The precursor form of IL-2 is 153 amino acid residues in length, with the first 20 amino acids forming a signal peptide and residues 21-153 forming the mature form. IL-2 is produced primarily by CD4+ T cells post antigen stimulation and to a lesser extent, by CD8+ cells, Natural Killer (NK) cells, and NK T (NKT) cells, activated dendritic cells (DCs), and mast cells. IL-2 signaling occurs through interaction with specific combinations of IL-2 receptor (IL-2R) subunits, IL-2Rα (also known as CD25), IL-2Rβ (also known as CD122), and IL-2Rγ (also known as CD132). Interaction of IL-2 with the IL-2Rα forms the "low-affinity" IL-2 receptor complex with a $K_d$ of about $10^{-8}$M. Interaction of IL-2 with IL-2Rβ and IL-2Rγ forms the "intermediate-affinity" IL-2 receptor complex with a $K_d$ of about $10^{-9}$ M. Interaction of IL-2 with all three subunits, IL-2Rα, IL-2Rβ, and IL-2Rγ, forms the "high-affinity" IL-2 receptor complex with a $K_d$ of about $>10^{-11}$ M.

In some instances, IL-2 signaling via the "high-affinity" IL-2Rαβγ complex modulates the activation and proliferation of regulatory T cells. Regulatory T cells, or CD4+ CD25+Foxp3+ regulatory T (Treg) cells mediate maintenance of immune homeostasis by suppression of effector cells such as CD8+ T cells, helper cells such as CD4+ Th1, Th2, and Th17 cells, B cells, NK cells, and NK T cells. In some instances, Treg cells are generated from the thymus (tTreg cells) or are induced from naïve T cells in the periphery (pTreg cells). In some cases, Treg cells are considered as the mediator of peripheral tolerance. Indeed, in one study, transfer of CD25-depleted peripheral CD4+ T cells produced a variety of autoimmune diseases in nude mice, whereas cotransfer of CD4+CD25+ T cells suppressed the development of autoimmunity (Sakaguchi, et al., "Immunologic self-tolerance maintained by activated T cells expressing IL-2 receptor alpha-chains (CD25)," *J. Immunol.* 155(3): 1151-1164 (1995)). Augmentation of the Treg cell population down-regulates effector T cell proliferation and suppresses autoimmunity and T cell anti-tumor responses.

Disclosed herein, in certain embodiments, is a method of selectively upregulating distinct population(s) of lymphocytes (e.g., regulatory T cells) through cytokine/cytokine receptor signaling. In some instances, the cytokine comprises an interleukin. In some cases, the cytokine is a cytokine conjugate, e.g., an interleukin conjugate, an interferon conjugate, or a tumor necrosis factor conjugate. In additional cases, described herein comprise pharmaceutical compositions and kits comprising one or more cytokine conjugates described herein.

In some embodiments, also described herein is a method of selectively upregulating Treg population through IL-2/IL-2R signaling. In some instances, IL-2 is an IL-2 conjugate has a weakened IL-2Rβ and IL-2Rγ interaction within the IL-2Rαβγ complex relative to wild-type IL-2, or downmodulates the recruitment of the IL-2Rγ subunit to the IL-2/IL-2Rβ complex, or retains similar potency as IL-2 at it's α, β and γ receptor subunits, but extends its half-life. In some embodiments, further described herein are methods of treating an autoimmune disease with use of an IL-2 conjugate described herein. In additional embodiments, described herein are pharmaceutical compositions and kits which comprise one or more IL-2 conjugates described herein.

Cytokine Conjugates

In some embodiments, described herein are cytokine conjugates. In some instances, the cytokine comprises an interleukins, a tumor necrosis factor, an interferon, a chemokine, or a lymphokine. In some instances, the cytokine is an interleukin. In some cases, the cytokine is an interferon. In additional cases, the cytokine is a tumor necrosis factor.

In some embodiments, described herein is an interleukin conjugate. Exemplary interleukins include, but are not limited to, interleukin 1β (IL-1β), interleukin 2 (IL-2), interleukin 7 (IL-7), interleukin 10 (IL-10), interleukin 12 (IL-12), interleukin 15 (IL-15), interleukin 18 (IL-18), and interleukin 21 (IL-21). In some instances, described herein is an interleukin conjugate, in which the interleukin is selected from IL-1β, IL-2, IL-7, IL-10, IL-12, IL-15, IL-18, and IL-21.

IL-2 Conjugates

In some embodiments, described herein are IL-2 conjugates modified at an amino acid position. In some instances, the IL-2 polypeptide is an isolated and purified IL-2 polypeptide. In some instances, the IL-2 polypeptide is a mammalian IL-2, for example, a rodent IL-2 protein, or a human IL-2 protein. In some cases, the IL-2 polypeptide is a human IL-2 protein. In some cases, the IL-2 polypeptide comprises about 80%, 85%, 90%, 95%, 96%, 97%, 98%, or 99% sequence identity to SEQ ID NO: 1. In some cases, the IL-2 polypeptide comprises the sequence of SEQ ID NO: 1. In some cases, the IL-2 polypeptide consists of the sequence of SEQ ID NO: 1. In additional cases, the IL-2 polypeptide comprises about 80%, 85%, 90%, 95%, 96%, 97%, 98%, or 99% sequence identity to SEQ ID NO: 2. In additional cases, the IL-2 polypeptide comprises the sequence of SEQ ID NO: 2. In additional cases, the IL-2 polypeptide consists of the sequence of SEQ ID NO: 2.

In some instances, the IL-2 polypeptide is a truncated variant. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the IL-2 polypeptide comprises an N-terminal deletion of at least or about 1, 2, 3, 4, 5, 6, 7, 8, 9, 10, 11, 12, 13, 14, 15, 20, or more residues. In some cases, the IL-2 polypeptide comprises an N-terminal deletion of at least or about 1, 2, 3, 4, 5, 6, 7, 8, 9, or 10 residues. In some cases, the IL-2 polypeptide comprises an N-terminal deletion of at least or about 2 residues. In some cases, the IL-2 polypeptide comprises an N-terminal deletion of at least or about 3 residues. In some cases, the IL-2 polypeptide comprises an N-terminal deletion of at least or about 4 residues. In some cases, the IL-2 polypeptide comprises an N-terminal deletion of at least or about 5 residues. In some cases, the IL-2 polypeptide comprises an N-terminal deletion of at least or about 6 residues. In some cases, the IL-2 polypeptide comprises an N-terminal deletion of at least or about 7 residues. In some cases, the IL-2 polypeptide comprises an N-terminal deletion of at least or about 8 residues. In some cases, the IL-2 polypeptide comprises an N-terminal deletion of at least or about 9 residues. In some cases, the IL-2 polypeptide comprises an N-terminal deletion of at least or about 10 residues.

In some embodiments, the IL-2 polypeptide is a functionally active fragment. In some cases, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some cases, the functionally active fragment comprises IL-2 region 10-133, wherein the residue positions are in reference to the positions in SEQ ID NO: 1. In some cases, the functionally active fragment comprises IL-2 region 20-133, wherein the residue positions are in reference to the positions in SEQ ID NO: 1. In some cases, the functionally active fragment comprises IL-2 region 30-133, wherein the residue positions are in reference to the positions in SEQ ID NO: 1. In some cases, the functionally active fragment comprises IL-2 region 10-125, wherein the residue positions are in reference to the positions in SEQ ID NO: 1. In some cases, the functionally active fragment comprises IL-2 region 20-125, wherein the residue positions are in reference to the positions in SEQ ID NO: 1. In some cases, the functionally active fragment comprises IL-2 region 1-130, wherein the residue positions are in reference to the positions in SEQ ID NO: 1. In some cases, the functionally active fragment comprises IL-2 region 1-125, wherein the residue positions are in reference to the positions in SEQ ID NO: 1.

In some embodiments, an IL-2 conjugate described herein comprising an isolated and purified IL-2 polypeptide and a conjugating moiety has a decreased affinity to IL-2 receptor β (IL-2Rβ) subunit, IL-2 receptor γ (IL-2Rγ) subunit, or a combination thereof, relative to a wild-type IL-2 polypeptide. In some embodiments, the IL-2 conjugate has a reduced IL-2Rγ subunit recruitment to the IL-2/IL-2Rβ complex, relative to a wild-type IL-2 polypeptide. In some cases, the conjugating moiety is bound to an amino acid residue that interacts with IL-2Rβ (e.g., at the IL-2/IL-2Rβ interface), with IL-2Rγ (e.g., at the IL-2/IL-2Rβ interface), or a combination thereof. In some cases, the conjugating moiety is bound to an amino acid residue that is proximal to the IL-2/IL-2Rβ interface, the IL-2/IL-2Rβ interface, or the IL-2βγ interface. In some cases, the amino acid residue is about 5 Å, about 10 Å, about 15 Å, or about 20 Å away from the IL-2/IL-2Rβ interface, the IL-2/IL-2Rβ interface, or the IL-21βγ interface. As used herein, the residues of IL-2 involved in the IL-2/IL-2Rβ interface, the IL-2/IL-2Rβ interface, or the IL-2Rβγ interface comprise IL-2 residues that form hydrophobic interactions, hydrogen bonds, or ionic interactions with residues from the IL-2Rβ subunit, the IL-2Rγ subunit, or residues at the IL-21βγ interface.

In some instances, the conjugating moiety is bound to an amino acid residue selected from an amino acid position P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, 5127, 5130, T131, L132, and T133, in which the numbering of the amino acid residues corresponds to SEQ ID NO: 1. In some instances, the amino acid position is selected from K8, K9, Q11, L12, E15, H16, L18, L19, D20, Q22, M23, N26, R81, D84, S87, N88, V91, I92, L94, E95, E116, N119, R120, T123, A125, Q126, 5127, 5130, T131, L132, and T133. In some instances, the amino acid position is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113. In some instances, the amino acid position is selected from K8, K9, L12, E15, H16, L19, D20, Q22, M23, N26, D84, N88, E95, and Q126. In some instances, the amino acid position is selected from K8, K9, and H16. In some instances, the amino acid position is selected from Q22, N26, N88, and Q126. In some instances, the amino acid position is selected from E15, D20, D84, and E95. In some instances, the amino acid position is selected from L12, L19, and M23. In some instances, the amino acid position is selected from Q22 and N26. In some cases, the amino acid position is at K8. In some cases, the amino acid position is at K9. In some cases, the amino acid position is at Q11. In some cases, the amino acid position is at L12. In some cases, the amino acid position is at E15. In some cases, the amino acid position is at H16. In some cases, the amino acid position is at L18. In some cases, the amino acid position is at L19. In some cases, the amino acid position is at D20. In some cases, the amino acid position is at Q22. In some cases, the amino acid position is at M23. In some cases, the amino acid position is at N26. In some cases, the amino acid position is at R81. In some cases, the amino acid position is at D84. In some cases, the amino acid position is at S87. In some cases, the amino acid position is at N88. In some cases, the amino acid position is at V91. In some cases, the amino acid position is at I92. In some cases, the amino acid position is at L94. In some cases, the amino acid position is at E95. In some cases, the amino acid position is at E116. In some cases, the amino acid position is at N119. In some cases, the amino acid position is at R120. In some cases, the amino acid position is at T123. In some cases, the amino acid position is at A125. In some cases, the amino acid position is at Q126. In some cases, the amino acid position is at S127. In some cases, the amino acid position is at S130. In some cases, the amino acid position is at T131. In some cases, the amino acid position is at L132. In some cases, the amino acid position is at T133.

In some instances, the IL-2 conjugate further comprises an additional mutation. In such cases, the amino acid is conjugated to an additional conjugating moiety for increase in serum half-life, stability, or a combination thereof. Alternatively, the amino acid is first mutated to a natural amino acid such as lysine, cysteine, histidine, arginine, aspartic acid, glutamic acid, serine, threonine, or tyrosine; or to an unnatural amino acid prior to binding to the additional conjugating moiety.

In some embodiments, the IL-2 conjugate has a decreased binding affinity to IL-2 receptor β (IL-2Rβ) subunit, IL-2 receptor γ (IL-2Rγ) subunit, or a combination thereof, of the IL-2Rαβγ complex, relative to a wild-type IL-2 polypeptide. In some instances, the decreased affinity of the IL-2 conjugate to IL-2 receptor β (IL-2Rβ) subunit, IL-2 receptor γ (IL-2Rγ) subunit, or a combination thereof, relative to a wild-type IL-2 polypeptide, is about 10%, 20%, 30%, 40%, 50%, 60%, 70%, 80%, 90%, 95%, 99%, or greater than 99%. In some cases, the decreased affinity is about 10%. In some cases, the decreased affinity is about 20%. In some cases, the decreased affinity is about 40%. In some cases, the decreased affinity is about 50%. In some cases, the decreased affinity is about 60%. In some cases, the decreased affinity is about 80%. In some cases, the decreased affinity is about 90%. In some cases, the decreased affinity is about 99%. In some cases, the decreased affinity is greater than 99%. In some cases, the decreased affinity is about 80%. In some cases, the decreased affinity is about 100%.

In some embodiments, the decreased binding affinity of the IL-2 conjugate to IL-2 receptor β (IL-2Rβ) subunit, IL-2 receptor γ (IL-2Rγ) subunit, or a combination thereof, relative to a wild-type IL-2 polypeptide, is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more. In some cases, the decreased affinity is about 1-fold. In some cases, the decreased affinity is about 2-fold. In some cases, the decreased affinity is about 4-fold. In some cases, the decreased affinity is about 5-fold. In some cases, the decreased affinity is about 6-fold. In some cases, the decreased affinity is about 8-fold. In some cases, the decreased affinity is about 10-fold. In some cases, the decreased affinity is about 30-fold. In some cases, the decreased affinity is about 50-fold. In some cases, the decreased affinity is about 100-fold. In some cases, the decreased affinity is about 300-fold. In some cases, the decreased affinity is about 500-fold. In some cases, the decreased affinity is about 1000-fold. In some cases, the decreased affinity is more than 1,000-fold.

In some embodiments, the IL-2 conjugate has a reduced IL-2Rγ subunit recruitment to the IL-2/IL-2Rβ complex. In some cases, the reduced recruitment is compared to an IL-2Rγ subunit recruitment by an equivalent IL-2 polypeptide without the unnatural amino acid (e.g., a wild-type IL-2 polypeptide). In some cases, the decrease in IL-2Rγ subunit recruitment is about 10%, 20%, 30%, 40%, 50%, 60%, 70%, 80%, 90%, 95%, 99%, or greater than 99% decrease relative to an equivalent IL-2 polypeptide without the unnatural amino acid modification. In some cases, the decrease in IL-2Rγ subunit recruitment is about 10%. In some cases, the decrease in IL-2Rγ subunit recruitment is about 20%. In some cases, the decrease in IL-2Rγ subunit recruitment is about 40%. In some cases, the decrease in IL-2Rγ subunit recruitment is about 50%. In some cases, the decrease in IL-2Rγ subunit recruitment is about 60%. In some cases, the decrease in IL-2Rγ subunit recruitment is about 70%. In some cases, the decrease in IL-2Rγ subunit recruitment is about 80%. In some cases, the decrease in IL-2Rγ subunit recruitment is about 90%. In some cases, the decrease in IL-2Rγ subunit recruitment is about 99%. In some cases, the decrease in IL-2Rγ subunit recruitment is greater than 99%. In some cases, the decrease in IL-2Rγ subunit recruitment is about 100%. In some instances, the IL-2 conjugate further has an increase in IL-2Rα subunit recruitment.

In some embodiments, the decrease in IL-2Rγ subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to an equivalent IL-2 polypeptide without the unnatural amino acid modification (e.g., a wild-type IL-2 polypeptide). In some cases, the decrease in IL-2Rγ subunit recruitment is about 1-fold. In some cases, the decrease in IL-2Rγ subunit recruitment is about 2-fold. In some cases, the decrease in IL-2Rγ subunit recruitment is about 4-fold. In some cases, the decrease in IL-2Rγ subunit recruitment is about 5-fold. In some cases, the decrease in IL-2Rγ subunit recruitment is about 6-fold. In some cases, the decrease in IL-2Rγ subunit recruitment is about 8-fold. In some cases, the decrease in IL-2Rγ subunit recruitment is about 10-fold. In some cases, the decrease in IL-2Rγ subunit recruitment is about 30-fold. In some cases, the decrease in IL-2Rγ subunit recruitment is about 50-fold. In some cases, the decrease in IL-2Rγ subunit recruitment is about 100-fold. In some cases, the decrease in IL-2Rγ subunit recruitment is about 300-fold. In some cases, the decrease in IL-2Rγ subunit recruitment is about 500-fold. In some cases, the decrease in IL-2Rγ subunit recruitment is about 1000-fold. In some cases, the decrease in IL-2Rγ subunit recruitment is more than 1,000-fold. In some instances, the IL-2 conjugate further has an increase in IL-2Rα subunit recruitment.

In some embodiments, the IL-2 conjugate has an increase in IL-2Rα subunit recruitment to the IL-2 polypeptide. In some cases, the reduced recruitment is compared to an IL-2Rα subunit recruitment by an equivalent IL-2 polypeptide without the unnatural amino acid (e.g., a wild-type IL-2 polypeptide). In some cases, the increase in IL-2Rα subunit recruitment is about 10%, 20%, 30%, 40%, 50%, 60%, 70%, 80%, 90%, 95%, 99%, or greater than 99% increase relative to an equivalent IL-2 polypeptide without the unnatural amino acid modification. In some cases, the increase in IL-2Rα subunit recruitment is about 10%. In some cases, the increase in IL-2Rα subunit recruitment is about 20%. In some cases, the increase in IL-2Rα subunit recruitment is about 40%. In some cases, the increase in IL-2Rα subunit recruitment is about 50%. In some cases, the increase in IL-2Rα subunit recruitment is about 60%. In some cases, the increase in IL-2Rα subunit recruitment is about 70%. In some cases, the increase in IL-2Rα subunit recruitment is about 80%. In some cases, the increase in IL-2Rα subunit recruitment is about 90%. In some cases, the increase in IL-2Rα subunit recruitment is about 99%. In some cases, the increase in IL-2Rα subunit recruitment is greater than 99%. In some cases, the increase in IL-2Rα subunit recruitment is about 100%. In some instances, the IL-2 conjugate further has a decrease in recruitment of an IL-2Rβ subunit and/or IL-2Rγ subunit.

In some embodiments, the increase in IL-2Rα subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to an equivalent IL-2 polypeptide without the unnatural amino acid modification (e.g., a wild-type IL-2 polypeptide). In some cases, the increase in IL-2Rα subunit recruitment is about 1-fold. In some cases, the increase in IL-2Rα subunit recruitment is about 2-fold. In some cases, the increase in IL-2Rα subunit recruitment is about 4-fold. In some cases, the increase in IL-2Rα subunit recruitment is about 5-fold. In some cases, the increase in IL-2Rα subunit recruitment is about 6-fold. In some cases, the increase in IL-2Rα subunit recruitment is about 8-fold. In some cases, the increase in IL-2Rα subunit recruitment is about 10-fold.

In some cases, the increase in IL-2Rα subunit recruitment is about 30-fold. In some cases, the increase in IL-2Rα subunit recruitment is about 50-fold. In some cases, the increase in IL-2Rα subunit recruitment is about 100-fold. In some cases, the increase in IL-2Rα subunit recruitment is about 300-fold. In some cases, the increase in IL-2Rα subunit recruitment is about 500-fold. In some cases, the increase in IL-2Rα subunit recruitment is about 1000-fold. In some cases, the increase in IL-2Rα subunit recruitment is more than 1,000-fold. In some instances, the IL-2 conjugate further has a decrease in recruitment of an IL-2Rβ subunit and/or IL-2Rγ subunit.

In some embodiments, an IL-2 polypeptide described herein has a decrease in receptor signaling potency to IL-2Rβγ. In some instances, the decrease in receptor signaling potency is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more to IL-2Rβγ relative to a wild-type IL-2 polypeptide. In some cases, the decrease in receptor signaling potency is about 2-fold. In some cases, the decrease in receptor signaling potency is about 5-fold. In some cases, the decrease in receptor signaling potency is about 10-fold. In some cases, the decrease in receptor signaling potency is about 20-fold. In some cases, the decrease in receptor signaling potency is about 30-fold. In some cases, the decrease in receptor signaling potency is about 40-fold. In some cases, the decrease in receptor signaling potency is about 50-fold. In some cases, the decrease in receptor signaling potency is about 100-fold. In some cases, the decrease in receptor signaling potency is about 200-fold. In some cases, the decrease in receptor signaling potency is about 300-fold. In some cases, the decrease in receptor signaling potency is about 400-fold. In some cases, the decrease in receptor signaling potency is about 500-fold. In some cases, the decrease in receptor signaling potency is about 1000-fold.

In some instances, the receptor signaling potency is measured by an EC50 value. In some cases, the decrease in receptor signaling potency is an increase in EC50. In some instances, the increase in EC50 is about about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more relative to a wild-type IL-2 polypeptide.

In some instances, the receptor signaling potency is measured by an ED50 value. In some cases, the decrease in receptor signaling potency is an increase in ED50. In some instances, the increase in ED50 is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more relative to a wild-type IL-2 polypeptide.

In some embodiments, an IL-2 polypeptide described herein has an expanded therapeutic window compared to a therapeutic window of a wild-type IL-2 polypeptide. In some instances, the expanded therapeutic window is due to a decrease in binding between the IL-2 polypeptide and interleukin 2 receptor βγ (IL-2Rβγ), a decrease in receptor signaling potency to IL-2Rβγ, a decrease in recruitment of an IL-2Rγ subunit to the IL-2/IL-2Rβ complex, or an increase in recruitment of an IL-2Rα subunit to the IL-2 polypeptide. In some instances, the IL-2 polypeptide does not have an impaired activation of interleukin 2 αβγ receptor (IL-2Rαβγ).

In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is at least 1-fold. In some instances, the difference is at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1000-fold, or more. In some instances, the first receptor signaling potency is less than the second receptor signaling potency. In some instances, the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some cases, the modified IL-2 polypeptide has a lower receptor signaling potency to an IL-2βγ signaling complex than a second receptor signaling potency to an IL-2αβγ signaling complex. In some cases, the first receptor signaling potency of the modified IL-2 polypeptide is at least 1-fold lower than a receptor signaling potency of the wild-type IL-2 polypeptide. In some cases, the first receptor signaling potency of the modified IL-2 polypeptide is at least 2-fold, 3-fold, 4-fold, 5-fold, 10-fold, 20-fold, 50-fold, 100-fold, 200-fold, or 500-fold lower than a receptor signaling potency of the wild-type IL-2 polypeptide. In some cases, the first receptor signaling potency and the second receptor signaling potency are both lower that the respective potencies of the wild-type IL-2 polypeptide, but the first receptor signaling potency is lower than the second receptor signaling potency. In some cases, the difference between the first receptor signaling potency and the second receptor signaling potency increases the therapeutic window for the modified IL-2 polypeptide.

In some embodiments, the conjugating moiety is linked to the N-terminus or the C-terminus of an IL-2 polypeptide, either directly or indirectly through a linker peptide. In some cases, the conjugating moiety (e.g., a polymer, a protein, or a peptide) is genetically fused to the IL-2, at the N-terminus or the C-terminus of IL-2, and either directly or indirectly through a linker peptide. In some instances, the conjugating moiety is linked to the N-terminus or the C-terminus amino acid residue. In some instances, the conjugating moiety is linked to a reactive group that is bound to the N-terminus or C-terminus amino acid residue.

In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, or more. In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, or more. In some embodiments, the IL-2 conjugate comprises a plasma half-life of greater than 1 hour. In some embodiments, the IL-2 conjugate comprises a plasma half-life of greater than 2 hours. In some embodiments, the IL-2 conjugate comprises a plasma half-life of greater than 3 hours. In some embodiments, the IL-2 conjugate comprises a plasma half-life of greater than 4 hours. In some embodiments, the IL-2 conjugate comprises a plasma half-life of greater than 5 hours. In some embodiments, the IL-2 conjugate comprises a plasma half-life of greater than 6 hours. In some embodiments, the IL-2 conjugate comprises a plasma half-life of greater than 7 hours. In some embodiments, the IL-2 conjugate comprises a plasma half-life of greater than 8 hours. In some embodiments, the IL-2 conjugate comprises a plasma half-life of greater than 9 hours. In some embodiments, the IL-2 conjugate comprises a plasma half-life of greater than 10 hours.

In some embodiments, the IL-2 conjugate comprises a plasma half-life of greater than 12 hours. In some embodiments, the IL-2 conjugate comprises a plasma half-life of greater than 18 hours. In some embodiments, the IL-2 conjugate comprises a plasma half-life of greater than 24 hours.

In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some embodiments, the IL-2 conjugate comprises a plasma half-life of at least 1 hour. In some embodiments, the IL-2 conjugate comprises a plasma half-life of at least 2 hours. In some embodiments, the IL-2 conjugate comprises a plasma half-life of at least 3 hours. In some embodiments, the IL-2 conjugate comprises a plasma half-life of at least 4 hours. In some embodiments, the IL-2 conjugate comprises a plasma half-life of at least 5 hours. In some embodiments, the IL-2 conjugate comprises a plasma half-life of at least 6 hours. In some embodiments, the IL-2 conjugate comprises a plasma half-life of at least 7 hours. In some embodiments, the IL-2 conjugate comprises a plasma half-life of at least 8 hours. In some embodiments, the IL-2 conjugate comprises a plasma half-life of at least 9 hours. In some embodiments, the IL-2 conjugate comprises a plasma half-life of at least 10 hours. In some embodiments, the IL-2 conjugate comprises a plasma half-life of at least 12 hours. In some embodiments, the IL-2 conjugate comprises a plasma half-life of at least 18 hours. In some embodiments, the IL-2 conjugate comprises a plasma half-life of at least 24 hours.

In some embodiments, the IL-2 conjugate comprises a plasma half-life of from about 1 hour to about 7 days, from about 12 hours to about 7 days, from about 18 hours to about 7 days, from about 24 hours to about 7 days, from about 1 hours to about 5 days, from about 12 hours to about 5 days, from about 24 hours to about 5 days, from about 2 days to about 5 days, or from about 2 days to about 3 days.

In some embodiments, the IL-2 conjugate comprises a plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours.

In some embodiments, the IL-2 conjugate comprises a plasma half-life that is capable of proliferating and/or expanding a Treg cell but does not exert a deleterious effect such as apoptosis.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to a wild-type IL-2.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to a wild-type IL-2.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to a wild-type IL2. In some cases, the reduced toxicity is at least 10%, 20%, 30%, 40%, 50%, 60%, 70%, 80%, 90%, 100%, 200%, 300%, 400%, 500%, or more reduced relative to a wild-type IL-2.

In some embodiments, the IL-2 conjugate comprises a conjugating moiety in which the size (e.g., the volume or length) of the conjugating moiety enhances plasma stability but does not reduce potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety reduces the potency by less than 5%, 4%, 3%, 2%, 1%, or less relative a wild-type IL-2.

In some embodiments, the IL-2 conjugate comprises a conjugating moiety in which the size (e.g., the volume or length) of the conjugating moiety enhances plasma stability and potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety further enhances the potency by more than 5%, 10%, 20%, 30%, 40%, 50%, 60%, 70%, 80%, 90%, 100%, 200%, or more relative to a wild-type IL-2.

In some instances, the conjugating moiety impairs or blocks the receptor signaling potency of IL-2 with IL-2Rβγ, or reduces recruitment of the IL-2Rγ subunit to the IL-2/IL-2Rβ complex.

In some instances, the modified IL-2 polypeptide with the decrease in receptor signaling potency to IL-21βγ is capable of expanding CD4+T regulatory (Treg) cells.

In some embodiments, CD4+ Treg cell proliferation by the modified IL-2/IL-2Rαβγ complex is equivalent or greater to that of a wild-type IL-2 polypeptide.

In some embodiments, the IL-2/IL-2Rαβγ complex induces proliferation of the CD4+ Treg cells to a population that is sufficient to modulate a disease course in an animal model.

In some embodiments, described herein is an interleukin 2 αβγ receptor (IL-2Rαβγ) binding protein, wherein the receptor signaling potency for an interleukin 2 βγ receptor (IL-2Rβγ) of said binding protein is less than that of wild-type human IL-2 (hIL-2), and wherein said binding protein comprises at least one unnatural amino acid. In some cases, said binding protein is a modified IL-2 polypeptide or a functionally active fragment thereof, wherein the modified IL-2 polypeptide comprises at least one unnatural amino acid.

In some embodiments, described herein is an interleukin 2 αβγ receptor (IL-2Rαβγ) binding protein, wherein a recruitment of an IL-2Rγ subunit to an IL-2/IL-2Rβ complex by said binding protein is less than that of wild-type human IL-2 (hIL-2), and wherein said binding protein comprises at least one unnatural amino acid. In some cases, said binding protein is a modified IL-2 polypeptide or a functionally active fragment thereof, wherein the modified IL-2 polypeptide comprises at least one unnatural amino acid.

In some embodiments, described herein is an interleukin 2 αβγ receptor (IL-2Rαβγ) binding protein, wherein the binding affinity for an interleukin 2 βγ receptor (IL-2Rβγ) of said binding protein is less than that of wild-type human IL-2 (hIL-2), and wherein said binding protein comprises at least one unnatural amino acid. In such cases, said binding protein is a modified IL-2 polypeptide or a functionally active fragment thereof, wherein the modified IL-2 polypeptide comprises at least one unnatural amino acid.

In some embodiments, described herein is an IL-2/IL-2Rαβγ complex comprising a modified IL-2 polypeptide comprising an unnatural amino acid and an IL-2Rαβγ, wherein the modified IL-2 polypeptide has a reduced receptor signaling potency toward IL-2Rβγ, and wherein the reduced receptor signaling potency is compared to a binding affinity between a wild-type IL-2 polypeptide and IL-2Rβγ. In some cases, the modified IL-2 polypeptide further comprises a conjugating moiety covalently attached to the unnatural amino acid.

In some embodiments, described herein is an IL-2/IL-2Rαβγ complex comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some cases, the modified IL-2 polypeptide further comprises a conjugating moiety covalently attached to the unnatural amino acid.

In some embodiments, described herein is an IL-2/IL-2Rαβγ complex comprising a modified IL-2 polypeptide comprising an unnatural amino acid and an IL-2Rαβγ, wherein the modified IL-2 polypeptide has a reduced binding affinity toward IL-2Rβγ, and wherein the reduced binding affinity is compared to a binding affinity between a wild-type IL-2 polypeptide and IL-2Rβγ. In some embodiments, described herein is an IL-2/IL-2Rαβγ complex comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some instances, the modified IL-2 polypeptide further comprises a conjugating moiety covalently attached to the unnatural amino acid.

In some embodiments, described herein is a CD4+ Treg cell activator that selectively expands CD4+ Treg cells in a cell population, wherein said activator comprises a modified IL-2 polypeptide comprising at least one unnatural amino acid. In some instances, said activator expands CD8+ effector T cell and/or Natural Killer cells by less than 20%, 15%, 10%, 5%, 1%, or 0.1% in the CD3+ cell population when said activator is in contact with said CD3+ cell population, relative to an expansion of CD8+ effector T cell and/or Natural Killer cells in the CD3+ cell population contacted by a wild-type IL-2 polypeptide. In some instances, said cell population is an in vivo cell population. In some instances, said cell population is an in vitro cell population. In some instances, said cell population is an ex vivo cell population.

IL-10 Conjugates

In some embodiments, described herein are IL-10 conjugates modified at an amino acid position. IL-10, also known as human cytokine synthesis inhibitory factor or CSIF, is an immunomodulatory cytokine that limits the inflammatory response against pathogens but it has also been identified as an antitumor cytokine due to its immunostimulatory activity on CD8 T cells. IL-10 downregulates the expression of Th1 cytokines, MEW class II antigens, and co-stimulatory molecules on macrophages, and further enhances B cell survival, proliferation, and antibody production. Additionally, IL-10 can stimulate proliferation of thymocytes and cytotoxicity of CD8 T cells. In some instances, the IL-10 conjugate comprises an isolated and purified IL-10 polypeptide and a conjugating moiety. In some instances, the IL-10 conjugate has a decreased affinity to an IL-10 receptor relative to a wild-type IL-10 polypeptide. In some cases, the conjugating moiety is bound to an amino acid residue that interacts with the IL-10 receptor (e.g., at an IL-10/IL-10R interface). In some cases, the conjugating moiety is bound to an amino acid residue that is proximal to the IL-10/IL-10R interface (e.g., about 5 Å, about 10 Å, about 15 Å, or about 20 Å away from the IL-10/IL-10R interface). As used herein, the residues involved in the IL-10/IL-10R interface comprise IL-10 residues that form hydrophobic interactions, hydrogen bonds, or ionic interactions with residues from the IL-10R. In some cases, the conjugating moiety is linked to the N-terminus or the C-terminus of the IL-10 polypeptide, either directly or indirectly through a linker peptide. In additional cases, the conjugating moiety modulates the interaction between IL-10 and IL-10R to potentiate its immunosuppressant activity and reduced its immunostimulatory activity. In some instances, the IL-10 conjugate upregulates distinct population(s) of lymphocytes through IL-10/IL-10R signaling. In some instances, the IL-10 conjugate modulates immune activity.

Additional Cytokine Conjugates

In some embodiments, described herein include one or more additional cytokine conjugates modified at an amino acid position. Exemplary cytokines include, but are not limited to, IL-1β, IL-7, IL-12, IL-15, IL-18, and IL-21. In some instances, the cytokine conjugate comprises an isolated and purified cytokine polypeptide and a conjugating moiety. In some instances, the cytokine conjugate has a decreased affinity to its respective receptor relative to a wild-type cytokine. In some cases, the conjugating moiety is bound to an amino acid residue that is proximal to the receptor interface (e.g., about 5 Å, about 10 Å, about 15 Å, or about 20 Å away from the receptor interface). In some cases, the conjugating moiety is linked to the N-terminus or the C-terminus of the cytokine polypeptide, either directly or indirectly through a linker peptide. In additional cases, the conjugating moiety modulates the interaction between cytokine and its receptor to potentiate its immunosuppressant activity and reduced its immunostimulatory activity. In some instances, the cytokine conjugate upregulates distinct population(s) of lymphocytes through its receptor signaling. In some instances, the cytokine conjugate modulates immune activity.

Cytokines Conjugate Precursors

Described herein are cytokine conjugate precursors, comprising a mutant cytokine (such as IL-2), wherein one or more amino acids have been mutated from the wild type amino acid. Such precursors are often used with the methods described herein for the treatment of diseases or conditions. In some embodiments, a cytokine precursor is not conjugated. Such mutations variously comprise additions, deletions, or substitutions. In some embodiments, the mutation comprises substitution to a different natural amino acid. In some instances, the mutant cytokine comprises a mutation at amino acid position P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, 192, L94, E95, K97, G98, S99, E100, T101, T102, F103, M104, C105, E106, Y107, A108, D109, E110, T111, A112, T113, E116, N119, R120, T123, A125, Q126, 5127, 5130, T131, L132, and T133, in which the numbering of the amino acid residues corresponds to SEQ ID NO: 1. In some instances, the amino acid position is selected from K8, K9, Q11, L12, E15, H16, L18, L19, D20, Q22, M23, N26, R81, D84, S87, N88, V91, 192, L94, E95, E116, N119, R120, T123, A125, Q126, 5127, 5130, T131, L132, and T133. In some instances, the amino acid position is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113. In some instances, the amino acid position is selected from K8, K9, L12, E15, H16, L19, D20, Q22, M23, N26, D84, N88, E95, and Q126. In some instances, the amino acid position is selected from K8, K9, and H16. In some instances, the amino acid position is selected from Q22, N26, N88, and Q126. In some instances, the amino acid position is selected from E15, D20, D84, and E95. In some instances, the amino acid position is selected from L12, L19, and M23. In some instances, the amino acid position is selected from Q22 and N26. In some embodiments, a cytokine mutant comprises a conjugation moiety, wherein the conjugation moiety is attached to a mutated site in the mutant cytokine.

Protein or Peptide Fusions

In some embodiments, a cytokine conjugate described herein comprises a cytokine (e.g., IL-2, or other cytokine) that is fused to a peptide or protein (fusion). In some embodimets, the peptide or protein is an antibody or antibody fragment. In some embodiments, a cytokine conjugate described herein comprises a cytokine (e.g., IL-2, or other cytokine) that is fused to an antibody, or its binding fragments thereof. In some embodiments, a cytokine described herein is fused to multiple proteins or peptides. In some embodiments, a cytokine conjugate comprises a cytokine fusion to a protein or peptide, and at least one conjugating moiety. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. Such fusion proteins in some instances are generated directly through translation. In some embodiments, fusions are generated using chemical or other enzymatic ligation method. In some embodiments, a cytokine conjugate comprises a fused peptide or protein is attached by a linker. In some embodiments, the linker is a peptide. In some embodiments, a cytokine conjugate comprises an N-terminal peptide or protein fusion. In some embodiments, a cytokine conjugate comprises a C-terminal peptide or protein fusion. In some cases, the cytokine fused to the peptide or protein is further conjugated to one or more conjugation moieties described below.

In some instances, the cytokine conjugate comprises a fusion to an scFv, bis-scFv, $(scFv)_2$, dsFv, or sdAb fusion. In some cases, the fusion comprises a scFv. In some cases, the cytokine conjugate comprises a fusion to bis-scFv. In some cases, the cytokine conjugate comprises a fusion to $(scFv)_2$. In some cases, the cytokine conjugate comprises a fusion to dsFv. In some cases, the cytokine conjugate comprises a fusion to sdAb. In some cases, the cytokine fused to the scFv, bis-scFv, $(scFv)_2$, dsFv, or sdAb is further conjugated to one or more conjugation moieties described below.

In some instances, the cytokine conjugate comprises a fusion to an Fc portion of an antibody, e.g., of IgG, IgA, IgM, IgE, or IgD. In some instances, the cytokine conjugate comprises a fusion to an Fc portion of IgG (e.g., $IgG_1$, $IgG_3$, or $IgG_4$). In some cases, the cytokine fused to the Fc portion is further conjugated to one or more conjugation moieties described below.

In some cases, a cytokine (e.g., an interleukin, IFN, or TNF) polypeptide is fused to an antibody, or its binding fragments thereof. In some cases, the cytokine polypeptide is fused to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is fused to an Fc portion of an antibody. In additional cases, the cytokine polypeptide is fused to an Fc portion of IgG (e.g., IgG$_1$, IgG$_3$, or IgG$_4$). In some cases, the cytokine fused to the antibody, or its binding fragments thereof is further conjugated to one or more conjugation moieties described below.

In some cases, an IL-2 polypeptide is fused to an antibody, or its binding fragments thereof. In some cases, the IL-2 polypeptide is fused to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is fused to an Fc portion of an antibody. In additional cases, the IL-2 polypeptide is fused to an Fc portion of IgG (e.g., IgG$_1$, IgG$_3$, or IgG$_4$). In some cases, the antibody or its binding fragments thereof fused to the IL-2 polypeptide will not impede binding of the IL-2 polypeptide with the IL-2Rβγ. In some cases, the antibody or its binding fragments thereof fused to the IL-2 polypeptide partially blocks binding of the IL-2 polypeptide with the IL-2Rβγ. In some cases, the IL-2 polypeptide fused to the antibody or its binding fragments thereof is further conjugated to one or more conjugation moieties described below.

Natural and Unnatural Amino Acids

In some embodiments, an amino acid residue described herein (e.g., within a cytokine such as IL-2) is mutated to lysine, cysteine, histidine, arginine, aspartic acid, glutamic acid, serine, threonine, or tyrosine prior to binding to (or reacting with) a conjugating moiety. For example, the side chain of lysine, cysteine, histidine, arginine, aspartic acid, glutamic acid, serine, threonine, or tyrosine may bind to a conjugating moiety described herein. In some instances, the amino acid residue is mutated to cysteine, lysine, or histidine. In some cases, the amino acid residue is mutated to cysteine. In some cases, the amino acid residue is mutated to lysine. In some cases, the amino acid residue is mutated to histidine. In some cases, the amino acid residue is mutated to tyrosine. In some cases, the amino acid residue is mutated to tryptophan. In some embodiments, an unnatural amino acid is not conjugated with a conjugating moiety. In some embodiments, a cytokine described herein comprises an unnatural amino acid, wherein the cytokine is conjugated to the protein, wherein the point of attachment is not the unnatural amino acid.

In some embodiments, an amino acid residue described herein (e.g., within a cytokine such as IL-2) is mutated to an unnatural amino acid prior to binding to a conjugating moiety. In some cases, the mutation to an unnatural amino acid prevents or minimizes a self-antigen response of the immune system. As used herein, the term "unnatural amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, ρ-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, azido-lysine (AzK), an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α, α disubstituted amino acid; a β-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling.

In some embodiments, the unnatural amino acid comprises a photoreactive group, which crosslinks, upon irradiation with, e.g., UV.

In some embodiments, the unnatural amino acid comprises a photo-caged amino acid.

In some instances, the unnatural amino acid is a para-substituted, meta-substituted, or an ortho-substituted amino acid derivative.

In some instances, the unnatural amino acid comprises p-acetyl-L-phenylalanine, p-iodo-L-phenylalanine, O-methyl-L-tyrosine, p-methoxyphenylalanine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxy-phenylalanine, or 3-iodotyrosine.

In some cases, the unnatural amino acid is phenylselenocysteine.

In some instances, the unnatural amino acid is a benzophenone, ketone, iodide, methoxy, acetyl, benzoyl, or azide containing phenylalanine derivative.

In some instances, the unnatural amino acid is a benzophenone, ketone, iodide, methoxy, acetyl, benzoyl, or azide containing lysine derivative.

In some instances, the unnatural amino acid comprises an aromatic side chain.

In some instances, the unnatural amino acid does not comprise an aromatic side chain.

In some instances, the unnatural amino acid comprises an azido group.

In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics.

In some instances, the unnatural amino acid is dehydroalanine.

In some instances, the unnatural amino acid comprises an aldehyde or ketone group.

In some instances, the unnatural amino acid is a lysine derivative comprising an aldehyde or ketone group.

In some instances, the unnatural amino acid is a lysine derivative comprising one or more O, N, Se, or S atoms at the beta, gamma, or delta position. In some instances, the unnatural amino acid is a lysine derivative comprising O, N, Se, or S atoms at the gamma position.

In some instances, the unnatural amino acid is a lysine derivative wherein the epsilon N atom is replaced with an oxygen atom.

In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is a nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group.

In some instances, the unnatural amino acid comprises a transcyclooctenyl group.

In some instances, the unnatural amino acid comprises a norbornenyl group.

In some instances, the unnatural amino acid comprises a cyclopropenyl group.

In some instances, the unnatural amino acid comprises a diazirine group.

In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-{[(tert-butoxy)carbonyl]amino}hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-{[(benzyloxy)carbonyl]amino}hexanoic acid. In some instances, the unnatural amino acid is 2-amino-6-{[(p-iodobenzyloxy)carbonyl]amino}hexanoic acid. In some instances, the unnatural amino acid is 2-amino-6-{[(p-nitrobenzyloxy)carbonyl]amino}hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine. In some instances, the unnatural amino acid is 2-amino-6-{[(2-azidocyclopentyloxy)carbonyl]amino}hexanoic acid. In some instances, the unnatural amino acid is N6-((2-azidoethoxy)carbonyl)lysine. In some instances, the unnatural amino acid is 2-amino-6-{[(2-nitrobenzyloxy)carbonyl]amino}hexanoic acid. In some instances, the unnatural amino acid is 2-amino-6-{[(2-cyclooctynyloxy)carbonyl]amino}hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine, In some instances, the unnatural amino acid is N6-(but-2-enoyl)lysine, In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl) oxy)carbonyl)lysine. In some instances, the unnatural amino acid is N6-((bicyclo[2.2.1]hept-5-en-2-ylmethoxy)carbonyl) lysine. In some instances, the unnatural amino acid is cysteinyllysine. In some instances, the unnatural amino acid is N6-((1-(6-nitrobenzo[d][1,3]dioxol-5-yl)ethoxy)carbonyl)lysine. In some instances, the unnatural amino acid is N6-42-(3-methyl-3H-diazirin-3-yl)ethoxy)carbonyl)lysine. In some instances, the unnatural amino acid is N6-43-(3-methyl-3H-diazirin-3-yl)propoxy)carbonyl)lysine. In some instances, the unnatural amino acid is N6-((meta nitrobenyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid.

In some embodiments, the unnatural amino acid is incorporated into the cytokine (e.g., the IL polypeptide) by a repurposed amber, opal, or ochre stop codon.

In some embodiments, the unnatural amino acid is incorporated into the cytokine (e.g., the IL polypeptide) by a 4-base codon.

In some embodiments, the unnatural amino acid is incorporated into the cytokine (e.g., the IL polypeptide) by a repurposed rare sense codon.

In some embodiments, the unnatural amino acid is incorporated into the cytokine (e.g., the IL polypeptide) by a synthetic codon comprising an unnatural nucleic acid. In some instances, the unnatural amino acid is incorporated into the cytokine by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with a) other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the cytokine (e.g., the IL polypeptide) by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyrRS (Ec-Tyr)IB. *stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine andp-methoyphenylalanine; meta-substituted tyrosine derivatives such as 3-aminotyrosine, 3-nitrotyrosine, 3,4-dihydroxyphenylalanine, and 3-iodotyrosine; phenyl selenocysteine; p-boronopheylalanine; and o-nitrobenzyltyrosine.

In some instances, the unnatural amino acid is incorporated into the cytokine (e.g., the IL polypeptide) by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenoe, ketone, iodide, or azide substituents; O-propargyltyrosine; α-aminocaprylic acid, O-methyl tyrosine, O-nitrobenzyl cysteine; and 3-(naphthalene-2-ylamino)-2-amino-propanoic acid.

In some instances, the unnatural amino acid is incorporated into the cytokine (e.g., the IL polypeptide) by a pyrrolysyl-tRNA pair. In some cases, the PylRS is obtained from an archaebacterial, e.g., from a methanogenic archaebacterial. In some cases, the PylRS is obtained from *Methanosarcina barkeri, Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-$_D$-prolyl-$_L$-lysine, and N-ε-cyclopentyloxycarbonyl-$_L$-lysine; N-ε-Acryloyl-$_L$-lysine; N-ε-[(1-(6-nitrobenzo[d][1,3]dioxol-5-yl)ethoxy)carbonyl]-$_L$-lysine; and N-ε-(1-methylcyclopro-2-enecarboxamido)lysine.

In some instances, an unnatural amino acid is incorporated into a cytokine described herein (e.g., the IL polypeptide) by a synthetase disclosed in U.S. Pat. Nos. 9,988,619 and 9,938,516. Exemplary UAAs tha can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, such synthetases are expressed and used to incorporate UAAs into cytokines in-vivo. In some embodiments, such synthetases are used to incorporate UAAs into cytokines using a cell-free translation system.

In some instances, an unnatural amino acid is incorporated into a cytokine described herein (e.g., the IL polypeptide) by a naturally occurring synthetase. In some embodiments, an unnatural amino acid is incorporated into a cytokine by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

In some instances, the unnatural amino acid comprises an unnatural amino acid illustrated in FIG. 1.

Figure 2A:
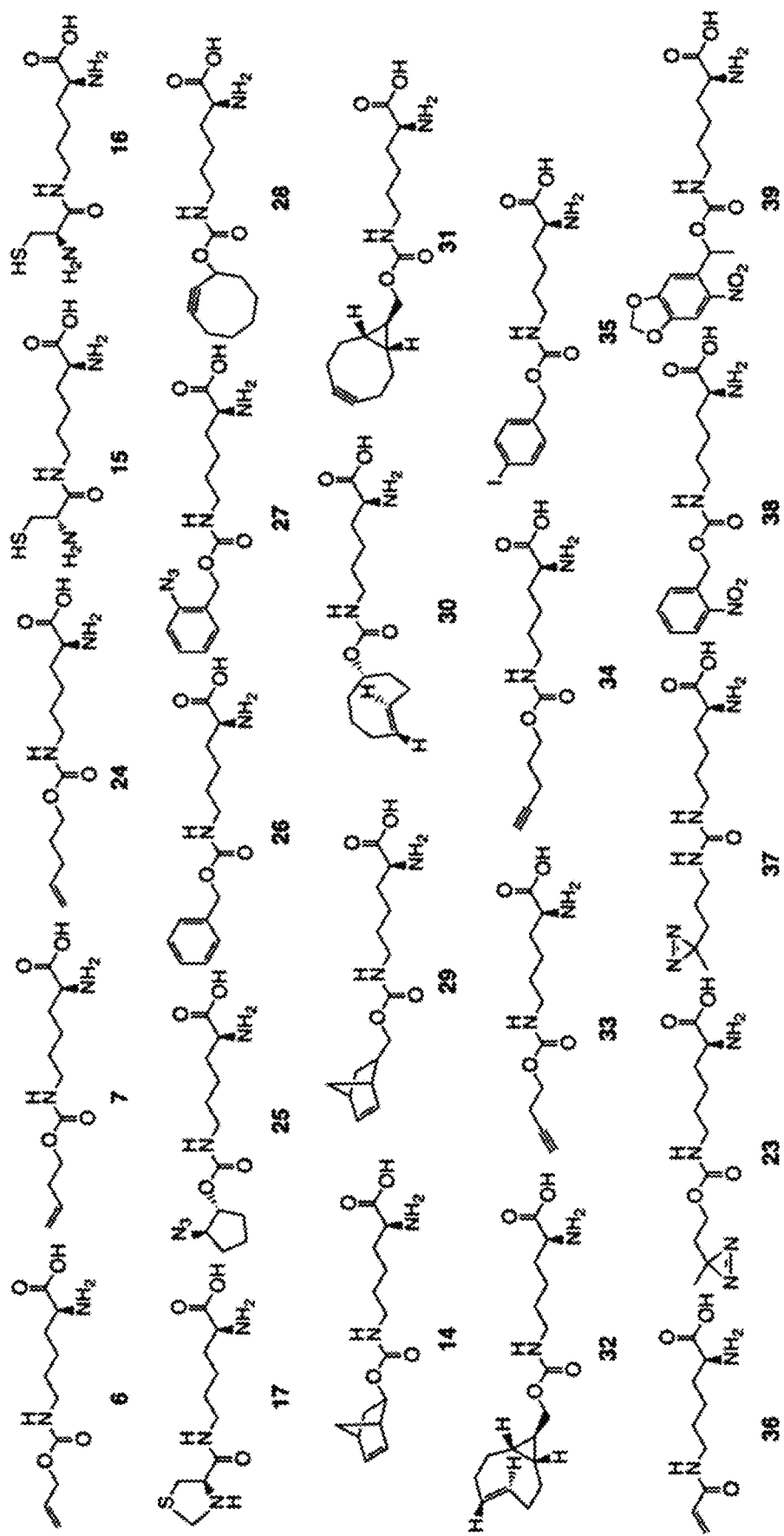
Figure 2A:
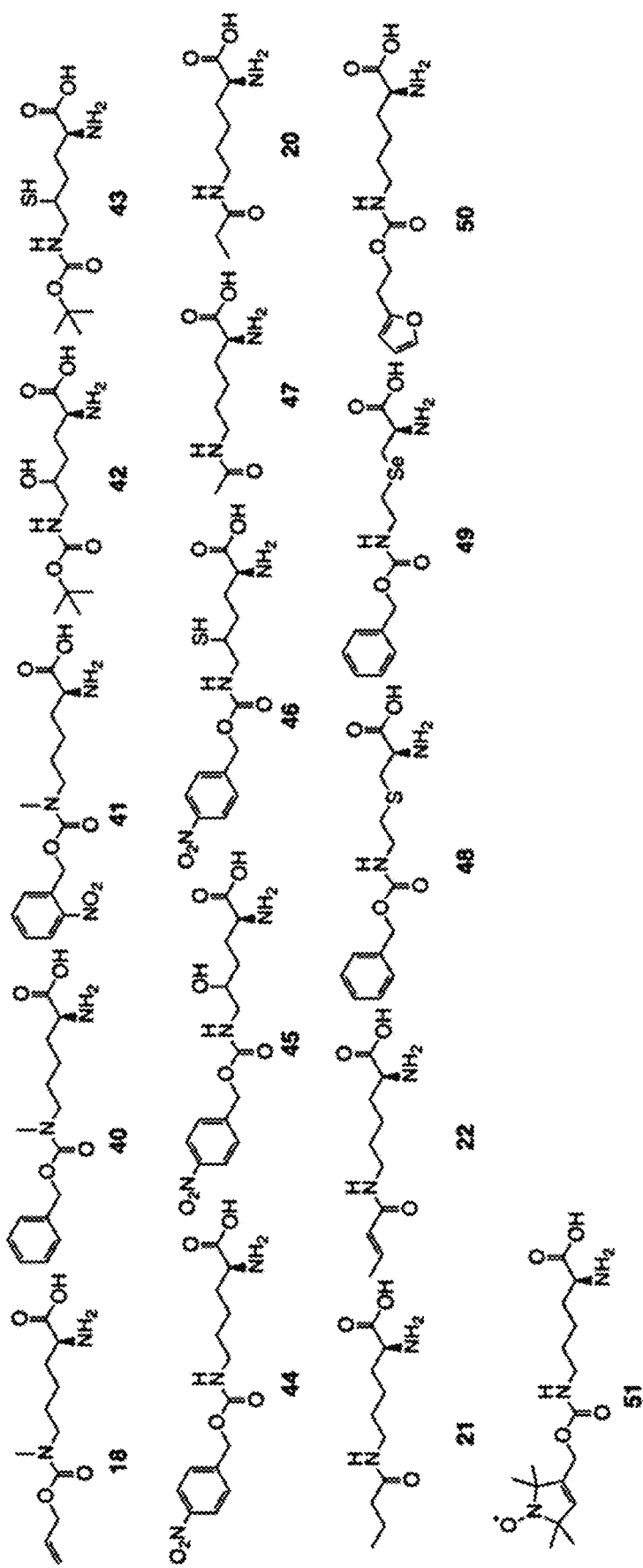
Figure 3A:
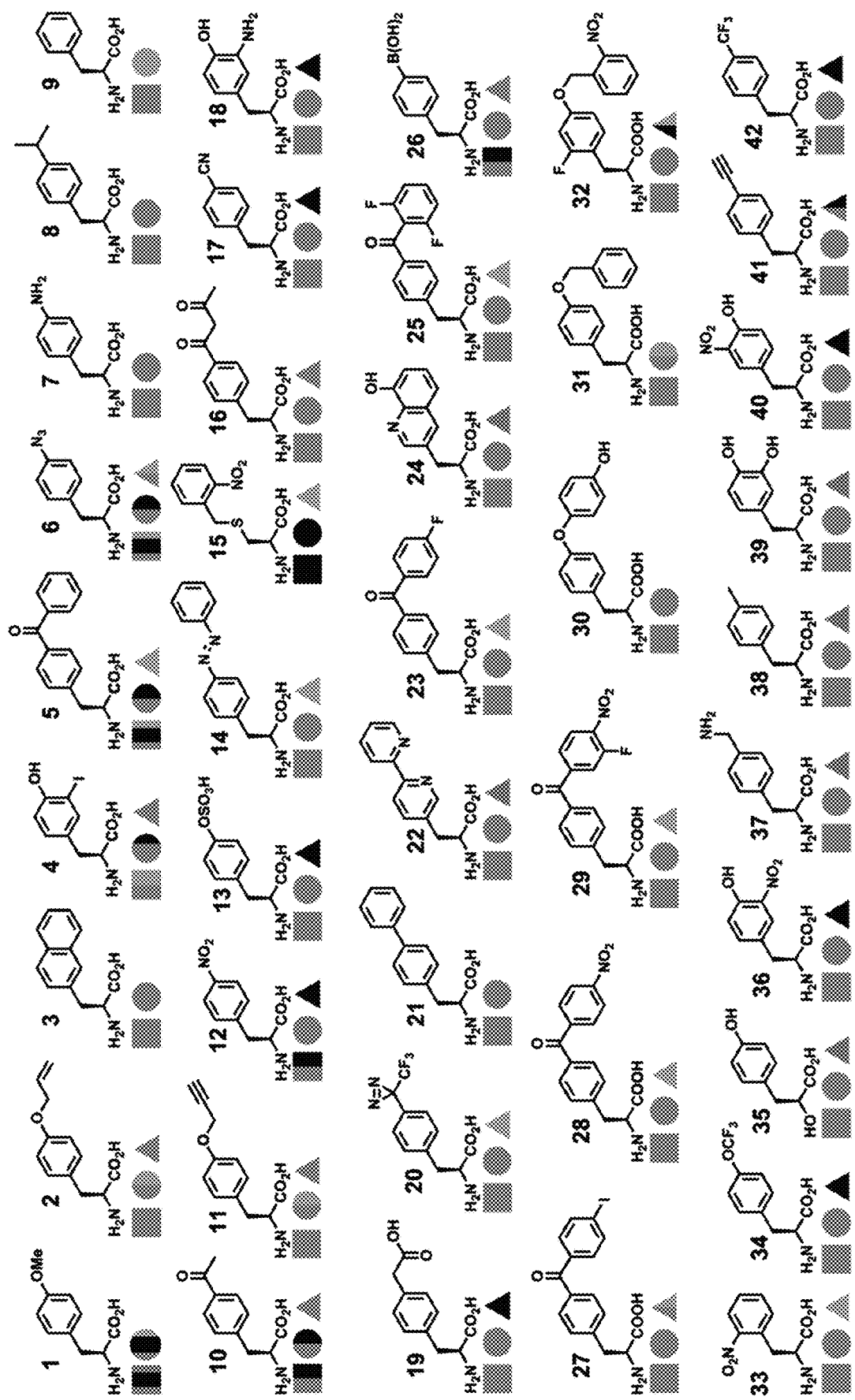
FIG. 3A-FIG. 3D illustrate exemplary unnatural amino acids. These unnatural amino acids (UAAs) have been genetically encoded in proteins (FIG. 3A—UAA #1-42.
Figure 3B:
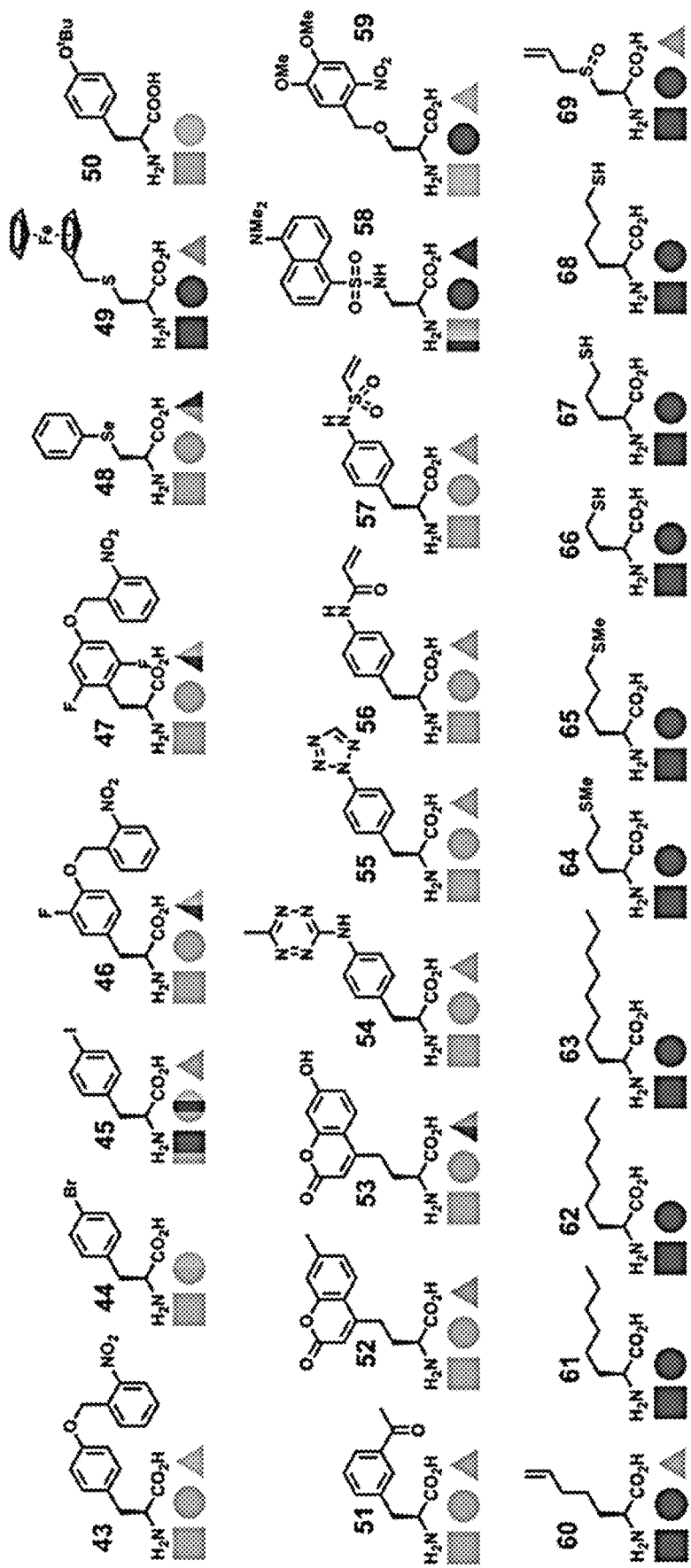
Figure 3B:
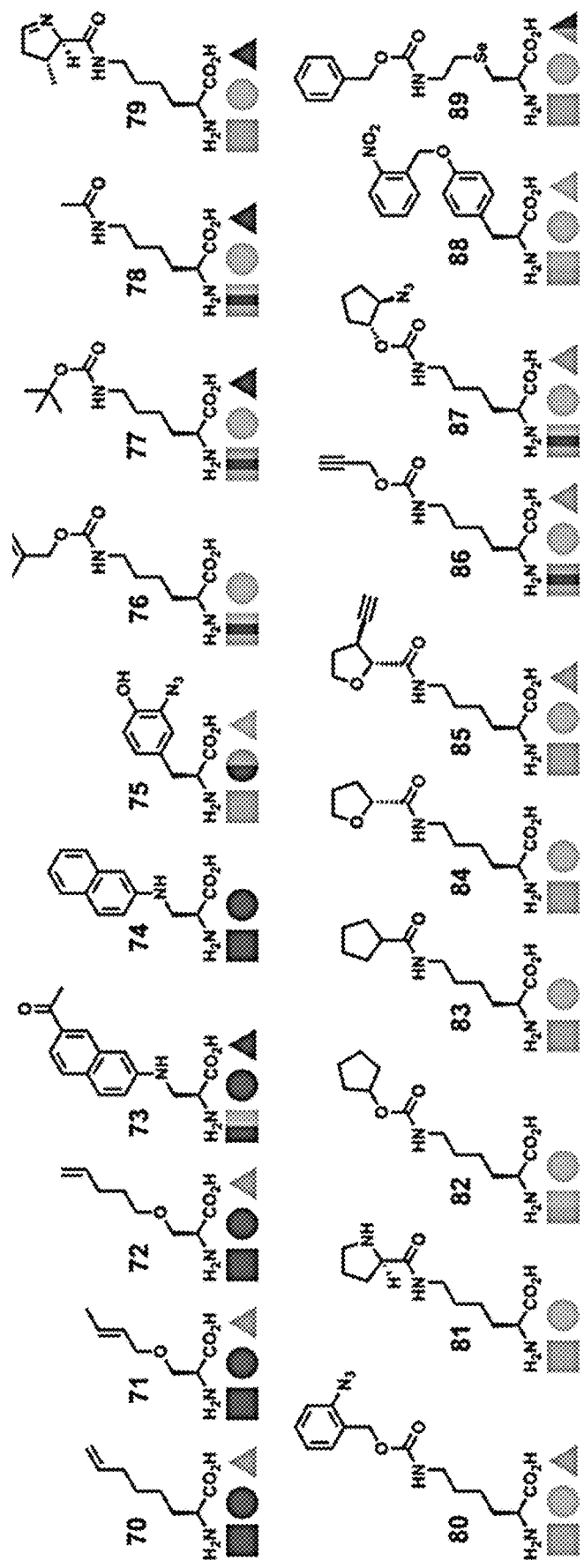
Figure 3C:
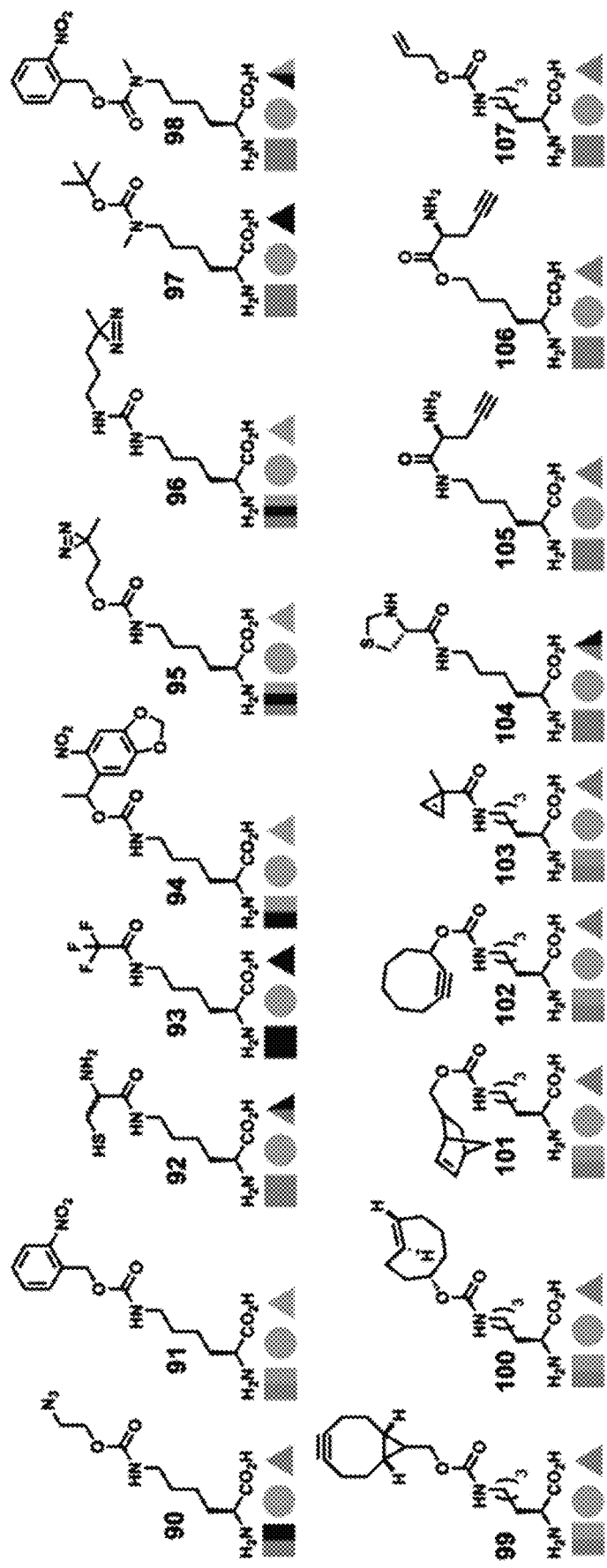
Figure 3C:
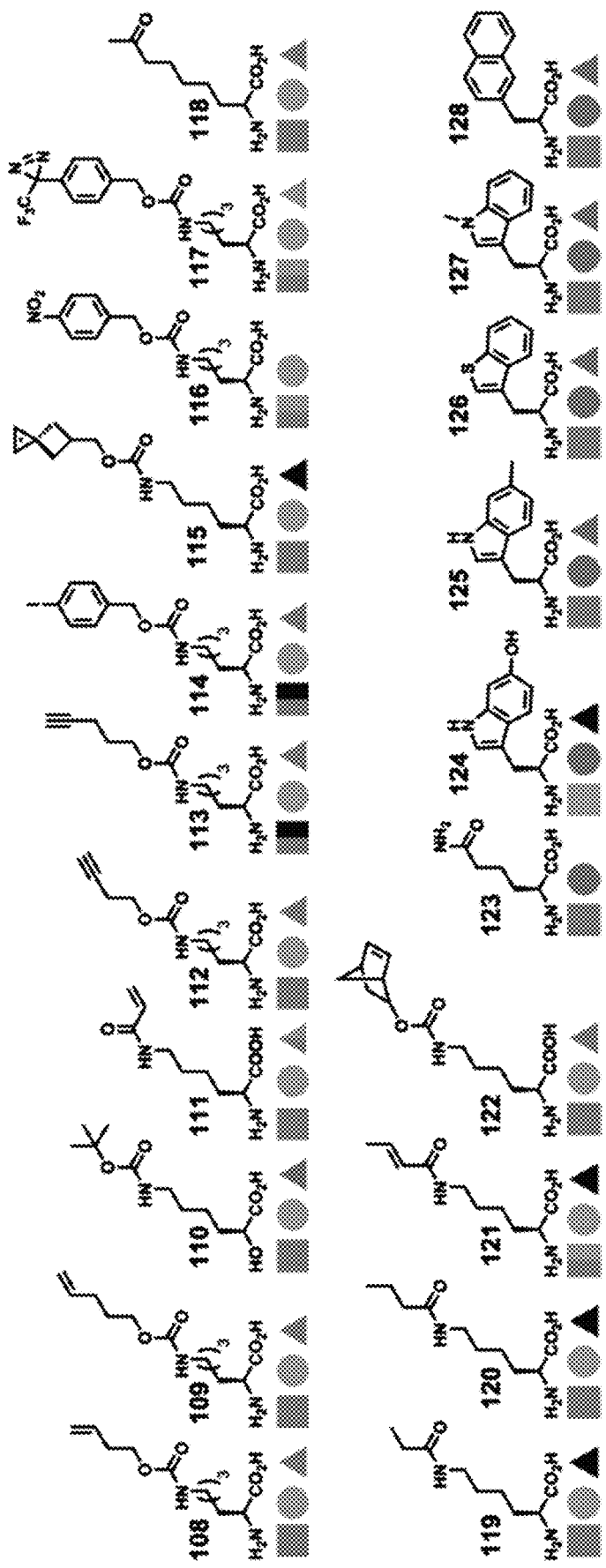
Figure 3D:
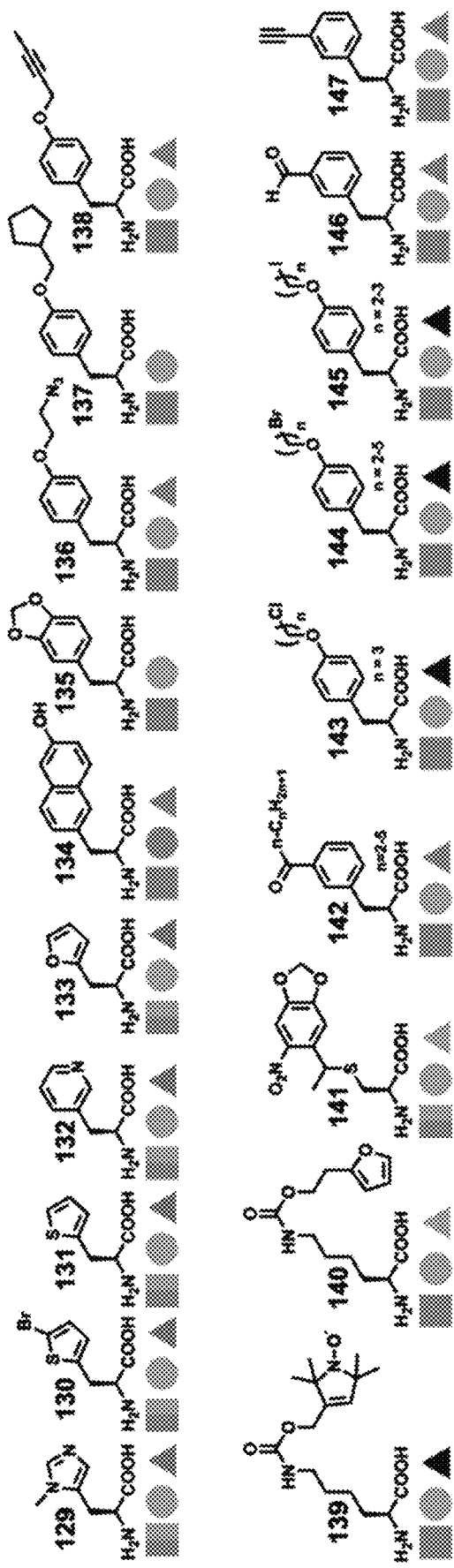
Figure 3D:
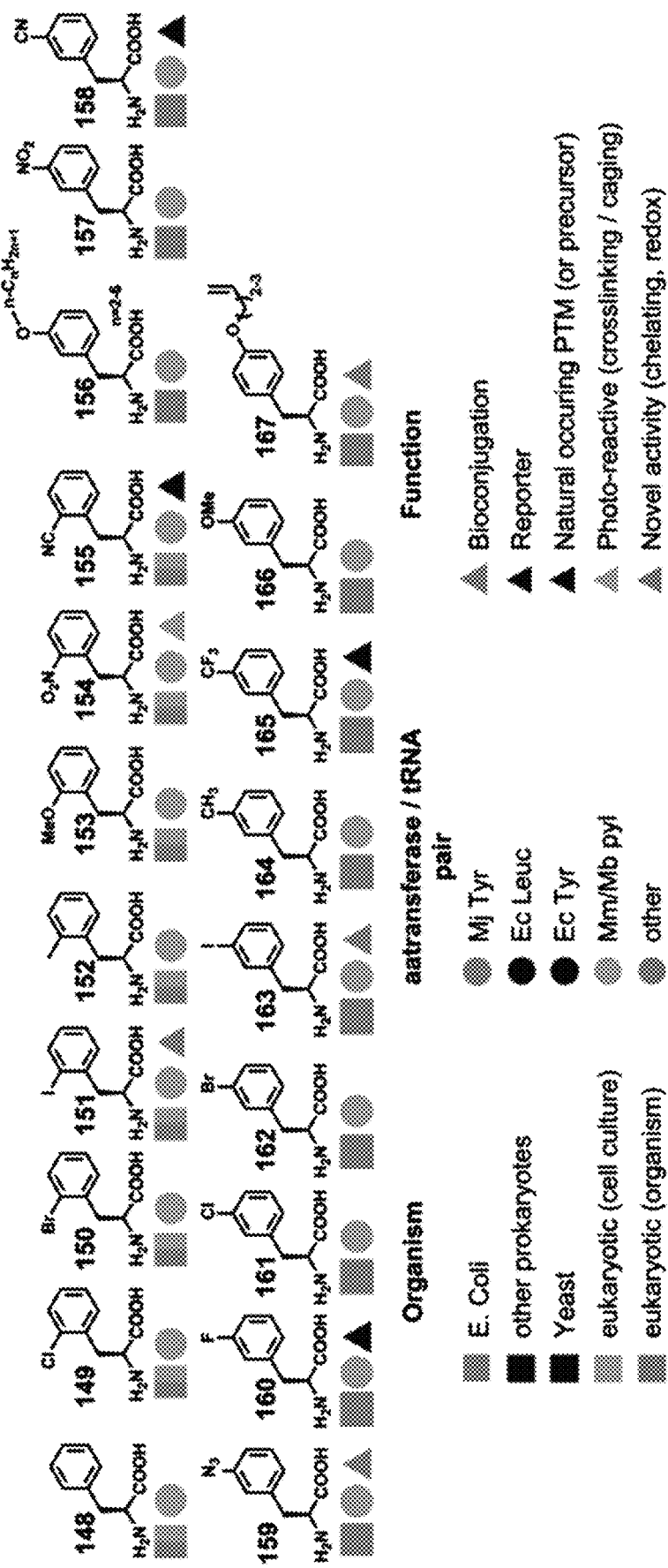

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biocheim Biophys Aceta 1844(6): 1059-4070 (2014). In some instances, the unnatural amino acid comprises an unnatural amino acid illustrated in FIG. 2 (e.g., FIG. 2A and FIG. 2B).

In some embodiments, the unnatural amino acid comprises an unnatural amino acid illustrated in FIG. 3A—FIG. 3D (adopted from Table 1 of Dumas et al., *Chemical Science* 2015, 6, 50-69).

In some embodiments, an unnatural amino acid incorporated into a cytokine described herein (e.g., the IL polypeptide) is disclosed in U.S. Pat. Nos. 9,840,493; 9,682,934; US 2017/0260137; U.S. Pat. No. 9,938,516; or US 2018/0086734. Exemplary UAAs that can be incorporated by such synthetases include para-methylazido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into cytokines in-vivo. In some embodiments, such UAAs are incorporated into cytokines in a cell-free system.

Conjugating Moieties

In certain embodiments, disclosed herein are conjugating moieties that are bound to one or more cytokines (e.g., interleukins, IFNs, or TNFs) described supra. In some instances, the conjugating moiety is a molecule that perturbs the interaction of a cytokine with its receptor. In some instances, the conjugating moiety is any molecule that when bond to the cytokine, enables the cytokine conjugate to modulate an immune response. In some instances, the conjugating moiety comprises a water-soluble polymer. In other instances, the conjugating moiety comprises a protein or a binding fragment thereof. In additional instances, the conjugating moiety comprises a peptide. In additional instances, the conjugating moiety comprises a nucleic acid. In additional instances, the conjugating moiety comprises a small molecule. In some cases, the conjugating moiety increases serum half-life, and/or improves stability. In some cases, the conjugating moiety reduces cytokine interaction with one or more cytokine receptor domains or subunits. In additional cases, the conjugating moiety blocks cytokine interaction of one or more cytokine domains or subunits to its cognate receptor(s). In some embodiments, cytokine conjugates described herein comprise multiple conjugating moieties. In some embodiments, a conjugating moiety is attached to an unnatural or natural amino acid in the cytokine peptide. In some embodiments, a cytokine conjugate comprises a conjugating moiety attached to a natural amino acid. In some embodiments, a cytokine conjugate is attached to an unnatural amino acid in the cytokine peptide. In some embodiments, a conjugating moiety is attached to the N or C terminal amino acid of the cytokine peptide. Various combinations sites are disclosed herein, for example, a first conjugating moiety is attached to an unnatural or natural amino acid in the cytokine peptide, and a second conjugating moiety is attached to the N or C terminal amino acid of the cytokine peptide. In some embodiments, a single conjugating moiety is attached to multiple residues of the cytokine peptide (e.g. a staple). In some embodiments, a conjugating moiety is attached to both the N and C terminal amino acids of the cytokine peptide.

Water-Soluble Polymers

In some embodiments, a conjugating moiety descried herein is a water-soluble polymer. In some instances, the water-soluble polymer is a nonpeptidic, nontoxic, and biocompatible. As used herein, a substance is considered biocompatible if the beneficial effects associated with use of the substance alone or with another substance (e.g., an active agent such as a cytokine moiety) in connection with living tissues (e.g., administration to a patient) outweighs any deleterious effects as evaluated by a clinician, e.g., a physician, a toxicologist, or a clinical development specialist. In some instances, a water-soluble polymer is further non-immunogenic. In some instances, a substance is considered non-immunogenic if the intended use of the substance in vivo does not produce an undesired immune response (e.g., the formation of antibodies) or, if an immune response is produced, that such a response is not deemed clinically significant or important as evaluated by a clinician, e.g., a physician, a toxicologist, or a clinical development specialist.

In some instances, the water-soluble polymer is characterized as having from about 2 to about 300 termini. Exemplary water soluble polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol) (PVA), polyacrylamide (PAAm), poly(N-(2-hydroxypropyl) methacrylamide) (PHPMA), polydimethylacrylamide (PDAAm), polyphosphazene, polyoxazolines ("POZ") (which are described in WO 2008/106186), poly(N-acryloylmorpholine), and combinations of any of the foregoing.

In some cases, the water-soluble polymer is not limited to a particular structure. In some cases, the water-soluble polymer is linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

In some embodiments, the weight-average molecular weight of the water-soluble polymer in the conjugate is from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120.000 Daltons.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8.000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

PEGs will typically comprise a number of $(OCH_2CH_2)$ monomers [or $(CH_2CH_2O)$ monomers, depending on how the PEG is defined]. As used herein, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In some instances, the water-soluble polymer is an end-capped polymer, that is, a polymer having at least one terminus capped with a relatively inert group, such as a lower $C_{1-6}$ alkoxy group, or a hydroxyl group. When the polymer is PEG, for example, a methoxy-PEG (commonly referred to as mPEG) may be used, which is a linear form of PEG wherein one terminus of the polymer is a methoxy ($—OCH_3$) group, while the other terminus is a hydroxyl or other functional group that can be optionally chemically modified.

In some embodiments, exemplary water-soluble polymers include, but are not limited to, linear or branched discrete PEG (dPEG) from Quanta Biodesign, Ltd; linear, branched, or forked PEGs from Nektar Therapeutics; and Y-shaped PEG derivatives from JenKem Technology.

In some embodiments, a cytokine (e.g., an interleukin, IFN, or TNF) polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly(N-acryloylmorpholine), and a combination thereof. In some instances, the cytokine polypeptide is conjugated to PEG (e.g., PEGylated). In some instances, the cytokine polypeptide is conjugated to PPG. In some instances, the cytokine polypeptide is conjugated to POZ. In some instances, the cytokine polypeptide is conjugated to PVP.

In some embodiments, an IL-2 polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly(N-acryloylmorpholine), and a combination thereof. In some instances, the IL-2 polypeptide is conjugated to PEG (e.g., PEGylated). In some instances, the IL-2 polypeptide is conjugated to PPG. In some instances, the IL-2 polypeptide is conjugated to POZ. In some instances, the IL-2 polypeptide is conjugated to PVP.

In some instances, a water-soluble polymer comprises a polyglycerol (PG). In some cases, the polyglycerol is a hyperbranched PG (HPG) (e.g., as described by Imran, et al. "Influence of architecture of high molecular weight linear and branched polyglycerols on their biocompatibility and biodistribution," *Biomaterials* 33:9135-9147 (2012)). In other cases, the polyglycerol is a linear PG (LPG). In additional cases, the polyglycerol is a midfunctional PG, a linear-block-hyperbranched PG (e.g., as described by Wurm et. Al., "Squaric acid mediated synthesis and biological activity of a library of linear and hyperbranched poly(glycerol)—protein conjugates," *Biomacromolecules* 13:1161-1171 (2012)), or a side-chain functional PG (e.g., as described by Li, et. al., "Synthesis of linear polyether polyol derivatives as new materials for bioconjugation," *Bioconjugate Chem.* 20:780-789 (2009).

In some instances, a cytokine (e.g., an interleukin, IFN, or TNF) polypeptide described herein is conjugated to a PG, e.g., a HPG, a LPG, a midfunctional PG, a linear-block-hyperbranched PG, or a side-chain functional PG. In some instances, the cytokine is an IL-2 polypeptide. In some cases, the IL-2 polypeptide is conjugated to a PG, a midfunctional PG, a linear-block-hyperbranched PG.

In some embodiments, a water-soluble polymer is a degradable synthetic PEG alternative. Exemplary degradable synthetic PEG alternatives include, but are not limited to, poly[oligo(ethylene glycol)methyl methacrylate] (POEGMA); backbone modified PEG derivatives generated by polymerization of telechelic, or di-end-functionalized PEG-based macromonomers; PEG derivatives comprising comonomers comprising degradable linkage such as poly[(ethylene oxie)-co-(methylene ethylene oxide)][P(EO-co-MEO)], cyclic ketene acetals such as 5,6-benzo-2-methylene-1,3-dioxepane (BMDO), 2-methylene-1,3-dioxepane (MDO), and 2-methylene-4-phenyl-1,3-dioxolane (MPDL) copolymerized with OEGMA; or poly-(ε-caprolactone)-graft-poly(ethylene oxide) (PCL-g-PEO).

In some instances, a cytokine (e.g., an interleukin, IFN, or TNF) polypeptide described herein is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO. In some instances, the cytokine is an IL-2 polypeptide. In some cases, the IL-2 polypeptide is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO.

In some embodiments, a water-soluble polymer comprises a poly(zwitterions). Exemplary poly(zwitterions) include, but are not limited to, poly(sulfobetaine methacrylate) (PSBMA), poly(carboxybetaine methacrylate) (PCBMA), and poly(2-methyacryloyloxyethyl phosphorylcholine) (PMPC). In some instances, a cytokine (e.g., an interleukin, IFN, or TNF) polypeptide described herein is conjugated to a poly(zwitterion) such as PSBMA, PCBMA, or PMPC. In some cases, the cytokine is an IL-2 polypeptide. In some cases, the IL-2 polypeptide is conjugated to a poly(zwitterion) such as PSBMA, PCBMA, or PMPC.

In some embodiments, a water-soluble polymer comprises a polycarbonate. Exemplary polycarbones include, but are not limited to, pentafluorophenyl 5-methyl-2-oxo-1,3-dioxane-5-carboxylate (MTC-OC$_6$F$_5$). In some instances, a cytokine (e.g., an interleukin, IFN, or TNF) polypeptide described herein is conjugated to a polycarbonate such as MTC-OC$_6$F$_5$. In some cases, the cytokine is an IL-2 polypeptide. In some cases, the IL-2 polypeptide is conjugated to a polycarbonate such as MTC-OC$_6$F$_5$.

In some embodiments, a water-soluble polymer comprises a polymer hybrid, such as for example, a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some instances, a cytokine (e.g., an interleukin, IFN, or TNF) polypeptide described herein is conjugated to a polymer hybrid such as a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some cases, the cytokine is an IL-2 polypeptide. In some cases, the IL-2 polypeptide is conjugated to a polymer hybrid such as a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer).

In some instances, a water-soluble polymer comprises a polysaccharide. Exemplary polysaccharides include, but are not limited to, dextran, polysialic acid (PSA), hyaluronic acid (HA), amylose, heparin, heparan sulfate (HS), dextrin, or hydroxyethyl-starch (HES). In some cases, a cytokine (e.g., an interleukin, IFN, or TNF) polypeptide is conjugated to a polysaccharide. In some cases, an IL-2 polypeptide is conjugated to dextran. In some cases, an IL-2 polypeptide is conjugated to PSA. In some cases, an IL-2 polypeptide is conjugated to HA. In some cases, an IL-2 polypeptide is conjugated to amylose. In some cases, an IL-2 polypeptide is conjugated to heparin. In some cases, an IL-2 polypeptide is conjugated to HS. In some cases, an IL-2 polypeptide is conjugated to dextrin. In some cases, an IL-2 polypeptide is conjugated to HES.

In some cases, a water-soluble polymer comprises a glycan. Exemplary classes of glycans include N-linked glycans, O-linked glycans, glycolipids, O-GlcNAc, and glycosaminoglycans. In some cases, a cytokine (e.g., an interleukin, IFN, or TNF) polypeptide is conjugated to a glycan. In some cases, an IL-2 polypeptide is conjugated to N-linked glycans. In some cases, an IL-2 polypeptide is conjugated to O-linked glycans. In some cases, an IL-2 polypeptide is conjugated to glycolipids. In some cases, an IL-2 polypeptide is conjugated to O-GlcNAc. In some cases, an IL-2 polypeptide is conjugated to glycosaminoglycans.

In some embodiments, a water-soluble polymer comprises a polyoxazoline polymer. A polyoxazoline polymer is a linear synthetic polymer, and similar to PEG, comprises a low polydispersity. In some instances, a polyoxazoline polymer is a polydispersed polyoxazoline polymer, characterized with an average molecule weight. In some cases, the average molecule weight of a polyoxazoline polymer includes, for example, 1000, 1500, 2000, 2500, 3000, 3500, 4000, 4500, 5000, 5500, 6000, 6500, 7000, 7500, 8000, 10,000, 12,000, 20,000, 35,000, 40,000, 50,000, 60,000, 100,000, 200,000, 300,000, 400,000, or 500,000 Da. In some instances, a polyoxazoline polymer comprises poly(2-methyl 2-oxazoline) (PMOZ), poly(2-ethyl 2-oxazoline) (PEOZ), or poly (2-propyl 2-oxazoline) (PPOZ). In some cases, a cytokine (e.g., an interleukin, IFN, or TNF) polypeptide is conjugated to a polyoxazoline polymer. In some cases, an IL-2 polypeptide is conjugated to a polyoxazoline polymer. In some cases, an IL-2 polypeptide is conjugated to PMOZ. In some cases, an IL-2 polypeptide is conjugated to PEOZ. In some cases, an IL-2 polypeptide is conjugated to PPOZ.

In some instances, a water-soluble polymer comprises a polyacrylic acid polymer. In some cases, a cytokine (e.g., an interleukin, IFN, or TNF) polypeptide is conjugated to a polyacrylic acid polymer. In some cases, an IL-2 polypeptide is conjugated to a polyacrylic acid polymer.

In some instances, a water-soluble polymer comprises polyamine. Polyamine is an organic polymer comprising two or more primary amino groups. In some embodiments, a polyamine includes a branched polyamine, a linear polyamine, or cyclic polyamine. In some cases, a polyamine is a low-molecular-weight linear polyamine. Exemplary polyamines include putrescine, cadaverine, spermidine, spermine, ethylene diamine, 1,3-diaminopropane, hexamethylenediamine, tetraethylmethylenediamine, and piperazine. In some cases, a cytokine (e.g., an interleukin, IFN, or TNF) polypeptide is conjugated to a polyamine. In some cases, an IL-2 polypeptide is conjugated to polyamine. In some cases, an IL-2 polypeptide is conjugated to putrescine, cadaverine, spermidine, spermine, ethylene diamine, 1,3-diaminopropane, hexamethylenediamine, tetraethylmethylenediamine, or piperazine.

In some instances, a water-soluble polymer is described in U.S. Pat. Nos. 7,744,861, 8,273,833, and 7,803,777. In some instances, a cytokine (e.g., an interleukin, IFN, or TNF) polypeptide is conjugated to a linker described in U.S. Pat. Nos. 7,744,861, 8,273,833, or 7,803,777. In some cases, an IL-2 polypeptide is conjugated to a linker described in U.S. Pat. Nos. 7,744,861, 8,273,833, or 7,803,777.

Proteins

In some embodiments, a conjugating moiety descried herein is a protein or a binding fragment thereof. Exemplary proteins include albumin, transferrin, or transthyretin. In some instances, the protein or a binding fragment thereof comprises an antibody, or its binding fragments thereof. In some cases, a cytokine conjugate comprises a protein or a binding fragment thereof. In some cases, an IL-2 conjugate comprising a protein or a binding fragment thereof has an increased serum half-life, and/or stability. In some cases, an IL-2 conjugate comprising a protein or a binding fragment thereof has a reduced IL-2 interaction with one or more IL-2R subunits. In additional cases, the protein or a binding fragment thereof blocks IL-2 interaction with one or more IL-2R subunits, or affects assembly of the IL-2Rβγ signaling complex.

In some embodiments, the conjugating moiety is albumin. Albumin is a family of water-soluble globular proteins. It is commonly found in blood plasma, comprising about 55-60% of all plasma proteins. Human serum albumin (HSA) is a 585 amino acid polypeptide in which the tertiary structure is divided into three domains, domain I (amino acid residues 1-195), domain II (amino acid residues 196-383), and domain III (amino acid residues 384-585). Each domain further comprises a binding site, which can interact either reversibly or irreversibly with endogenous ligands such as long- and medium-chain fatty acids, bilirubin, or hemin, or exogenous compounds such as heterocyclic or aromatic compounds.

In some cases, a cytokine (e.g., an interleukin, IFN, or TNF) polypeptide is conjugated to albumin. In some cases, the cytokine polypeptide is conjugated to human serum albumin (HSA). In additional cases, the cytokine polypeptide is conjugated to a functional fragment of albumin.

In some instances, an IL-2 polypeptide is conjugated to albumin. In some cases, the IL-2 polypeptide is conjugated to human serum albumin (HSA). In additional cases, the IL-2 polypeptide is conjugated to a functional fragment of albumin.

In some embodiments, the conjugating moiety is transferrin. Transferrin is a 679 amino acid polypeptide that is about 80 kDa in size and comprises two $Fe^{3+}$ binding sites with one at the N-terminal domain and the other at the C-terminal domain. In some instances, human transferrin has a half-life of about 7-12 days.

In some instances, a cytokine (e.g., an interleukin, IFN, or TNF) polypeptide is conjugated to transferrin. In some cases, the cytokine polypeptide is conjugated to human transferrin. In additional cases, the cytokine polypeptide is conjugated to a functional fragment of transferrin.

In some instances, an IL-2 polypeptide is conjugated to transferrin. In some cases, the IL-2 polypeptide is conjugated to human transferrin. In additional cases, the IL-2 polypeptide is conjugated to a functional fragment of transferrin.

In some embodiments, the conjugating moiety is transthyretin (TTR). Transthyretin is a transport protein located in the serum and cerebrospinal fluid which transports the thyroid hormone thyroxine ($T_4$) and retinol-binding protein bound to retinol.

In some instances, a cytokine (e.g., an interleukin, IFN, or TNF) polypeptide is conjugated to transthyretin (via one of its termini or via an internal hinge region). In some cases, the cytokine polypeptide is conjugated to a functional fragment of transthyretin.

In some instances, an IL-2 polypeptide is conjugated to transthyretin (via one of its termini or via an internal hinge region). In some cases, the IL-2 polypeptide is conjugated to a functional fragment of transthyretin.

In some embodiments, the conjugating moiety is an antibody, or its binding fragments thereof. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, the conjugating moiety comprises a scFv, bis-scFv, (scFv)$_2$, dsFv, or sdAb. In some cases, the conjugating moiety comprises a scFv. In some cases, the conjugating moiety comprises a bis-scFv. In some cases, the conjugating moiety comprises a (scFv)$_2$. In some cases, the conjugating moiety comprises a dsFv. In some cases, the conjugating moiety comprises a sdAb.

In some instances, the conjugating moiety comprises an Fc portion of an antibody, e.g., of IgG, IgA, IgM, IgE, or IgD. In some instances, the moiety comprises an Fc portion of IgG (e.g., IgG$_1$, IgG$_3$, or IgG$_4$).

In some cases, a cytokine (e.g., an interleukin, IFN, or TNF) polypeptide is conjugated to an antibody, or its binding fragments thereof. In some cases, the cytokine polypeptide is conjugated to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is conjugated to an Fc portion of an antibody. In additional cases, the cytokine polypeptide is conjugated to an Fc portion of IgG (e.g., IgG$_1$, IgG$_3$, or IgG$_4$).

In some cases, an IL-2 polypeptide is conjugated to an antibody, or its binding fragments thereof. In some cases, the IL-2 polypeptide is conjugated to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is conjugated to an Fc portion of an antibody. In additional cases, the IL-2 polypeptide is conjugated to an Fc portion of IgG (e.g., IgG$_1$, IgG$_3$, or IgG$_4$).

In some embodiments, an IL-2 polypeptide is conjugated to a water-soluble polymer (e.g., PEG) and an antibody or binding fragment thereof. In some cases, the antibody or binding fragments thereof comprises a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In some cases, the antibody or binding fragments thereof comprises a scFv, bis-scFv, (scFv)$_2$, dsFv, or sdAb. In some cases, the antibody or binding fragments thereof comprises a scFv. In some cases, the antibody or binding fragment thereof guides the IL-2 conjugate to a target cell of interest and the water-soluble polymer enhances stability and/or serum half-life.

In some instances, one or more IL-2 polypeptide—water-soluble polymer (e.g., PEG) conjugates are further bound to an antibody or binding fragments thereof. In some instances, the ratio of the IL-2 conjugate to the antibody is about 1:1, 2:1, 3:1, 4:1, 5:1, 6:1, 7:1, 8:1, 9:1, 10:1, 11:1, or 12:1. In some cases, the ratio of the IL-2 conjugate to the antibody is about 1:1. In other cases, the ratio of the IL-2 conjugate to the antibody is about 2:1, 3:1, or 4:1. In additional cases, the ratio of the IL-2 conjugate to the antibody is about 6:1 or higher.

In some embodiments, the one or more IL-2 polypeptide—water-soluble polymer (e.g., PEG) conjugates are directly bound to the antibody or binding fragments thereof. In other instances, the IL-2 conjugate is indirectly bound to the antibody or binding fragments thereof with a linker. Exemplary linkers include homobifunctional linkers, heterobifunctional linkers, maleimide-based linkers, zero-trace linkers, self-immolative linkers, spacers, and the like.

In some embodiments, the antibody or binding fragments thereof is bound either directly or indirectly to the IL-2 polypeptide portion of the IL-2 polypeptide—water-soluble polymer (e.g., PEG) conjugate. In such cases, the conjugation site of the antibody to the IL-2 polypeptide is at a site that will not impede binding of the IL-2 polypeptide with the IL-2Rβγ. In additional cases, the conjugation site of the antibody to the IL-2 polypeptide is at a site that partially blocks binding of the IL-2 polypeptide with the IL-2Rβγ. In other embodiments, the antibody or binding fragments thereof is bound either directly or indirectly to the water-soluble polymer portion of the IL-2 polypeptide—water-soluble polymer (e.g., PEG) conjugate.

Peptides

In some embodiments, a conjugating moiety descried herein is a peptide. In some instances, the peptide is a non-structured peptide. In some cases, a cytokine (e.g., an interleukin, IFN, or TNF) polypeptide is conjugated to a peptide. In some cases, the IL-2 conjugate comprising a peptide has an increased serum half-life, and/or stability. In some cases, the IL-2 conjugate comprising a peptide has a reduced IL-2 interaction with one or more IL-2R subunits. In additional cases, the peptide blocks IL-2 interaction with one or more IL-2R subunits.

In some instances, the conjugating moiety is a XTEN™ peptide (Amunix Operating Inc.) and the modification is referred to as XTENylation. XTENylation is the genetic fusion of a nucleic acid encoding a polypeptide of interest with a nucleic acid encoding a XTEN™ peptide (Amunix Operating Inc.), a long unstructured hydrophilic peptide comprising different percentage of six amino acids: Ala, Glu, Gly, Ser, and Thr. In some instances, a XTEN™ peptide is selected based on properties such as expression, genetic stability, solubility, aggregation resistance, enhanced half-life, increased potency, and/or increased in vitro activity in combination with a polypeptide of interest. In some cases, a cytokine (e.g., an interleukin, IFN, or TNF) polypeptide is conjugated to a XTEN peptide. In some cases, an IL-2 polypeptide is conjugated to a XTEN peptide.

In some instances, the conjugating moiety is a glycine-rich homoamino acid polymer (HAP) and the modification is referred to as HAPylation. HAPylation is the genetic fusion of a nucleic acid encoding a polypeptide of interest with a nucleic acid encoding a glycine-rich homoamino acid polymer (HAP). In some instances, the HAP polymer comprises a $(Gly_4Ser)_n$ repeat motif (SEQ ID NO: 3) and sometimes are about 50, 100, 150, 200, 250, 300, or more residues in length. In some cases, a cytokine (e.g., an interleukin, IFN, or TNF) polypeptide is conjugated to HAP. In some cases, an IL-2 polypeptide is conjugated to HAP.

In some embodiments, the conjugating moiety is a PAS polypeptide and the modification is referred to as PASylation. PASylation is the genetic fusion of a nucleic acid encoding a polypeptide of interest with a nucleic acid encoding a PAS polypeptide. A PAS polypeptide is a hydrophilic uncharged polypeptide consisting of Pro, Ala and Ser residues. In some instances, the length of a PAS polypeptide is at least about 100, 200, 300, 400, 500, or 600 amino acids. In some cases, a cytokine (e.g., an interleukin, IFN, or TNF) polypeptide is conjugated to a PAS polypeptide. In some cases, an IL-2 polypeptide is conjugated to a PAS polypeptide.

In some embodiments, the conjugating moiety is an elastin-like polypeptide (ELP) and the modification is referred to as ELPylation. ELPylation is the genetic fusion of a nucleic acid encoding a polypeptide of interest with a nucleic acid encoding an elastin-like polypeptide (ELPs). An ELP comprises a VPGxG repeat motif (SEQ ID NO: 4) in which x is any amino acid except proline. In some cases, a cytokine (e.g., an interleukin, IFN, or TNF) polypeptide is conjugated to ELP. In some cases, an IL-2 polypeptide is conjugated to ELP.

In some embodiments, the conjugating moiety is a CTP peptide. A CTP peptide comprises a 31 amino acid residue peptide FQSSSS*KAPPPS*LPSPS*RLPGPS*DTPILPQ (SEQ ID NO: 5) in which the S* denotes O-glycosylation sites (OPKO). In some instances, a CTP peptide is genetically fused to a cytokine polypeptide (e.g., an IL-2 polypeptide). In some cases, a cytokine polypeptide (e.g., an IL-2 polypeptide) is conjugated to a CTP peptide.

In some embodiments, a cytokine (e.g., an IL-2 polypeptide) is modified by glutamylation. Glutamylation (or polyglutamylation) is a reversible posttranslational modification of glutamate, in which the γ-carboxy group of glutamate forms a peptide-like bond with the amino group of a free glutamate in which the α-carboxy group extends into a polyglutamate chain.

In some embodiments, a cytokine (e.g., an IL-2 polypeptide) is modified by a gelatin-like protein (GLK) polymer. In some instances, the GLK polymer comprises multiple repeats of Gly-Xaa-Yaa wherein Xaa and Yaa primarily comprise proline and 4-hydroxyproline, respectively. In some cases, the GLK polymer further comprises amino acid residues Pro, Gly, Glu, Qln, Asn, Ser, and Lys. In some cases, the length of the GLK polymer is about 20, 30, 40, 50, 60, 70, 80, 90, 100, 110, 120, 150 residues or longer.

Additional Conjugating Moieties

In some instances, the conjugating moiety comprises an extracellular biomarker. In some instances, the extracellular biomarker is a tumor antigen. In some instances, exemplary extracellular biomarker comprises CD19, PSMA, B7-H3, B7-H6, CD70, CEA, CSPG4, EGFRvIII, EphA3, EpCAM, EGFR, ErbB2 (HER2), FAP, FRa, GD2, GD3, Lewis-Y, mesothelin, Mucl, Muc 16, ROR1, TAG72, VEGFR2, CD11, Gr-1, CD204, CD16, CD49b, CD3, CD4, CD8, and B220. In some instances, the conjugating moiety is bond or conjugated to the cytokine (e.g., IL-2). In some cases, the conjugating moiety is genetically fused, for example, at the N-terminus or the C-terminus, of the cytokine (e.g., IL-2).

In some instances, the conjugating moiety comprises a molecule from a post-translational modification. In some instances, examples of post-translational modification include myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation. In some instances, the cytokine (e.g., IL-2) is modified by a post-translational modification such as myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation.

Conjugation

Linkers

In some embodiments, useful functional reactive groups for conjugating or binding a conjugating moiety to a cytokine polypeptide (e.g., an IL-2 polypeptide) described herein include, for example, zero or higher-order linkers. In some instances, an unnatural amino acid incorporated into an interleukin described herein comprises a functional reactive group. In some instances, a linker comprises a functional reactive group that reacts with an unnatural amino acid incorporated into an interleukin described herein. In some instances, a conjugating moiety comprises a functional reactive group that reacts with an unnatural amino acid incorporated into an interleukin described herein. In some instances, a conjugating moiety comprises a functional reactive group that reacts with a linker (optionally pre-attached to a cytokine peptide) described herein. In some embodiments, a linker comprises a reactive group that reacts with a natural amino acid in a cytokine peptide described herein. In some cases, higher-order linkers comprise bifunctional linkers, such as homobifunctional linkers or heterobifunctional linkers. Exemplary homobifuctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMI-1), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the bifunctional linker comprises a heterobifunctional linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl) butyrate (sulfo-sMPB), N-(γ-maleimidobutyryloxy) succinimide ester (GMBs), N-(γ-maleimidobutyryloxy) sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino) methyl)cyclohexane-1-carbonyl)amino) hexanoate (sIACX), ρ-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido) ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino) hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1, 3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido)butyl]-31-(2'-pyridyldithio) propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(p-azidosalicylamido)butylamine (AsBA), and arginine-reactive and photoreactive cross-linkers such as ρ-azidophenyl glyoxal (APG).

In some instances, the reactive functional group comprises a nucleophilic group that is reactive to an electrophilic group present on a binding moiety (e.g., on a conjugating moiety or on IL-2). Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker is a cleavable linker. In some embodiments, the cleavable linker is a dipeptide linker. In some embodiments, the dipeptide linker is valine-citrulline (Val-Cit), phenylalanine-lysine (Phe-Lys), valine-alanine (Val-Ala) and valine-lysine (Val-Lys). In some embodiments, the dipeptide linker is valine-citrulline.

In some embodiments, the linker is a peptide linker comprising, e.g., at least 2, 3, 4, 5, 6, 7, 8, 9, 10, 11, 12, 15, 20, 25, 30, 35, 40, 45, 50, or more amino acids. In some instances, the peptide linker comprises at most 2, 3, 4, 5, 6, 7, 8, 9, 10, 11, 12, 15, 20, 25, 30, 35, 40, 45, 50, or less amino acids. In additional cases, the peptide linker comprises about 2, 3, 4, 5, 6, 7, 8, 9, 10, 11, 12, 15, 20, 25, 30, 35, 40, 45, or 50 amino acids.

In some embodiments, the linker comprises a self-immolative linker moiety. In some embodiments, the self-immolative linker moiety comprises p-aminobenzyl alcohol (PAB), p-aminobenzyoxycarbonyl (PABC), or derivatives or analogs thereof. In some embodiments, the linker comprises a dipeptide linker moiety and a self-immolative linker moiety. In some embodiments, the self-immolative linker moiety is such as described in U.S. Pat. No. 9,089,614 and WIPO Application No. WO2015038426.

In some embodiments, the cleavable linker is glucuronide. In some embodiments, the cleavable linker is an acid-cleavable linker. In some embodiments, the acid-cleavable linker is hydrazine. In some embodiments, the cleavable linker is a reducible linker.

In some embodiments, the linker comprises a maleimide group. In some instances, the maleimide group is also referred to as a maleimide spacer. In some instances, the maleimide group further comprises a caproic acid, forming maleimidocaproyl (mc). In some cases, the linker comprises maleimidocaproyl (mc). In some cases, linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

Conjugation Chemistry

Various conjugation reactions are used to conjugate linkers, conjugation moieties, and unnatural amino acids incorporated into cytokine peptides described herein. Such conjugation reactions are often compatible with aqueous conditions, such as "bioorthogonal" reactions. In some embodiments, conjugation reactions are mediated by chemical reagents such as catalysts, light, or reactive chemical groups found on linkers, conjugation moieties, or unnatural amino acids. In some embodiments, conjugation reactions are mediated by enzymes. In some embodiments, a conjugation reaction used herein is described in Gong, Y., Pan, L. Tett. Lett. 2015, 56, 2123. In some embodiments, a conjugation reaction used herein is described in Chen, X.; Wu. Y-W. Org. Biomol. Chem. 2016, 14, 5417.

In some embodiments described herein, a conjugation reaction comprises reaction of a ketone or aldehyde with a nucleophile. In some embodiments, a conjugation reaction comprises reaction of a ketone with an aminoxy group to form an oxime. In some embodiments, a conjugation reaction comprises reaction of a ketone with an aryl or heteroaryl amine group to form an imine. In some embodiments, a conjugation reaction comprises reaction of an aldehyde with an aryl or heteroaryl amine group to form an imine. In some embodiments, a conjugation reaction described herein results in cytokine peptide comprising a linker or conjugation moiety attached via an oxime. In some embodiments, a conjugation reaction comprises a Pictet-Spengler reaction of an aldehyde or ketone with a tryptamine nucleophile. In some embodiments, a conjugation reaction comprises a hydrazino-Pictet-Spengler reaction. In some embodiments, a conjugation reaction comprises a Pictet-Spengler ligation.

In some embodiments described herein, a conjugation reaction described herein comprises reaction of an azide and a phosphine (Staudinger ligation). In some embodiments, the phosphine is an aryl phosphine. In some embodiments, the aryl phosphine comprises an ortho ester group. In some embodiments, the phosphine comprises the structure methyl 2-(diphenylphosphaneyl)benzoate. In some embodiments, a conjugation reaction described herein results in cytokine peptide comprising a linker or conjugation moiety attached via an arylamide. In some embodiments, a conjugation reaction described herein results in cytokine peptide comprising a linker or conjugation moiety attached via an amide.

In some embodiments described herein, a conjugation reaction described herein comprises a 1,3-dipolar cycloaddition reaction. In some embodiments, the 1,3-dipolar cycloaddition reaction comprises reaction of an azide and a phosphine ("Click" reaction). In some embodiments, the conjugation reaction is catalyzed by copper. In some embodiments, a conjugation reaction described herein results in cytokine peptide comprising a linker or conjugation moiety attached via a triazole. In some embodiments, a conjugation reaction described herein comprises reaction of an azide with a strained olefin. In some embodiments, a conjugation reaction described herein comprises reaction of an azide with a strained alkyne. In some embodiments, a conjugation reaction described herein comprises reaction of an azide with a cycloalkyne, for example, OCT, DIFO, DIFBO, DIBO, BARAC, TMTH, or other strained cycloalkyne, the structures of which are shown in Gong, Y., Pan, L. Tett. Lett. 2015, 56, 2123. In some embodiments, a 1,3-dipolar cycloaddition reaction is catalyzed by light ("photoclick"). In some embodiments, a conjugation reaction described herein comprises reaction of a terminal allyl group with a tetrazole and light. In some embodiments, a conjugation reaction described herein comprises reaction of a terminal alkynyl group with a tetrazole and light. In some embodiments, a conjugation reaction described herein comprises reaction of an O-allyl amino acid with a tetrazine and light. In some embodiments, a conjugation reaction described herein comprises reaction of O-allyl tyrosine with a tetrazine and light.

In some embodiments described herein, a conjugation reaction described herein comprises an inverse-electron demand cycloaddition reaction comprising a diene and a dienophile. In some embodiments, the diene comprises a tetrazine. In some embodiments, the dienophile comprises an alkene. In some embodiments, the dienophile comprises an alkyne. In some embodiments, the alkyne is a strained alkyne. In some embodiments, the alkene is a strained diene. In some embodiments, the alkyne is a trans-cyclooctyne. In some embodiments, the alkyne is a cyclooctene. In some embodiments, the alkene is a cyclopropene. In some embodiments, the alkene is a fluorocyclopropene. In some embodiments, a conjugation reaction described herein results in the formation of a cytokine peptide attached to a linker or conjugation moiety via a 6-membered ring heterocycle comprising two nitrogen atoms in the ring.

In some embodiments described herein, a conjugation reaction described herein comprises an olefin metathesis reaction. In some embodiments, a conjugation reaction described herein comprises reaction of an alkene and an alkyne with a ruthenium catalyst. In some embodiments, a conjugation reaction described herein comprises reaction of two alkenes with a ruthenium catalyst. In some embodiments, a conjugation reaction described herein comprises reaction of two alkynes with a ruthenium catalyst. In some embodiments, a conjugation reaction described herein comprises reaction of an alkene or alkyne with a ruthenium catalyst and an amino acid comprising an allyl group. In some embodiments, a conjugation reaction described herein comprises reaction of an alkene or alkyne with a ruthenium catalyst and an amino acid comprising an allyl sulfide or selenide. In some embodiments, a ruthenium catalyst is Hoveda-Grubbs $2^{nd}$ generation catalyst. In some embodiments, an olefin metathesis reaction comprises reaction of one or more strained alkenes or alkynes.

In some embodiments described herein, a conjugation reaction described herein comprises a cross-coupling reaction. In some embodiments, cross-coupling reactions comprise transition metal catalysts, such as iridium, gold, ruthenium, rhodium, palladium, nickel, platinum, or other transition metal catalyst and one or more ligands. In some embodiments, transition metal catalysts are water-soluble. In some embodiments described herein, a conjugation reaction described herein comprises a Suzuki-Miyaura cross-coupling reaction. In some embodiments described herein, a conjugation reaction described herein comprises reaction of an aryl halide (or triflate, or tosylate), an aryl or alkenyl boronic acid, and a palladium catalyst. In some embodiments described herein, a conjugation reaction described herein comprises a Sonogashira cross-coupling reaction. In some embodiments described herein, a conjugation reaction described herein comprises reaction of an aryl halide (or triflate, or tosylate), an alkyne, and a palladium catalyst. In some embodiments, cross-coupling reactions result in attachment of a linker or conjugating moiety to a cytokine peptide via a carbon-carbon bond.

In some embodiments described herein, a conjugation reaction described herein comprises a deprotection or "uncaging" reaction of a reactive group prior to conjugation. In some embodiments, a conjugation reaction described herein comprises uncaging of a reactive group with light, followed by a conjugation reaction. In some embodiments, a reactive group is protected with an aralkyl moiety comprising one or more nitro groups. In some embodiments, uncaging of a reactive group results in a free amine, sulfide, or other reactive group. In some embodiments, a conjugation reaction described herein comprises uncaging of a reactive group with a transition metal catalyst, followed by a conjugation reaction. In some embodiments, the transition metal catalyst comprises palladium and one or more ligands. In some embodiments, a reactive group is protected with an allyl moiety. In some embodiments, a reactive group is protected with an allylic carbamate. In some embodiments, a reactive group is protected with a propargylic moiety. In some embodiments, a reactive group is protected with a propargyl carbamate. In some embodiments, a reactive group is protected with a dienophile, wherein exposure to a diene (such as a tetrazine) results in deprotection of the reactive group.

In some embodiments described herein, a conjugation reaction described herein comprises a ligand-directed reaction, wherein a ligand (optionally) attached to a reactive group) facilitates the site of conjugation between the reactive group and the cytokine peptide. In some embodiments, the ligand is cleaved during or after reaction of the cytokine peptide with the reactive group. In some embodiments, the conjugation site of the cytokine peptide is a natural amino acid. In some embodiments, the conjugation site of the cytokine peptide is a lysine, cysteine, or serine. In some embodiments, the conjugation site of the cytokine peptide is an unnatural amino acid described herein. In some embodiments the reactive group comprises a leaving group, such as an electron-poor aryl or heteroaryl group. In some embodiments the reactive group comprises a leaving group, such as an electron-poor alkyl group that is displaced by the cytokine peptide. In some embodiments, a conjugation reaction described herein comprises reaction of a radical trapping agent with a radical species. In some embodiments, a conjugation reaction described herein comprises an oxidative radical addition reaction. In some embodiments, a radical trapping agent is an arylamine. In some embodiments, a radical species is a tyrosyl radical. In some embodiments, radical species are generated by a ruthenium catalyst (such as [Ru(bpy)$_3$]) and light.

Enzymatic reactions are optionally used for conjugation reactions described herein. Exemplary enzymatic conjugations include SortA-mediated conjugation, a TGs-mediated conjugation, or an FGE-mediated conjugation. In some embodiments, a conjugation reaction described herein comprises native protein ligation (NPL) of a terminal 1-amino-2-thio group with a thioester to form an amide bond.

Various conjugation reactions are described herein for reacting a linker or conjugating moiety with a cytokine peptide, wherein the reaction occurs with a natural ("canonical") amino acid in the cytokine peptide. In some embodiments, the natural amino acid is found at a conjugation position is found in a wild type sequence, or alternatively the position has been mutated. In some embodiments, a conjugation reaction comprises formation of a disulfide bond at a cysteine residue. In some embodiments, a conjugation reaction comprises a 1,4 Michael addition reaction of a cysteine or lysine. In some embodiments, a conjugation reaction comprises a cyanobenzothiazole ligation of a cysteine. In some embodiments, a conjugation reaction comprises cross-linking with an acetone moiety, such as 1,3-dichloro-2-propionone. In some embodiments, a conjugation reaction comprises a 1,4 Michael addition to a dehydroalanine, formed by reaction of cysteine with O-mesitylenesulfonyl-hydroxylamine. In some embodiments a conjugation reaction comprises reaction of a tyrosine with a triazolinedione (TAD), or TAD derivative. In some embodiments a conjugation reaction comprises reaction of a tryptophan with a rhodium carbenoid.

Methods of Use

Autoimmune Disease or Disorder

In some embodiments, also described herein is a method of treating an autoimmune disease or disorder in a subject in need thereof, which comprises administering to the subject a therapeutically effective amount of a cytokine conjugate (e.g., IL-2 conjugate) described herein. In some instances, the IL-2 conjugate comprises an isolated and purified IL-2 polypeptide and a conjugating moiety, wherein the IL-2 conjugate has a decreased affinity to IL-2 receptor β (IL-2Rβ) subunit, IL-2 receptor γ (IL-2Rγ) subunit, or a combination thereof, relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid residue selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, 5127, S130, T131, L132, and T133, wherein the numbering of the amino acid residues corresponds to SEQ ID NO: 1. In some instances, the amino acid residue is selected from K8, K9, Q11, L12, E15, H16, L18, L19, D20, Q22, M23, N26, R81, D84, S87, N88, V91, I92, L94, E95, E116, N119, R120, T123, A125, Q126, 5127, 5130, T131, L132, and T133. In some instances, the amino acid residue is selected from K8, K9, L12, E15, H16, L19, D20, Q22, M23, N26, D84, N88, E95, and Q126. In some cases, the IL-2 conjugate interacts with an IL-2Rαβγ complex but with a reduced affinity toward the IL-2Rβ and IL-2Rγ subunits, or will decrease the recruitment of the IL-2R γ subunit to the IL-2/IL-2Rβ complex. In some cases, the modified IL-2 polypeptide maintains the binding affinity toward IL-2Rα relative to a wild-type IL-2 polypeptide. In such cases, the IL-2/IL-2Rαβγ complex stimulates or enhances expansion of CD4+ Treg cells. In additional cases, the modified IL-2 polypeptide increases the dose required for activation of the Teff and/or NK cells via the IL-2Iβγ complex, thereby expanding the dose ranges for activation of Treg cells via the IL-2Rαβγ complex (or expanding the therapeutic window of the IL-2 for activation of Treg cells via the IL-2Rαβγ complex).

In some instances, the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

In some cases, a cytokine (e.g., interleukin, IFN, or TNF) conjugate is administered to a subject having alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

In some cases, an IL-2 conjugate is administered to a subject having alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis. In some cases, the IL-2 conjugate is administered to a subject having type 1 diabetes. In some cases, the IL-2 conjugate is administered to a subject having Graves' disease. In some cases, the IL-2 conjugate is administered to a subject having multiple sclerosis. In some cases, the IL-2 conjugate is administered to a subject having psoriasis. In some cases, the IL-2 conjugate is administered to a subject having rheumatoid arthritis. In some cases, the IL-2 conjugate is administered to a subject having Sjögren's syndrome. In some cases, the IL-2 conjugate is administered to a subject having systemic lupus erythematosus. In some cases, the IL-2 conjugate is administered to a subject having uveitis. In some cases, the IL-2 conjugate is administered to a subject having Wegener's granulomatosis.

In some cases, a cytokine conjugate (e.g., an IL-2 conjugate) is administered to a subject for the treatment of a Graft-versus-Host disease (GVHD).

In some embodiments, an additional therapeutic agent is further administered to the subject. In some cases, the additional therapeutic agent is administered simultaneously with a cytokine conjugate (e.g., IL-2 conjugate). In other cases, the additional therapeutic agent and the cytokine conjugate (e.g., IL-2 conjugate) are administered sequentially, e.g., the cytokine conjugate (e.g., IL-2 conjugate) is administered prior to the additional therapeutic agent or that the cytokine conjugate (e.g., IL-2 conjugate) is administered after administration of the additional therapeutic agent.

Exemplary additional therapeutic agents for the treatment of an autoimmune disease or disorder include, but are not limited to, corticosteroids such as prednisone, budesonide, or prednisolone; calcineurin inhibitors such as cyclosporine or tacrolimus; mTOR inhibitors such as sirolimus or everolimus; IMDH inhibitors such as azathioprine, leflunomide, or mycophenolate; biologics such as abatacept, adalimumab, anakinra, certolizumab, etanercept, golimumab, infliximab, ixekizumab, natalizumab, rituximab, secukinumab, tocilizumab, ustekinumab, or vedolizumab; and monoclonal antibodies such as basiliximab, daclizumab, or muromonab.

In some cases, a cytokine conjugate (e.g., IL-2 conjugate) is administered with an additional therapeutic agent selected from a corticosteroid such as prednisone, budesonide, or prednisolone; a calcineurin inhibitor such as cyclosporine or tacrolimus; an mTOR inhibitor such as sirolimus or everolimus; an IMDH inhibitor such as azathioprine, leflunomide, or mycophenolate; a biologics such as abatacept, adalimumab, anakinra, certolizumab, etanercept, golimumab, infliximab, ixekizumab, natalizumab, rituximab, secukinumab, tocilizumab, ustekinumab, or vedolizumab; and a monoclonal antibody such as basiliximab, daclizumab, or muromonab.

Methods of Cell Population Expansion

In some embodiments, additionally described herein are methods of expanding a Treg cell population. In some instances, the method comprises contacting a cell with a cytokine conjugate described herein, and interacting the cytokine with a cytokine receptor to form a complex, wherein the complex stimulates expansion of a distinct lymphocyte population.

In some embodiments, the method of expanding CD4+ regulatory T (Treg) cell population comprise contacting a cell with an isolated and modified IL-2 polypeptide described above for a time sufficient to induce formation of a complex with an IL-2Rαβγ, thereby stimulating the expansion of the Treg cell population. In some embodiments, the method of expanding a CD4+ Treg cell population comprises (a) contacting a cell with an IL-2 conjugate described herein; and (b) interacting the IL-2 conjugate with IL-2Rα, IL-2Rβ, and IL-2Rγ subunits to form an IL-2/IL-2Rαβγ complex; wherein the IL-2 conjugate has a decreased affinity to IL-2Rβ and IL-2Rγ subunits, or decreases the recruitment of the IL-2Rγ subunit to the IL-2/IL-2Rβ complex, and wherein the IL-2/IL-2Rαβγ complex stimulates the expansion of Treg cells. In some instances, the IL-2 conjugate comprises an isolated and purified IL-2 polypeptide; and a conjugating moiety that binds to the isolated and purified IL-2 polypeptide at an amino acid residue selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, 5127, 5130, T131, L132, and T133, wherein the numbering of the amino acid residues corresponds to SEQ ID NO: 1. In some instances, the amino acid residue is selected from K8, K9, Q11, L12, E15, H16, L18, L19, D20, Q22, M23, N26, R81, D84, S87, N88, V91, I92, L94, E95, E116, N119, R120, T123, A125, Q126, 5127, 5130, T131, L132, and T133. In some instances, the amino acid residue is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113. In some instances, the amino acid position is selected from K8, K9, L12, E15, H16, L19, D20, Q22, M23, N26, D84, N88, E95, and Q126. In some instances, the amino acid position is selected from K8, K9, and H16. In some instances, the amino acid position is selected from Q22, N26, N88, and Q126. In some instances, the amino acid position is selected from E15, D20, D84, and E95. In some instances, the amino acid position is selected from L12, L19, M23, and F78. In some instances, the amino acid position is selected from Q22 and N26.

In some instances, the IL-2 conjugate expands CD4+T regulatory (Treg) cells by at least 10%, 20%, 30%, 40%, 50%, 60%, 70%, 80%, 90%, 95%, 99%, or greater. In some isntances, the IL-2 conjugate expands CD4+T regulatory (Treg) cells by about 10%, 20%, 30%, 40%, 50%, 60%, 70%, 80%, 90%, 95%, 99%, or greater.

In some cases, the IL-2 conjugate expands CD4+T regulatory (Treg) cells by at least 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 1000-fold, or more. In some cases, the IL-2 conjugate expands CD4+T regulatory (Treg) cells by about 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 1000-fold, or more.

In some instances, the time sufficient to induce formation of a complex with an IL-2Rαβγ is at least 5 minutes, 10 minutes, 15 minutes, 20 minutes, 30 minutes, 1 hour, 2 hours, 3 hours, 4 hours, 5 hours, 8 hours, 10 hours, 12 hours, 18 hours, 24 hours, 2 days, 3 days, 4 days, 5 days, 6 days, or 7 days. In some instances, the time sufficient to induce formation of a complex with an IL-2Rαβγ is about 5 minutes, 10 minutes, 15 minutes, 20 minutes, 30 minutes, 1 hour, 2 hours, 3 hours, 4 hours, 5 hours, 8 hours, 10 hours, 12 hours, 18 hours, 24 hours, 2 days, 3 days, 4 days, 5 days, 6 days, or 7 days.

In some embodiments, the method is an in vivo method.

In other embodiments, the method is an in vitro method.

In additional embodiments, the method is an ex vivo method.

Cytokine Polypeptide Production

In some instances, the cytokine (e.g., interleukin, IFN, or TNF) polypeptides described herein, either containing a natural amino acid mutation or an unnatural amino acid mutation, are generated recombinantly or are synthesized chemically. In some instances, the cytokine (e.g., IL-2) polypeptides described herein are generated recombinantly, for example, either by a host cell system, or in a cell-free system.

In some instances, the cytokine (e.g., IL-2) polypeptides are generated recombinantly through a host cell system. In some cases, the host cell is a eukaryotic cell (e.g., mammalian cell, insect cells, yeast cells or plant cell) or a prokaryotic cell (e.g., gram-positive bacterium or a gram-negative bacterium). In some cases, a eukaryotic host cell is a mammalian host cell. In some cases, a mammalian host cell is a stable cell line, or a cell line that has incorporated a genetic material of interest into its own genome and has the capability to express the product of the genetic material after many generations of cell division. In other cases, a mammalian host cell is a transient cell line, or a cell line that has not incorporated a genetic material of interest into its own genome and does not have the capability to express the product of the genetic material after many generations of cell division.

Exemplary mammalian host cells include 293T cell line, 293A cell line, 293FT cell line, 293F cells, 293 H cells, A549 cells, MDCK cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some embodiments, an eukaryotic host cell is an insect host cell. Exemplary insect host cell include Drosophila S2 cells, 519 cells, Sf21 cells, High Five™ cells, and expresSF+® cells.

In some embodiments, a eukaryotic host cell is a yeast host cell. Exemplary yeast host cells include Pichia pastoris yeast strains such as GS115, KM71H, SMD1168, SMD1168H, and X-33, and Saccharomyces cerevisiae yeast strain such as INVSc1.

In some embodiments, a eukaryotic host cell is a plant host cell. In some instances, the plant cells comprise a cell from algae. Exemplary plant cell lines include strains from Chlamydomonas reinhardtii 137c, or Synechococcus elongatus PPC 7942.

In some embodiments, a host cell is a prokaryotic host cell. Exemplary prokaryotic host cells include BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, suitable polynucleic acid molecules or vectors for the production of an IL-2 polypeptide described herein include any suitable vectors derived from either a eukaryotic or prokaryotic source. Exemplary polynucleic acid molecules or vectors include vectors from bacteria (e.g., E. coli), insects, yeast (e.g., Pichia pastoris), algae, or mammalian source. Bacterial vectors include, for example, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Insect vectors include, for example, pFastBacl, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

Yeast vectors include, for example, Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pA0815 Pichia vector, pFLD1 Pichi pastoris vector, pGAPZA, B, & C Pichia pastoris vector, pPIC3.5K Pichia vector, pPIC6 Å, B, & C Pichia vector, pPIC9K Pichia vector, pTEF1/Zeo, pYES2 yeast vector, pYES2/CT yeast vector, pYES2/NT A, B, & C yeast vector, or pYES3/CT yeast vector.

Algae vectors include, for example, pChlamy-4 vector or MCS vector.

Mammalian vectors include, for example, transient expression vectors or stable expression vectors. Exemplary mammalian transient expression vectors include p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Exemplary mammalian stable expression vectors include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is used for the production of a cytokine (e.g., IL-2) polypeptide described herein. In some cases, a cell-free system comprises a mixture of cytoplasmic and/or nuclear components from a cell and is suitable for in vitro nucleic acid synthesis. In some instances, a cell-free system utilizes prokaryotic cell components. In other instances, a cell-free system utilizes eukaryotic cell components. Nucleic acid synthesis is obtained in a cell-free system based on, for example, Drosophila cell, Xenopus egg, Archaea, or HeLa cells. Exemplary cell-free systems include E. coli S30 Extract system, E. coli T7 S30 system, or PURExpress®, XpressCF, and XpressCF+.

Cell-free translation systems variously comprise components such as plasmids, mRNA, DNA, tRNAs, synthetases, release factors, ribosomes, chaperone proteins, translation initiation and elongation factors, natural and/or unnatural amino acids, and/or other components used for protein expression. Such components are optionally modified to improve yields, increase synthesis rate, increase protein product fidelity, or incorporate unnatural amino acids. In some embodiments, cytokines described herein are synthesized using cell-free translation systems described in U.S. Pat. No. 8,778,631; US 2017/0283469; US 2018/0051065; US 2014/0315245; or U.S. Pat. No. 8,778,631. In some embodiments, cell-free translation systems comprise modified release factors, or even removal of one or more release factors from the system. In some embodiments, cell-free translation systems comprise a reduced protease concentration. In some embodiments, cell-free translation systems comprise modified tRNAs with re-assigned codons used to code for unnatural amino acids. In some embodiments, the synthetases described herein for the incorporation of unnatural amino acids are used in cell-free translation systems. In some embodiments, tRNAs are pre-loaded with unnatural amino acids using enzymatic or chemical methods before being added to a cell-free translation system. In some embodiments, components for a cell-free translation system are obtained from modified organisms, such as modified bacteria, yeast, or other organism.

In some embodiments, a cytokine (e.g., IL-2) polypeptide is generated as a circularly permuted form, either via an expression host system or through a cell-free system.

Production of Cytokine Polypeptide Comprising an Unnatural Amino Acid

An orthogonal or expanded genetic code can be used in the present disclosure, in which one or more specific codons present in the nucleic acid sequence of a cytokine (e.g., IL-2) polypeptide are allocated to encode the unnatural amino acid so that it can be genetically incorporated into the cytokine (e.g., IL-2) by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

In some instances, the codon is the codon amber, ochre, opal or a quadruplet codon. In some cases, the codon corresponds to the orthogonal tRNA which will be used to carry the unnatural amino acid. In some cases, the codon is amber. In other cases, the codon is an orthogonal codon.

In some instances, the codon is a quadruplet codon, which can be decoded by an orthogonal ribosome ribo-Q1. In some cases, the quadruplet codon is as illustrated in Neumann, et al., "Encoding multiple unnatural amino acids via evolution of a quadruplet-decoding ribosome," *Nature*, 464(7287): 441-444 (2010).

In some instances, a codon used in the present disclosure is a recoded codon, e.g., a synonymous codon or a rare codon that is replaced with alternative codon. In some cases, the recoded codon is as described in Napolitano, et al., "Emergent rules for codon choice elucidated by editing rare argine codons in *Escherichia coli*," *PNAS*, 113(38): E5588-5597 (2016). In some cases, the recoded codon is as described in Ostrov et al., "Design, synthesis, and testing toward a 57-codon genome," *Science* 353(6301): 819-822 (2016).

In some instances, unnatural nucleic acids are utilized leading to incorporation of one or more unnatural amino acids into the cytokine (e.g., IL-2). Exemplary unnatural nucleic acids include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CH$_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thio-guanine, 2-thio-thymine, 4-thio-thymine, 5-propynyl-uracil, 4-thiouracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke- and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acids in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo[2.3-d] pyrimidin-5-yl, 2-amino-4-oxopyrolo [2, 3-d]pyrimidin-5-yl, 2-amino-4-oxopyrrolo[2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-CH$_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., Synlett, 1997, 1287-1290). Unnatural nucleic acids can include 2'-substituted 5'-CH$_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group (SC(CH$_3$)$_3$) (and analogs thereof); a methyleneamino group (CH$_2$NH$_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or C(R$_1$)(R$_2$) (R=H, C$_1$-C$_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O- methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O—, S-, or N-alkyl; O—, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[($CH_2$)$_n$O]$_m$ $CH_3$, —O($CH_2$)$_n$O$CH_3$, —O($CH_2$)$_n$$NH_2$, —O($CH_2$)$_n$$CH_3$, —O($CH_2$)$_n$O$NH_2$, and —O($CH_2$)$_n$ON[($CH_2$)$_n$ $CH_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, SCH3, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-$OCH_3$, and 2'-O($CH_2$)$_2$$OCH_3$ substituent groups. The substituent at the 2' position can also be selected from allyl, amino, azido, thio, O-allyl, O—($C_1$-$C_{10}$ alkyl), $OCF_3$, O($CH_2$)$_2$$SCH_3$, O($CH_2$)$_2$—O—N($R_m$)($R_n$), and O—$CH_2$—C(=O)—N($R_m$) ($R_n$), where each $R_m$ and $R_n$ is, independently, H or substituted or unsubstituted $C_1$-$C_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-CH ($CH_2OCH_3$)—O-2', and analogs thereof (see, U.S. Pat. No. 7,399,845); 4'-C($CH_3$)($CH_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086, 231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N*-dimethylhydrazine (—$CH_2$—N($CH_3$)—N($CH_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996)

Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMSOJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some cases, the unnatural nucleic acids further form unnatural base pairs. Exemplary unnatural nucleotides capable of forming an unnatural DNA or RNA base pair (UBP) under conditions in vivo includes, but is not limited to, 5SICS, d5SICS, NAM, dNaM, and combinations thereof. In some embodiments, unnatural nucleotides include:

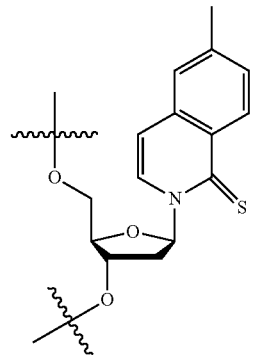

d5SICS

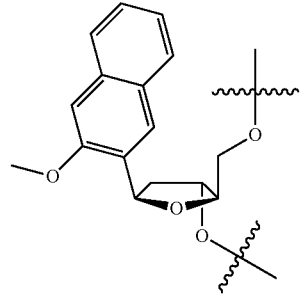

dNAM

-continued

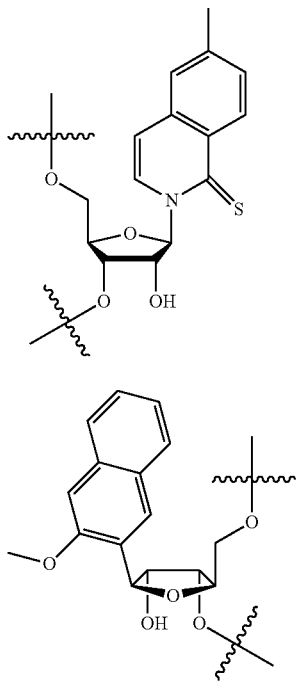

5SICS

NAM

In some embodiments, an unnatural base pair generate an unnatural amino acid described in Dumas et al., "Designing logical codon reassignment—Expanding the chemistry in biology," *Chemical Science*, 6: 50-69 (2015).

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s).

The orthogonal tRNA synthetase/tRNA pair charges a tRNA with an unnatural amino acid and incorporates the unnatural amino acid into the polypeptide chain in response to the codon. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs.

A cytokine (e.g., IL-2) polypeptide comprising an unnatural amino acid(s) are prepared by introducing the nucleic acid constructs described herein comprising the tRNA and tRNA synthetase and comprising a nucleic acid sequence of interest with one or more in-frame orthogonal (stop) codons into a host cell. The host cell is exposed to a physiological solution comprising the unnatural amino acid(s), and the host cells are then maintained under conditions which permit expression of the protein of interest's encoding sequence. The unnatural amino acid(s) is incorporated into the polypeptide chain in response to the codon. For example, one or more unnatural amino acids are incorporated into the cytokine (e.g., IL-2) polypeptide. Alternatively, two or more unnatural amino acids may be incorporated into the cytokine (e.g., IL-2) polypeptide at two or more sites in the protein.

When multiple unnatural amino acids are to be incorporated into a cytokine (e.g., IL-2) polypeptide, it will be understood that multiple codons will need to be incorporated into the encoding nucleic acid sequence at the desired positions such that the tRNA synthetase/tRNA pairs can direct the incorporation of the unnatural amino acids in response to the codon(s). At least 1, 2, 3, 4, or more codon encoding nucleic acids maybe incorporated into the nucleic acid sequence of interest.

When it is desired to incorporate more than one type of unnatural amino acid into the protein of interest into a single protein, a second or further orthogonal tRNA-tRNA synthetase pair may be used to incorporate the second or further unnatural amino acid; suitably said second or further orthogonal tRNA-tRNA synthetase pair recognizes a different codon in the nucleic acid encoding the protein of interest so that the two or more unnatural amino acids can be specifically incorporated into different defined sites in the protein in a single manufacturing step. In certain embodiments, two or more orthogonal tRNA-tRNA synthetase pairs may therefore be used.

Once the cytokine (e.g., IL-2) polypeptide incorporating the unnatural amino acid(s) has been produced in the host cell it can be extracted therefrom by a variety of techniques known in the art, including enzymatic, chemical and/or osmotic lysis and physical disruption. The cytokine (e.g., IL-2) polypeptide can be purified by standard techniques known in the art such as preparative chromatography, affinity purification or any other suitable technique.

Suitable host cells may include bacterial cells (e.g., *E. coli*), but most suitably host cells are eukaryotic cells, for example insect cells (e.g. *Drosophila* such as *Drosophila melanogaster*), yeast cells, nematodes (e.g. Celegans), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers maybe carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

Pharmaceutical Compositions and Formulations

In some embodiments, the pharmaceutical composition and formulations described herein are administered to a subject by multiple administration routes, including but not limited to, parenteral (e.g., intravenous, subcutaneous, intramuscular), intracerebral, oral, intranasal, buccal, rectal, sublingual, or transdermal administration routes.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pennsylvania 1975, Liberman, H. A. and Lachman, L., Eds., *Pharmaceutical Dosage Forms*, Marcel Decker, New York, N.Y., 1980, and *Pharmaceutical Dosage Forms and Drug Delivery Systems*, Seventh Ed. (Lippincott Williams & Wilkins 1999).

In some cases, the pharmaceutical composition is formulated as an immunoliposome, which comprises a plurality of IL-2 conjugates bound either directly or indirectly to lipid bilayer of liposomes. Exemplary lipids include, but are not limited to, fatty acids; phospholipids; sterols such as cholesterols; sphingolipids such as sphingomyelin; glycosphingolipids such as gangliosides, globocides, and cerebrosides; surfactant amines such as stearyl, oleyl, and linoleyl amines. In some instances, the lipid comprises a cationic lipid. In some instances, the lipid comprises a phospholipid. Exemplary phospholipids include, but are not limited to, phosphatidic acid ("PA"), phosphatidylcholine ("PC"), phosphatidylglycerol ("PG"), phophatidylethanolamine ("PE"), phosphatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), di stearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), di stearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), di stearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPT"), dilauroylphosphatidylinositol ("DLPI"), dilinoleoylphosphatidylinositol, dimyristoylphosphatidylinositol ("DMPP"), dioleoylphosphatidylinositol ("DOPT"), dipalmitoylphosphatidylinositol ("DPPI"), di stearoylphosphatidylinositol ("DSPI"), 1-palmitoyl-2-oleoyl-phosphatidylinositol ("POPT"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and SolkaFloc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, CabOSil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more of the cytokine (e.g., IL-2) polypeptides or cytokine (e.g., IL-2) conjugates disclosed herein, and optionally one or more pharmaceutical excipients described herein to facilitate the delivery of cytokine (e.g., IL-2) polypeptides or cytokine (e.g., IL-2) conjugates. Such kits further optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error, e.g., within 15%, 10%, or 5%.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "significant" or "significantly" in reference to binding affinity means a change in the binding affinity of the cytokine (e.g., IL-2 polypeptide) sufficient to impact binding of the cytokine (e.g., IL-2 polypeptide) to a target receptor. In some instances, the term refers to a change of at least 10%, 20%, 30%, 40%, 50%, 60%, 70%, 80%, 90%, 95%, or more. In some instances, the term means a change of at least 2-fold, 3-fold, 4-fold, 5-fold, 6-fold, 7-fold, 8-fold, 9-fold, 10-fold, 50-fold, 100-fold, 500-fold, 1000-fold, or more.

In some instances, the term "significant" or "significantly" in reference to activation of one or more cell populations via a cytokine signaling complex means a change sufficient to activate the cell population. In some cases, the change to activate the cell population is measured as a receptor signaling potency. In such cases, an EC50 value may be provided. In other cases, an ED50 value may be provided. In additional cases, a concentration or dosage of the cytokine may be provided.

As used herein, the term "potency" refers to the amount of a cytokine (e.g., IL-2 polypeptide) required to produce a target effect. In some instances, the term "potency" refers to the amount of cytokine (e.g., IL-2 polypeptide) required to activate a target cytokine receptor (e.g., IL-2 receptor). In other instances, the term "potency" refers to the amount of cytokine (e.g., IL-2 polypeptide) required to activate a target cell population. In some cases, potency is measured as ED50 (Effective Dose 50), or the dose required to produce 50% of a maximal effect. In other cases, potency is measured as EC50 (Effective Concentration 50), or the dose required to produce the target effect in 50% of the population.

EXAMPLES

These examples are provided for illustrative purposes only and not to limit the scope of the claims provided herein.

Example 1

Kinase and Cytokine Receptor Dimerization Assays
Cell Handling
PathHunter cell lines were expanded from freezer stocks according to standard procedures. Cells were seeded in a total volume of 20 µL into white walled, 384-well microplates and incubated for the appropriate time prior to testing.
Agonist Format
For agonist determination, cells were incubated with sample to induce response. Intermediate dilution of sample stocks was performed to generate 5× sample in assay buffer. About 5 µL of 5× sample was added to cells and incubated at 37° C. for 6 to 16 hours depending on the assay. Vehicle concentration was 1%.
Signal Detection
Assay signal was generated through a single addition of 12.5 or 15 µL (50% v/v) of PathHunter Detection reagent cocktail for agonist and antagonist assays respectively, followed by a one hour incubation at room temperature. For some assays, activity was detected using a high sensitivity detection reagent (PathHunter Flash Kit) to improve assay performance. In these assays, an equal volume of detection reagent (25 or 30 uL) was added to the wells, followed by a one hour incubation at room temperature. Microplates were read following signal generation with a PerkinElmer Envision™ instrument for chemilumine-scent signal detection.
Data Analysis
Compound activity was analyzed using CBIS data analysis suite (ChemInnovation, CA). For agonist mode assays, percentage activity was calculated using the following formula:

% Activity=100%×(mean RLU of test sample−mean RLU of vehicle control)/(mean MAX RLU control ligand−mean RLU of vehicle control).

For antagonist mode assays, percentage inhibition was calculated using the following formula:

% Inhibition=100%×(1−(mean RLU of test sample−mean RLU of vehicle control)/(mean RLU of EC80 control−mean RLU of vehicle control)).

Example 2

Ex-Vivo Immune Response Profiling of Exemplary IL-2 Compounds in Primary Human Leukocyte Reduction System (LRS)-Derived PBMC Samples To determine how the differential receptor specificity of exemplary IL-2 compounds affects activation of primary immune cell subpopulations, concentration-response profiling of lymphocyte activation in human LRS-derived peripheral blood mononuclear cell (PBMC) samples were performed using multi-color flow cytometry. These studies were performed at PrimityBio LLC (Fremont, CA). Primary lymphocytes derived from human LRS samples were treated with dilutions series of exemplary IL-2 compounds and quantified based on pSTAT5 signaling in each lymphocyte cell type using the panel shown in Table 1.

| Marker | Cell population |
|---|---|
| CD3 | T cells |
| CD4 | Th cells |
| CD8 | T effector cells |
| CD45RA | Naïve T cells |
| CD56 | NK cells |
| CD14/19 | Monocyte/B cells |
| CD25 | Tregs or experienced T cell |
| CD127 | Not Treg |
| CD62L | Memory T vs effector memory T cell |
| pSTAT5 (Y694) | Activation marker |

Flow cytometry data were analyzed for activation of different T and NK cell subsets in concentration-response mode, reading pSTAT5 accumulation after treatment with an exemplary IL-2 variant K9_30 kD.

Figure 4A:
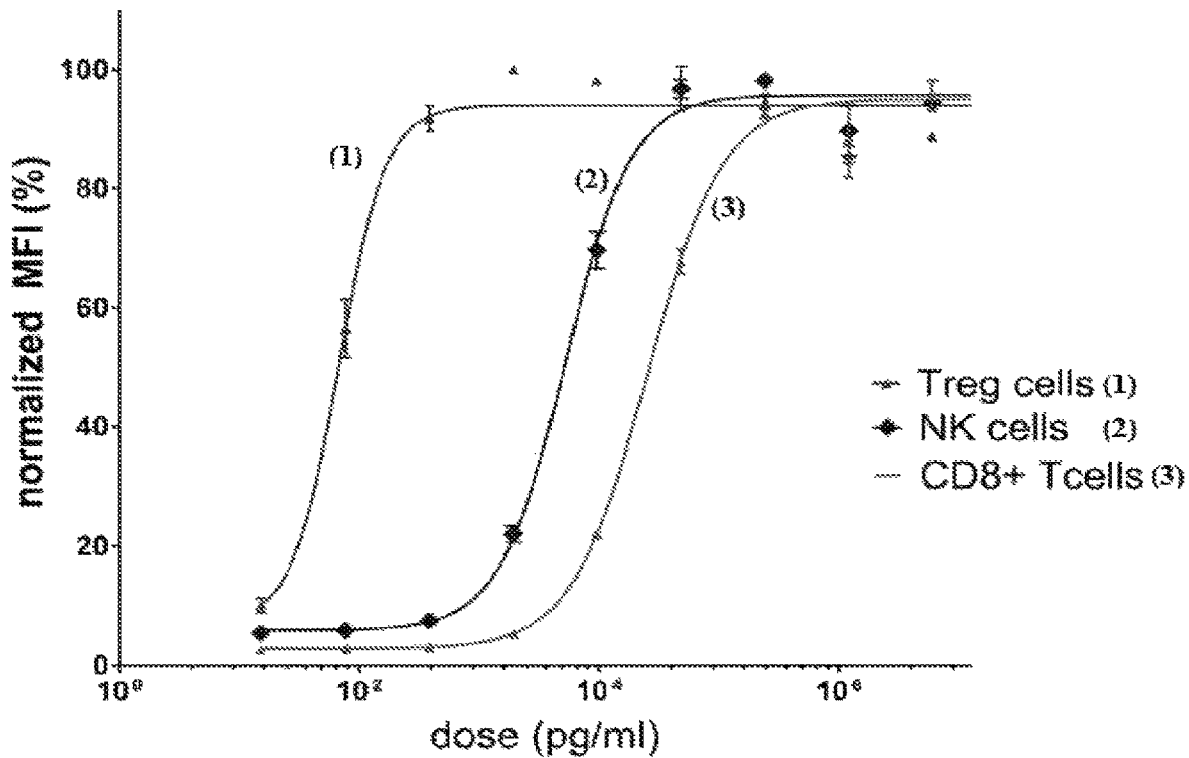
FIG. 4A-FIG. 4B show the dose response curves of an exemplary IL-2 variant for pSTAT5 signaling in human LRS primary cell (FIG. 4A) and proliferation response in mouse CTLL-2 populations (FIG. 4B).
Figure 4B:
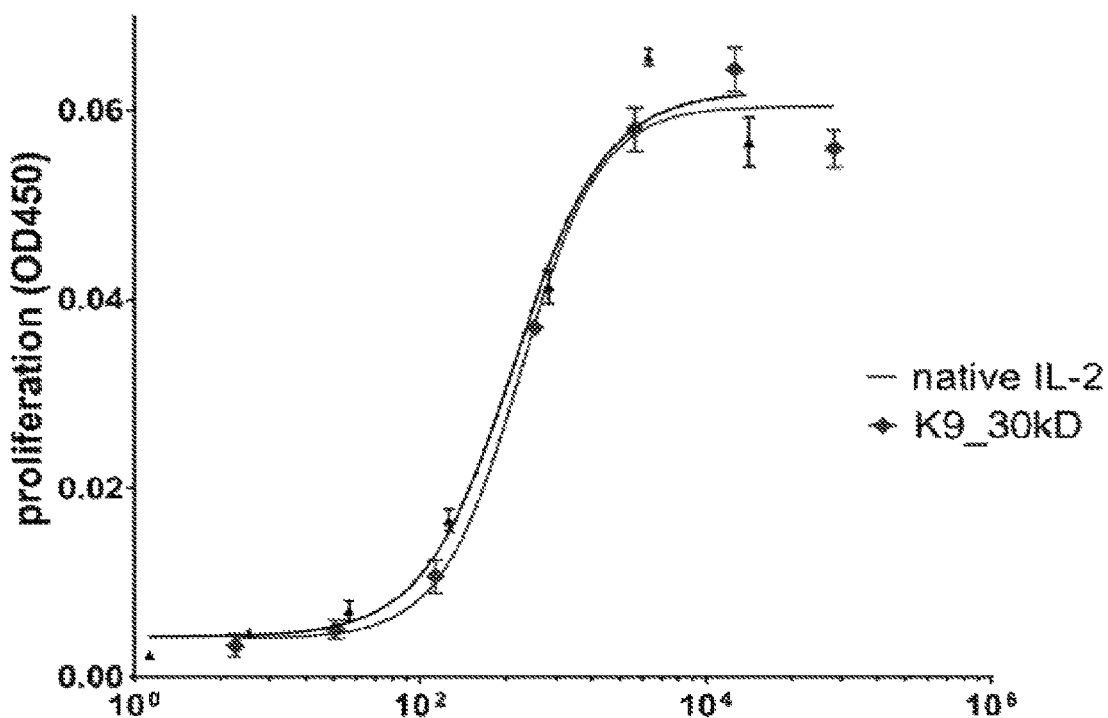

FIG. 4A-FIG. 4B show the dose response curves for pSTAT5 signaling in human LRS primary cell (FIG. 4A) and proliferation response in mouse CTLL-2 populations (FIG. 4B).

Table 2 shows the dose response EC50 for pSTAT5 signaling (EC50) in human LRS samples or CTLL-2 proliferation treated with indicated IL-2 variant.

| Compound | NK cells | CD8+ Tcells | Treg cells | CD8+/Treg ratio | Fold increase in Treg EC50 vs native IL-2 | CTLL-2 proliferation |
|---|---|---|---|---|---|---|
| native IL-2 | 4586 | 31024 | 75 | 414 | 1 | 455.8 |
| K9_30 kD | 169578 | 1100679 | 2217 | 496 | 30 | 504 |
| H16_30 kD | 2545257 | 12070108 | 34976 | 345 | 466 | 80755 |
| L19_30 kD | 6756768 | 22436430 | 93205 | 241 | 1243 | 3510 |
| D20_30 kD | 2643930 | 9505217 | 1129455 | 8 | 15059 | 689939 |
| M23_30 kD | 143620 | 539824 | 1030 | 524 | 14 | 1102 |
| N26_30 kD | 258531 | 1188859 | 2459 | 483 | 33 | 2594 |
| N88_30 kD | 3298113 | 11111537 | 323201 | 34 | 4309 | 66606 |
| E100_30 kD | 35088 | 195823 | 483 | 405 | 6 | 1676 |
| N119_30 kD | 34010 | 143380 | 535 | 268 | 11 | 1215 |
| T123_30 kD | 33396 | 152928 | 269 | 569 | 6 | 255 |
| Q126_30 kD | 3676807 | 19722480 | 29454 | 670 | 393 | 3584 |
| S127_30 kD | 20210 | 92190 | 150 | 615 | 3 | 123 |
| T131_30 kD | 24207 | 132922 | 258 | 515 | 3 | 641 |
| N88R/D109_30 kD | 2780819 | 12503386 | 175805 | 71 | 3663 | 59577 |
| V91K | 20537 | 102255 | 142 | 720 | 3 | 99.5 |
| N88R | 2312847 | 15025734 | 11082 | 1356 | 148 | 363 |

The EC50 values (pg/ml) were calculated from dose response curves generated from the MFI plots.

*Treg potency change compared to native IL-2 (wild-type IL-2) run in each individual experiment.

Example 3

PK Study in Tumor-Bearing C57BL/6 Mice

Experimental details are summaries in Table 3.

| Group | Number of Animals | Test/Control Article (dose) | Route, Dosing Regimen | End Point(s) |
|---|---|---|---|---|
| 1 | 9 | Native IL-2 (wild-type) (3.0 mg/kg) Concentration: 0.6 mg/mL | IV, single dose on Day 0 at T = 0 at 5 mL/kg | Blood collection at 0.08, 0.25, 0.5, 1, 2, 4, 8, 12, and 24 hours post dose |
| 2 | 9 | K35_30 kD (3.0 mg/kg) Concentration: 0.6 mg/mL | IV, single dose on Day 0 at T = 0 at 5 mL/kg | |
| 3 | 9 | K35_30 kD (0.3 mg/kg) Concentration: 0.6 mg/mL | IV, single dose on Day 0 at T = 0 at 5 mL/kg | |

-continued

| Group | Number of Test/Control Article Animals (dose) | Route, Dosing Regimen | End Point(s) |
|---|---|---|---|
| Extra | 6    N/A | N/A | Blank Matrix Collection (untimed) |
| Total | 33 | | |

The pharmacokinetic properties of an exemplary PEGylated IL-2 compound K35_30 kD at two dose levels were evaluated. The lyophilized test article was reconstituted in PBS, and nine male C57BL/6 mice were dosed with 0.3 and 3 mg/kg via intravenous tail vein injection for each dose group (see collection details below). Blood samples were collected at 0.08, 0.25, 0.5, 1, 2, 4, 8, 12, and 24 hours post dose. The hIL-2 ELISA kit from Abcam (ab100566), which does not cross-react with native mouse IL-2, was used for detection and quantitation of test articles. To adjust for ELISA-specific differences in sensitivity of kit detection of native and PEGylated compounds, native IL-2 and K35_30 kD test article standard curves were generated using the test article diluent buffer, and data were analyzed with respect to respective standard curves. The data plotted represent the mean and SEM of three individual samples (biological replicates) as described above, and PK parameters for K35_30 kD test articles were extracted and summarized in Table 4.

| | | | Dose | |
|---|---|---|---|---|
| Analyte | Parameter | Unit | 0.3 mg/kg Estimate | 3 mg/kg |
| IL-2 K35-mPEG30 kD | $T_{max}$ | hr | 0.250 | 0.250 |
| | $C_{max}$ | ng/mL | 6080 | 57700 |
| | $AUC_{0-t}$ | hr*/ng/mL | 38500 | 425000 |
| | $R^2$ | | 0.994 | 0.947 |
| | $AUC_{1/2extrap}$ | % | 35.3 | 37.4 |
| | $AUC_{0-\infty}$ | h*ng/mL | 59600 | 679000 |
| | $t_{1/2}$ | hr | 18.2 | 19.5 |
| | $C_{max}/D$ | kg*ng/mL/mg | 20300 | 19200 |
| | $AUC_{0-t}/D$ | hr*ng/mL | 128000 | 142000 |

Figure 5:
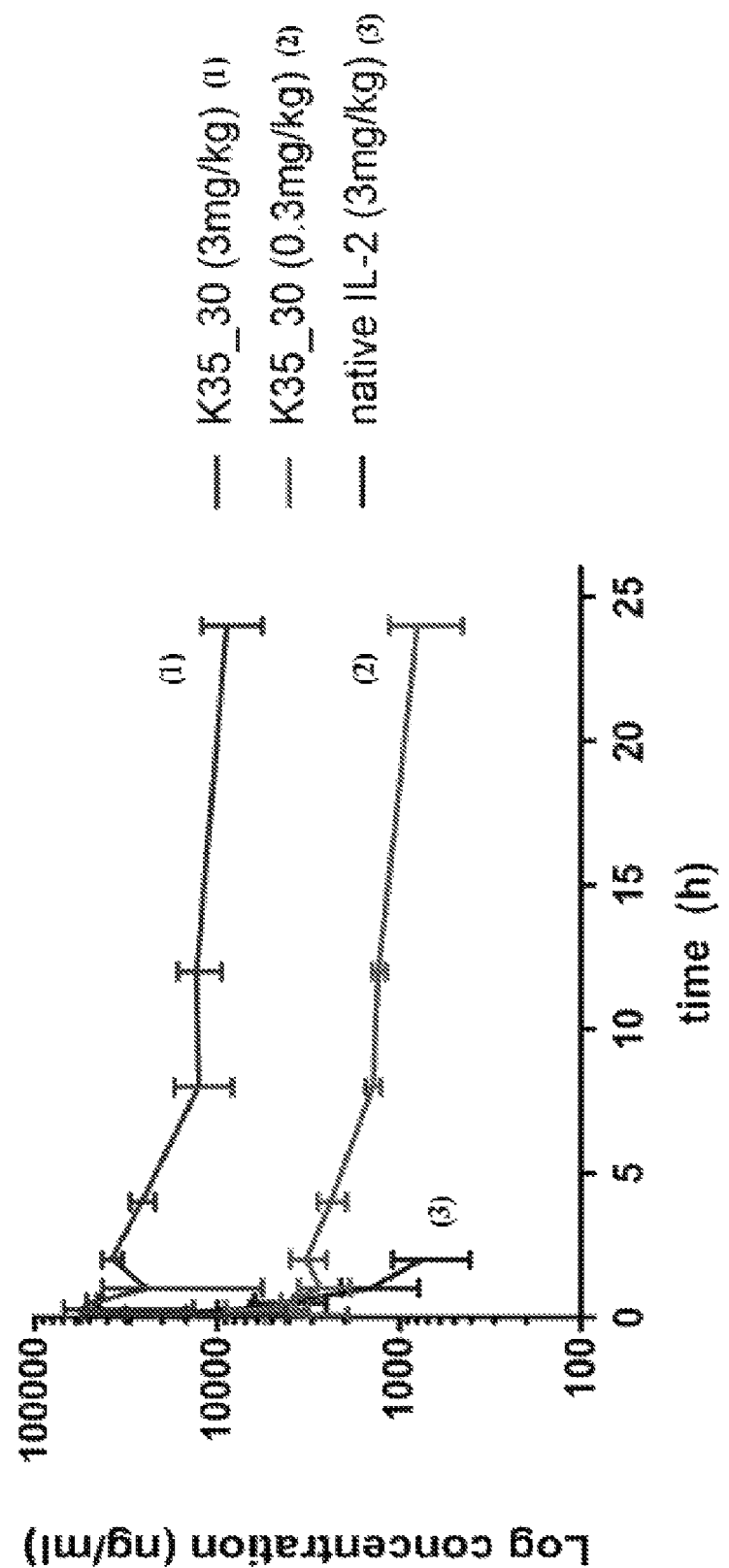
FIG. 5 shows enhanced PK profile of an exemplary IL-2 molecule K35_30 kD at two different concentrations.

FIG. 5 shows enhanced PK profile of K35_30 kD at two different concentrations. Their PK profiles are compared to wild-type IL-2.

Example 4

Table 5 illustrates IL-2 sequences described herein.

| Name | Sequence | SEQ ID NO: |
|---|---|---|
| IL-2 (homo sapiens) (mature form) | APTSSSTKKTQLQLEHLLLDLQMILNG INNYKNPKLTRMLTFKFYMPKKATELK HLQCLEEELKPLEEVLNLAQSKNFHLR PRDLISNINVIVLELKGSETTFMCEYA DETATIVEFLNRWITFCQSIISTLT | 1 |
| IL-2 (homo sapiens) (precursor) NCBI Accession No.: AAB46883.1 | MYRMQLLSCIALSLALVTNSAPTSSST KKTQLQLEHLLLDLQMILNGINNYKNP KLTRMLTFKFYMPKKATELKHLQCLEE ELKPLEEVLNLAQSKNFHLRPRDLISN INVIVLELKGSETTFMCEYADETATIV EFLNRWITFCQSIISTLT | 2 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of expanding CD4+ regulatory T (Treg) cells in a subject in need thereof, comprising administering to a subject having an autoimmune disease or disorder a therapeutically effective amount of a modified interleukin 2 (IL-2) polypeptide comprising an IL-2 polypeptide comprising at least one unnatural amino acid covalently attached to a conjugating moiety,
   wherein the position of the at least one unnatural amino acid is K9, H16, L19, V91, E100, or T123, wherein the residue positions correspond to positions 9, 16, 19, 91, 100, and 123 as set forth in SEQ ID NO: 1; and
   wherein the IL-2 polypeptide comprises at least 90% sequence identity to SEQ ID NO: 1.

2. The method of claim 1, wherein the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

3. The method of claim 1, wherein the position of the at least one unnatural amino acid is H16.

4. The method of claim 1, wherein the position of the at least one unnatural amino acid is K9 or L19.

5. The method of claim 1, wherein the at least one unnatural amino acid is a lysine analogue or comprises an aromatic side chain.

6. The method of claim 1, wherein the at least one unnatural amino acid comprises p-acetyl-L-phenylalanine, p-azidomethyl-L-phenylalanine (pAMF), p-iodo-L-phenylalanine, m-acetylphenylalanine, p-propargyloxyphenylalanine, p-propargyl-phenylalanine, 3-methyl-phenylalanine, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, O-allyltyrosine, O-methyl-L-tyrosine, O-4-allyl-L-tyrosine, 4-propyl-L-tyrosine, phosphonotyrosine, L-3-(2-naphthyl) alanine, 2-amino-3-((2-((3-(benzyloxy)-3-oxopropyl)amino)ethyl) selanyl) propanoic acid, or 2-amino-3-(phenylselanyl) propanoic acid.

7. The method of claim 1, wherein the IL-2 polypeptide comprises an N-terminal deletion, wherein the N-terminal deletion comprises a deletion of the first 1, 2, 3, 4, 5, 6, 7, 8, 9, 10, 11, or 12 residues from the N-terminus, wherein the residue positions correspond to the positions as set forth in SEQ ID NO: 1.

8. The method of claim 1, wherein the conjugating moiety comprises a water-soluble polymer, a lipid, a protein, or a peptide.

9. The method of claim 8, wherein the conjugating moiety comprises a water-soluble polymer.

10. The method of claim 9, wherein the water-soluble polymer comprises polyethylene glycol (PEG), poly (propylene glycol) (PPG), copolymers of ethylene glycol and propylene glycol, poly (oxyethylated polyol), poly (olefinic alcohol), poly (vinylpyrrolidone), poly (hydroxyalkylmethacrylamide), poly (hydroxyalkylmethacrylate), poly (saccharides), poly (a-hydroxy acid), poly (vinyl alcohol), polyphosphazene, polyoxazolines (POZ), poly (N-acryloylmorpholine), or a combination thereof.

11. The method of claim 10, wherein the water-soluble polymer comprises PEG.

12. The method of claim 11, wherein the PEG has a molecular weight from about 10 kDa to about 85 kDa.

13. The method of claim 12, wherein the PEG has a molecular weight of about 20 kDa, about 25 kDa, about 30 kDa, about 35 kDa, about 40 kDa, about 45 kDa, about 50 kDa, about 55 kDa, or about 60 kDa.

14. The method of claim 13, wherein the PEG has a molecular weight of about 50 kDa.

15. The method of claim 1, wherein the at least one unnatural amino acid is covalently attached to the conjugating moiety through a linker, wherein the linker comprises a homobifunctional linker, a heterobifunctional linker, a cleavable or a non-cleavable dipeptide linker, a spacer, or a combination thereof.

16. The method of claim 1, wherein the IL-2 polypeptide comprises at least about 95% sequence identity to SEQ ID NO: 1.

17. The method of claim 16, wherein the IL-2 polypeptide comprises at least 97% sequence identity to SEQ ID NO: 1.

18. The method of claim 1, wherein the modified IL-2 polypeptide is administered as a pharmaceutical composition comprising the modified IL-2 polypeptide.

19. The method of claim 1, wherein the conjugating moiety comprises PEG, wherein the position of the at least one unnatural amino acid is H16, wherein the residue position corresponds to position 16 as set forth in SEQ ID NO: 1, and wherein the at least one unnatural amino acid is a lysine analogue.

20. The method of claim 1, further comprising administering to the subject an additional therapeutic agent.

21. The method of claim 20, wherein the modified IL-2 polypeptide is administered prior to the administration of the additional therapeutic agent.

22. The method of claim 20, wherein the modified IL-2 polypeptide is administered after the administration of the additional therapeutic agent.

23. The method of claim 1, wherein the modified IL-2 polypeptide selectively expands CD4+Treg cells in the subject.

\* \* \* \* \*